(12) United States Patent
Saito et al.

(10) Patent No.: US 10,016,439 B2
(45) Date of Patent: Jul. 10, 2018

(54) FUSED IMIDAZOLE COMPOUNDS

(71) Applicant: ONO PHARMACEUTICAL CO., LTD., Osaka-shi, Osaka (JP)

(72) Inventors: Tetsuji Saito, Osaka (JP); Masato Higashino, Osaka (JP); Soichi Kawaharada, Osaka (JP); Arwel Lewis, Essex (GB); Mark Stuart Chambers, Essex (GB); Alastair Rae, Essex (GB); Kim Louise Hirst, Essex (GB); Charles David Hartley, Essex (GB)

(73) Assignee: ONO PHARMACEUTICAL CO., LTD., Osaka-Shi (JP)

( * ) Notice: Subject to any disclaimer, the term of this patent is extended or adjusted under 35 U.S.C. 154(b) by 0 days.

(21) Appl. No.: 15/112,647

(22) PCT Filed: Jan. 30, 2015

(86) PCT No.: PCT/JP2015/053314
§ 371 (c)(1),
(2) Date: Jul. 19, 2016

(87) PCT Pub. No.: WO2015/115673
PCT Pub. Date: Aug. 6, 2015

(65) Prior Publication Data
US 2016/0331757 A1 Nov. 17, 2016

(30) Foreign Application Priority Data
Jan. 31, 2014 (JP) .................................. 2014-017798

(51) Int. Cl.
*A61K 31/5383* (2006.01)
*C07D 403/12* (2006.01)
(Continued)

(52) U.S. Cl.
CPC ...... *A61K 31/5383* (2013.01); *A61K 31/4184* (2013.01); *A61K 31/423* (2013.01);
(Continued)

(58) Field of Classification Search
None
See application file for complete search history.

(56) References Cited

FOREIGN PATENT DOCUMENTS

| WO | WO-96/20711 A1 | 7/1996 |
| WO | WO-00/37471 A1 | 6/2000 |

(Continued)

OTHER PUBLICATIONS

The Organic Chemistry of Drug Design and Drug Action, Silverman, Academic Press, 1992, pp. 352-355, see pp. 354-355.*
(Continued)

*Primary Examiner* — Karl J Puttlitz
(74) *Attorney, Agent, or Firm* — Foley & Lardner LLP

(57) ABSTRACT

The present invention provides compounds represented by formula (I), pharmaceutically acceptable salts thereof, N-oxides thereof, solvates thereof or prodrugs thereof (wherein the characters are as defined in the description). The compounds represented by formula (I) have affinity and selectivity for the gamma-aminobutyric acid A receptor subunit alpha 5 ($GABA_A$ α5) and act as $GABA_A$ α5 negative allosteric modulators ($GABA_A$ α5 NAM), so that they are (Continued)

useful in the prevention and/or treatment of diseases which are related to the GABA$_A$ α5 such as Alzheimer's disease.

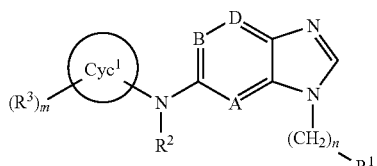

(I)

16 Claims, 1 Drawing Sheet

(51) Int. Cl.
| | |
|---|---|
| C07D 401/14 | (2006.01) |
| C07D 413/14 | (2006.01) |
| A61K 31/4439 | (2006.01) |
| A61K 31/4709 | (2006.01) |
| A61K 31/517 | (2006.01) |
| A61K 31/538 | (2006.01) |
| C07D 401/12 | (2006.01) |
| C07D 413/12 | (2006.01) |
| C07D 471/04 | (2006.01) |
| C07D 473/32 | (2006.01) |
| C07D 498/04 | (2006.01) |
| C07D 519/00 | (2006.01) |
| A61K 31/4184 | (2006.01) |
| A61K 31/423 | (2006.01) |
| A61K 31/437 | (2006.01) |
| A61K 31/4985 | (2006.01) |
| A61K 45/06 | (2006.01) |
| C07D 487/04 | (2006.01) |

(52) U.S. Cl.
CPC ........ *A61K 31/437* (2013.01); *A61K 31/4439* (2013.01); *A61K 31/4709* (2013.01); *A61K 31/4985* (2013.01); *A61K 31/517* (2013.01); *A61K 31/538* (2013.01); *A61K 45/06* (2013.01); *C07D 401/12* (2013.01); *C07D 401/14* (2013.01); *C07D 403/12* (2013.01); *C07D 413/12* (2013.01); *C07D 413/14* (2013.01); *C07D 471/04* (2013.01); *C07D 473/32* (2013.01); *C07D 487/04* (2013.01); *C07D 498/04* (2013.01); *C07D 519/00* (2013.01)

(56) References Cited

FOREIGN PATENT DOCUMENTS

| WO | WO-02/050062 A2 | 6/2002 |
| WO | WO-2004/065378 A1 | 8/2004 |
| WO | WO-2005/028479 A2 | 3/2005 |
| WO | WO-2009-103966 A1 | 8/2009 |
| WO | WO-2013/117645 A1 | 8/2013 |

OTHER PUBLICATIONS

Gill et al., Curr Pharm Des. 2014 20(31) 5069-5076.*
Atack et al., "In Vitro and in Vivo Properties of 3-tert-Butyl-7-(5-methylisoxazol-3-yl)-2-(1-methyl-1H-1,2,4-triazol-5-ylmethoxy)-pyrazolo[1,5d]-[1,2,4]triazine (MRK-016), a GABA$_A$ Receptor α5 Subtype-Selective Inverse Agonist," The Journal of Pharmacology and Experimental Therapeutics 331(2):470-484 (2009).
Atack, John R., "Preclinical and clinical pharmacology of the GABA$_A$ receptor α5 subtype-selective inverse agonist α5IA," Pharmacology & Therapeutics 125:11-26 (2010).
Ballard et al., "RO4938581, a novel cognitive enhancer acting at GABA$_A$ α5 subunit-containing receptors," Psychopharmacology 202:207-223 (2009).
Dawson et al., "An Inverse Agonist Selective for α5 Subunit-Containing GABA$_A$ Receptors Enhances Cognition," The Journal of Pharmacology and Experimental Therapeutics 316(3):1335-1345 (2006).
Demange et al., "Synthesis of 6-Pyridylaminopurines," Heterocycles 75(7):1735-1743 (2008).
Knust et al., "The discovery and unique pharmacological profile of RO4938581 and RO4882224 as potent and selective GABA$_A$ α5 inverse agonists for the treatment of cognitive dysfunction," Bioorganic & Medicinal Chemistry Letters 19:5940-5944 (2009).
International Search Report and Written Opinion of the International Search Authority for PCT/JP2015/053314 dated Apr. 21, 2015.
Extended European Search Report dated Aug. 21, 2017 for corresponding European Patent Application No. 15742892.1.

* cited by examiner

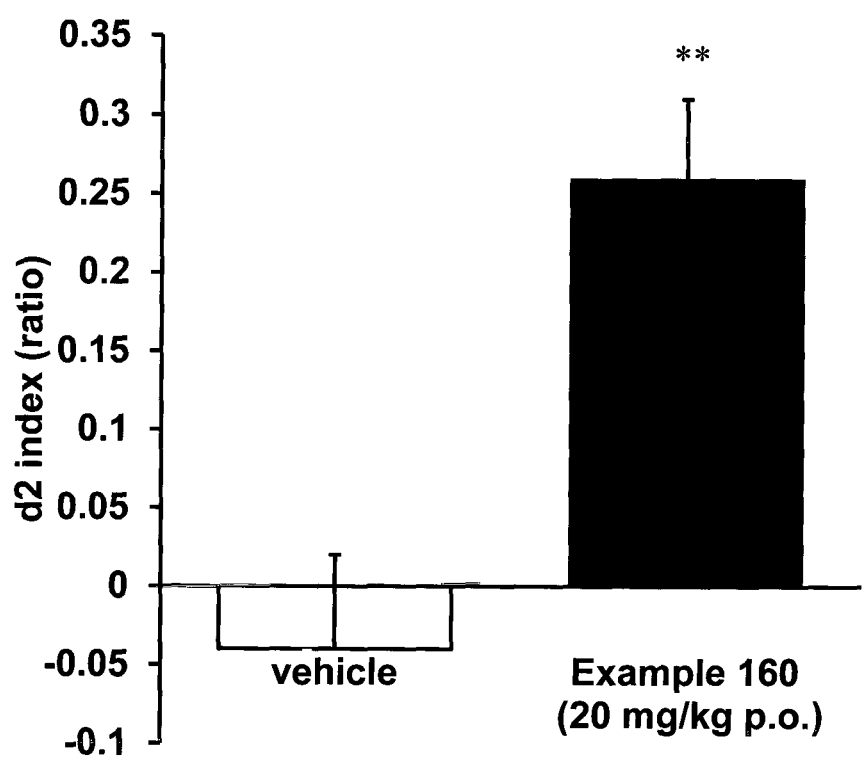

FUSED IMIDAZOLE COMPOUNDS

CROSS-REFERENCE TO RELATED APPLICATIONS

The present application is a U.S. National Phase of International Patent Application No. PCT/JP2015/053314, filed Jan. 30, 2015, which claims priority to Japanese Patent Application No. 2014-017798, filed Jan. 31, 2014, the entireties of which are incorporated herein by reference.

TECHNICAL FIELD

The present invention relates to a compound represented by formula (I):

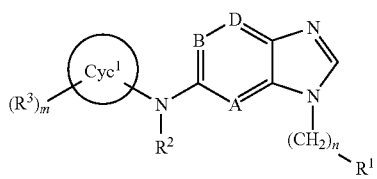

(I)

wherein all the symbols have the same meanings as defined hereinafter.

BACKGROUND ART

The gamma-aminobutyric acid A receptor ($GABA_A$) ion channel containing the α5 subunit is highly expressed in the hippocampus which is a key to cognitive function. Compounds with α5 subtype selective negative allosteric modulator (NAM) activity have been shown to improve cognition in rodent behavioral models (see non patent literatures 1-3). Similar phenotypes have been observed in animals with point mutations of the α5 subunit. These observations indicate that a $GABA_A$ α5 NAM is likely to treat cognitive disorders like Alzheimer's disease or to produce cognitive enhancement in human. Indeed, the α5 subtype selective NAM, α5IA has shown to block the alcohol-induced memory impairment of word list learning in healthy volunteers (see non patent literature 4).

Compounds that show NAM activity on all GABA receptor subtypes cause convulsions or have proconvulsant activity. Therefore, drugs which have affinity and selectivity for the $GABA_A$ α5 and act as $GABA_A$ α5 NAM are desired. However, because of the high homology among the primary sequences of GABA receptor subtypes, it has proven difficult to identify compounds that show high selectivity to one subtype over the other members in the family.

Meanwhile, it has been described in patent literature 1 that a compound represented by formula (A):

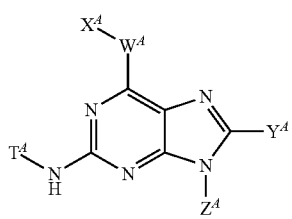

(A)

wherein $W^A$ is oxygen or sulfur; $X^A$ is optionally substituted lower alkyl, optionally substituted aryl or optionally substituted heteroaryl; $Y^A$ is hydrogen or lower alkyl; $Z^A$ is optionally substituted lower alkyl; and $T^A$ is optionally substituted aryl or optionally substituted heteroaryl; selectively binds to $GABA_A$ receptors and is a highly selective agonist, antagonist or inverse agonist for $GABA_A$ brain receptors.

In addition, Patent literature 1 describes the following intermediate compound:

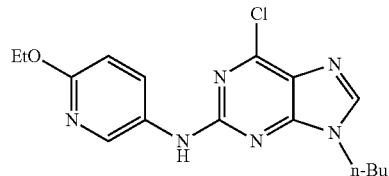

9-butyl-6-chloro-N-(6-ethoxypyridin-3-yl)-9H-purin-2-amine

However, the present compounds are not described in Patent literature 1. Patent literature 1 does not describe $GABA_A$ α5, let alone selectivity for the $GABA_A$ α5. Based on the fact that the compound of formula (A) binds to the $GABA_A$ receptor, the authors of patent literature 1 mention all possibilities as to the function of the compound (i.e., it may be an agonist, antagonist or inverse agonist of the $GABA_A$ receptor), without investigating it further. Accordingly, the actual function of the compound of formula (A) cannot be determined from patent literature 1. Namely, there is neither the description nor the suggestion regarding selective $GABA_A$ α5 NAM in patent literature 1.

Patent literature 2 describes a compound represented by formula (B):

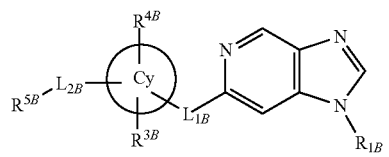

(B)

wherein $R^{1B}$ is Me, Et or cyclopropyl, each of which is optionally substituted; $L_{1B}$ is —$NR^{2B}$—; Cy is phenyl; $L_{2B}$ is absent; $R^{5B}$ is optionally substituted 5-6 membered heteroaryl comprising 1 to 4 heteroatoms.

Patent literature 3 describes the following compound:

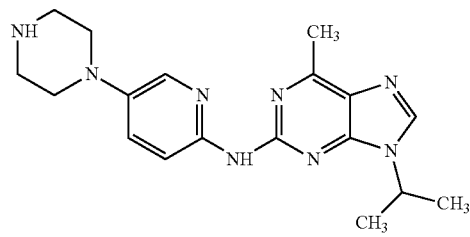 [SMILES: Cc1nc(Nc2ccc(N3CCNCC3)cn2)nc2c1ncn2C(C)C]

(9-isopropyl-6-methyl-9H-purin-2-yl)-(5-piperazin-1-yl-pyridin-2-yl)-amine

Patent literature 4 describes the following compound:

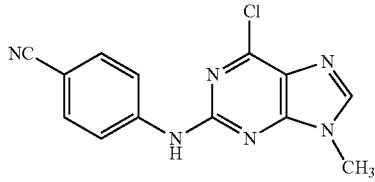 [SMILES: Cn1cnc2c(Cl)nc(Nc3ccc(C#N)cc3)nc21]

4-[(6-chloro-9-methyl-9H-purin-2-yl)amino]benzonitrile

Patent literature 5 describes the following compound:

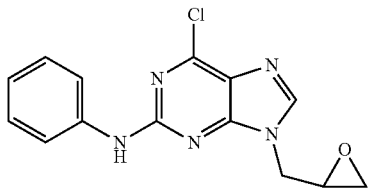 [SMILES: Clc1nc(Nc2ccccc2)nc2c1ncn2CC1CO1]

6-chloro-9-(oxiran-2-ylmethyl)-N-phenyl-9H-purin-2-amine

Non-patent literature 6 describes the following compound:

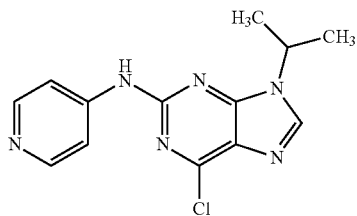 [SMILES: CC(C)n1cnc2c(Cl)nc(Nc3ccncc3)nc21]

6-chloro-9-(propan-2-yl)-N-(pyridin-4-yl)-9H-purin-2-amine

However, Patent literatures 2 to 5 and Non-patent literature 6 do not describe the present compounds. In addition, none of them describes $GABA_A$ receptor.

PRIOR ART LITERATURES

Patent Literatures

Patent literature 1: International Publication No WO2000/037471
Patent literature 2: International Publication No WO2013/117645
Patent literature 3: International Publication No WO2004/065378
Patent literature 4: International Publication No WO2005/028479
Patent literature 5: International Publication No WO1996/020711

Non-Patent Literatures

Non-patent literature 1: Journal of Pharmacology and Experimental Therapeutics, 2009, vol. 331, pp. 470-484
Non-patent literature 2: Psychopharmacology, 2009, vol. 202, pp. 207-223
Non-patent literature 3: Journal of Pharmacology and Experimental Therapeutics, 2006, vol. 316, pp. 1335-1345
Non-patent literature 4: Pharmacology & Therapeutics, 2010, vol. 125, pp. 11-26
Non-patent literature 5: Bioorganic & Medicinal Chemistry Letters, 2009, vol. 19, pp. 5940-5944
Non-patent literature 6: Heterocycles (2008), 75(7), 1735-1743

DISCLOSURE OF THE INVENTION

The present invention provides novel compounds which have affinity and selectivity for the gamma-aminobutyric acid A receptor subunit alpha 5 ($GABA_A$ α5) and act as $GABA_A$ α5 negative allosteric modulators ($GABA_A$ α5 NAM), and their use for the prevention and/or treatment of diseases which are related to the $GABA_A$ α5 such as Alzheimer's disease, as well as pharmaceutical compositions comprising such compounds.

That is, the present invention relates to:
(1) A compound represented by formula (I):

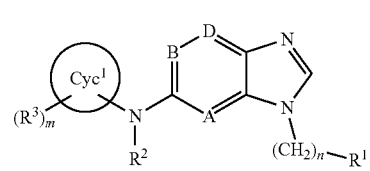

wherein A represents $CR^4$ or N;
B represents $CR^5$ or N;
D represents $CR^6$ or N;
$Cyc^1$ represents a (1) 5- to 15-membered mono-, bi- or tri-cyclic aromatic carbocyclic ring which may be partially saturated or (2) 5- to 15-membered mono-, bi- or tri-cyclic aromatic heterocyclic ring having 1 to 5 heteroatoms independently selected from nitrogen, oxygen and sulfur, which may be partially saturated;
$R^1$ represents (1) 3- to 5-membered cycloalkyl wherein one carbon atom may be replaced by oxygen, which may be substituted with one or more groups independently selected from halogen and C1-4 alkyl which may be substituted with halogen or (2) C1-4 alkyl which may be substituted with halogen;
$R^2$ represents hydrogen or C1-4 alkyl;
$R^3$ represents (1) oxo, (2) halogen, (3) cyano, (4) hydroxy, (5) C1-6 alkyl which may be substituted with $R^7$, (6) C1-6 alkoxy which may be substituted with $R^7$, (7) 3- to 5-membered cycloalkyl wherein one carbon atom may be replaced by oxygen, which may be substituted with $R^8$, (8) 5- to 12-membered mono- or bi-cyclic aromatic carbocyclic ring which may be partially or fully saturated and may be substituted with $R^8$ or (9) 5- to 12-membered mono- or bi-cyclic aromatic heterocyclic ring having 1 to 5 heteroatoms independently selected from nitrogen, oxygen and sulfur, which may be partially or fully saturated and may be substituted with $R^8$;

$R^4$ represents hydrogen or halogen;

$R^5$ represents (1) hydrogen, (2) halogen, (3) hydroxy, (4) cyano, (5) C1-6 alkyl which may be substituted with $R^9$, (6) C2-6 alkenyl which may be substituted with $R^9$, (7) C1-6 alkoxy which may be substituted with $R^9$, (8) C1-6 alkyl-carbonyl which may be substituted with $R^9$ or (9) 3- to 5-membered cycloalkyl wherein one carbon atom may be replaced by oxygen, which may be substituted with $R^9$;

$R^6$ represents hydrogen, halogen or C1-4 alkyl which may be substituted with halogen;

$R^7$ represents (1) halogen, (2) hydroxy, (3) C1-4 alkoxy or (4) 3- to 5-membered cycloalkyl wherein one carbon atom may be replaced by oxygen, which may be substituted with one or more groups independently selected from halogen and hydroxy;

$R^8$ represents (1) oxo, (2) halogen, (3) cyano, (4) hydroxy, (5) C1-6 alkyl which may be substituted with one or more groups independently selected from halogen and hydroxy or (6) 3- to 5-membered cycloalkyl which may be substituted with one or more groups independently selected from halogen and hydroxy;

$R^9$ represents halogen or hydroxy;

n represents an integer of 0 to 2; and m represents an integer of 0 to 7, wherein when m represents an integer of 2 to 7, each $R^3$ may be same or different;

with the proviso that when A is CH, B is N, D is CH, n is 1, $R^1$ is cyclopropyl and $R^2$ is hydrogen, then $Cyc^1$ is not benzene, pyridine, pyrazole or benzodioxole;

with the proviso that (a) the compound represented by formula (I), wherein D is CH, and (1) $R^1$ is C1-4 alkyl which may be substituted with halogen or (2) n is 0 and $R^1$ is cycloalkyl, (b) (9-isopropyl-6-methyl-9H-purin-2-yl)-(5-piperazin-1-yl-pyridin-2-yl)-amine, (c) 9-butyl-6-chloro-N-(6-ethoxypyridin-3-yl)-9H-purin-2-amine, (d) 4-[(6-chloro-9-methyl-9H-purin-2-yl)amino]benzonitrile, (e) 6-chloro-9-(oxiran-2-ylmethyl)-N-phenyl-9H-purin-2-amine and (f) 6-chloro-9-(propan-2-yl)-N-(pyridin-4-yl)-9H-purin-2-amine are excluded, or a pharmaceutically acceptable salt thereof, an N-oxide thereof, a solvate thereof or a prodrug thereof.

(2) The compound according to the above item (1), which is a compound represented by formula (I-A):

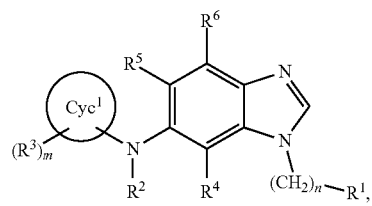

(I-A)

a compound represented by formula (I-B):

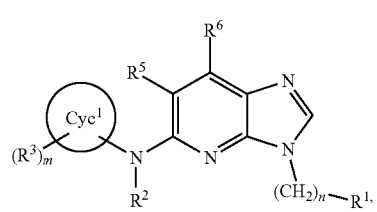

(I-B)

a compound represented by formula (I-C):

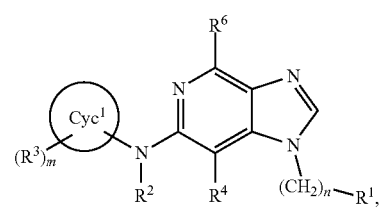

(I-C)

a compound represented by formula (I-D):

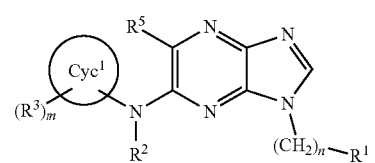

(I-D)

or a compound represented by formula (I-E):

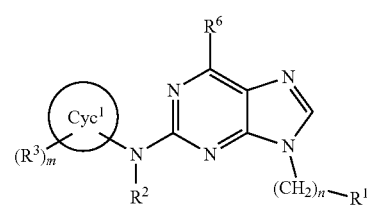

(I-E)

wherein all the symbols have the same meanings as described in the above item (1).

(3) The compound according to the above item (2), which is the compound represented by formula (I-A), (I-B), (I-C) or (I-E), wherein $R^6$ represents halogen or C1-4 alkyl which may be substituted with halogen.

(4) The compound according to any one of the above items (1) to (3), wherein $R^1$ represents cyclopropyl, cyclobutyl, oxetanyl, tetrahydrofuranyl, n-propyl or isopropyl, any of which may be substituted with 1 to 3 halogen.

(5) The compound according to any one of the above items (1) to (4), wherein n represents 0 or 1.

(6) The compound according to any one of the above items (1) to (5), wherein $R^2$ represents hydrogen.

(7) The compound according to any one of the above items (1) to (6), wherein

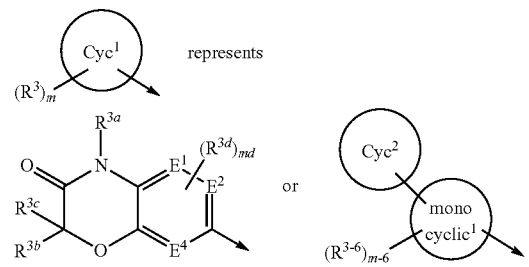

wherein E¹, E² and E⁴ each independently represent a carbon atom or a nitrogen atom, with the proviso that at least two of E¹, E² and E⁴ are carbon atoms;

R$^{3a}$ represents (1) hydrogen, (2) C1-4 alkyl which may be substituted with 1 to 3 groups selected from halogen, hydroxy and methoxy or (3) —(CH$_2$)$_p$-(3- to 5-membered cycloalkyl), wherein one carbon atom in cycloalkyl may be replaced by oxygen and p represents 0 or 1;

R$^{3b}$ and R$^{3c}$ each independently represent (1) hydrogen, (2) halogen or (3) C1-4 alkyl;

R$^{3d}$ represents halogen or C1-4 alkyl;

md represents an integer of 0 to 2, wherein when md represents 2, each R$^{3d}$ may be same or different;

monocyclic¹ represents (1) 5- to 7-membered mono-cyclic aromatic carbocyclic ring which may be partially saturated or (2) 5- to 7-membered mono-cyclic aromatic heterocyclic ring having 1 to 3 heteroatoms independently selected from nitrogen, oxygen and sulfur, which may be partially saturated;

Cyc² represents (1) 5- to 6-membered mono-cyclic aromatic heterocyclic ring having 1 to 3 heteroatoms independently selected from nitrogen, oxygen and sulfur, which may be partially or fully saturated and may be substituted with 1 to 3 groups selected from oxo, halogen, cyano, hydroxy and C1-4 alkyl which may be substituted with 1 to 3 groups selected from halogen and hydroxy or (2) 8- to 12-membered bicyclic aromatic heterocyclic ring having 1 to 5 heteroatoms independently selected from nitrogen, oxygen and sulfur, which may be partially or fully saturated and may be substituted with 1 to 5 groups selected from oxo, halogen, cyano, hydroxy and C1-4 alkyl which may be substituted with 1 to 3 groups selected from halogen and hydroxy;

R$^{3-6}$ represents halogen or C1-4 alkyl which may be substituted with 1 to 3 halogen;

m-6 represents 0 to 2; wherein when m-6 represents 2, each R$^{3-6}$ may be same or different and the arrow represents a binding position to the N(R²).

(8) The compound according to any one of the above item (1) to (7), wherein a compound represented by formula (IV):

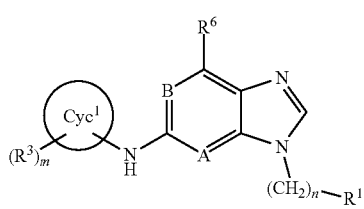

(IV)

wherein A represents CR⁴ or N;

B represents CR⁵ or N;

R¹ represents cyclopropyl, cyclobutyl, oxetanyl, tetrahydrofuranyl, n-propyl or isopropyl, any of which may be substituted with 1 to 3 halogen;

R⁴ represents hydrogen or halogen;

R⁵ represents (1) hydrogen, (2) halogen, (3) hydroxy, (4) cyano, (5) C1-4 alkyl which may be substituted with 1 to 3 groups selected from halogen and hydroxy, (6) C2-4 alkenyl which may be substituted with 1 to 3 groups selected from halogen and hydroxy, (7) C1-4 alkoxy which may be substituted with 1 to 3 groups selected from halogen and hydroxy, (8) C1-4 alkyl-carbonyl which may be substituted with 1 to 3 groups selected from halogen and hydroxy or (9) 3- to 5-membered cycloalkyl wherein one carbon atom may be replaced by oxygen, which may be substituted with 1 to 3 groups selected from halogen and hydroxyl;

R⁶ represents halogen or methyl which may be substituted with halogen;

n represents 0 or 1;

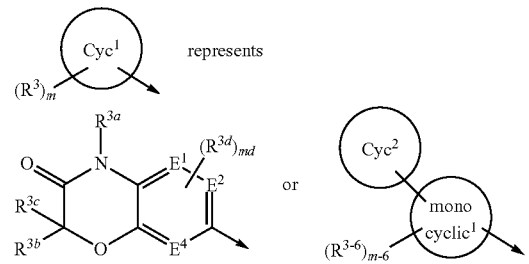

wherein all symbols have the same meanings as described in the above item (7).

(9) The compound according to any one of the above item (1) to (8), wherein

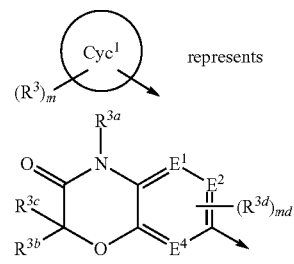

wherein all the symbols have the same meanings as described in the above item (7).

(10) The compound according to any one of the above item (1) to (8), wherein

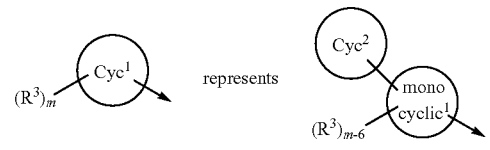

wherein all the symbols have the same meanings as described in the above item (7).

(11) The compound according to any one of the above item (1) to (8) or (10), wherein monocyclic¹ represents 6-membered mono-cyclic aromatic ring having 0 to 2 nitrogen atom and Cyc² represents nitrogen-containing 5- to 6-membered mono-cyclic aromatic heterocyclic ring having 1 to 3 heteroatoms independently selected from nitrogen, oxygen and sulfur, which may be substituted with 1 to 3 groups selected from halogen, cyano, hydroxy and C1-4 alkyl which may be substituted with 1 to 3 groups selected from halogen and hydroxy.

(12) The compound according to any one of the above item (1) to (8), (10), or (11), wherein monocyclic¹ represents benzene or pyridine.

(13) The compound according to the above item (1), wherein the compound is selected from the group consisting of (1) 4-Cyclopropyl-7-((1-(cyclopropylmethyl)-1H-imidazo[4,5-c]pyridin-6-yl)amino)-2H-benzo[b][1,4]oxazin-3(4H)-one,
(2) 7-((1-(Cyclopropylmethyl)-1H-imidazo[4,5-b]pyrazin-6-yl)amino)-4-methyl-2H-benzo[b][1,4]oxazin-3(4H)-one,
(3) 6-((1-(Cyclopropylmethyl)-1H-imidazo[4,5-b]pyrazin-6-yl)amino)-3-methylbenzo[d]oxazol-2(3H)-one,
(4) 7-((9-(Cyclopropylmethyl)-9H-purin-2-yl)amino)-4-(2-methoxyethyl)-2H-benzo[b][1,4]oxazin-3(4H)-one,
(5) 7-((1-((3,3-Difluorocyclobutyl)methyl)-5-fluoro-1H-benzo[d]imidazol-6-yl)amino)-4-methyl-2H-pyrido[3,2-b][1,4]oxazin-3(4H)-one,
(6) 6-((1-((3,3-Difluorocyclobutyl)methyl)-4-methyl-1H-imidazo[4,5-c]pyridin-6-yl)amino)-3-methylbenzo[d]oxazol-2(3H)-one,
(7) 7-((1-(2-Cyclopropylethyl)-5-fluoro-1H-benzo[d]imidazol-6-yl)amino)-4-methyl-2H-pyrido[3,2-b][1,4]oxazin-3(4H)-one,
(8) 7-((1-(Cyclopropylmethyl)-5-fluoro-4-methyl-1H-benzo[d]imidazol-6-yl)amino)-4-methyl-2H-pyrido[3,2-b][1,4]oxazin-3(4H)-one,
(9) 7-((1-(Cyclopropylmethyl)-5-fluoro-4-methyl-1H-benzo[d]imidazol-6-yl)amino)-4-methyl-2H-pyrido[4,3-b][1,4]oxazin-3(4H)-one,
(10) N-(6-(1H-Imidazol-1-yl)pyridin-3-yl)-1-(cyclopropylmethyl)-5-fluoro-4-methyl-1H-benzo[d]imidazol-6-amine,
(11) 1-(Cyclopropylmethyl)-4,5-difluoro-N-(3-fluoro-4-(1H-imidazol-1-yl)phenyl)-1H-benzo[d]imidazol-6-amine,
(12) 7-((3-(Cyclopropylmethyl)-3H-imidazo[4,5-b]pyridin-5-yl)amino)-1-methyl-1H-pyrido[2,3-b][1,4]oxazin-2(3H)-one,
(13) 7-((1-(Cyclopropylmethyl)-4-methyl-1H-imidazo[4,5-c]pyridin-6-yl)amino)-4-methyl-2H-benzo[b][1,4]oxazin-3(4H)-one,
(14) 7-((1-Butyl-4-methyl-1H-imidazo[4,5-c]pyridin-6-yl)amino)-4-methyl-2H-benzo[b][1,4]oxazin-3(4H)-one,
(15) 7-((1-(Cyclopropylmethyl)-4-methyl-1H-imidazo[4,5-c]pyridin-6-yl)amino)-4-methyl-2H-pyrido[3,2-b][1,4]oxazin-3(4H)-one,
(16) 6-((1-(Cyclopropylmethyl)-4-methyl-1H-imidazo[4,5-c]pyridin-6-yl)amino)-1-methyl-1H-pyrido[2,3-b][1,4]oxazin-2(3H)-one,
(17) 7-((9-(Cyclopropylmethyl)-6-methyl-9H-purin-2-yl)amino)-4-ethyl-2H-benzo[b][1,4]oxazin-3(4H)-one,
(18) 6-((3-(Cyclopropylmethyl)-7-(trifluoromethyl)-3H-imidazo[4,5-b]pyridin-5-yl)amino)-1-methyl-1H-pyrido[2,3-b][1,4]oxazin-2(3H)-one,
(19) N-(5-(1H-Imidazol-1-yl)pyridin-2-yl)-3-(cyclopropylmethyl)-7-methyl-3H-imidazo[4,5-b]pyridin-5-amine,
(20) N-(6-(1H-Imidazol-1-yl)pyridin-3-yl)-3-(cyclopropylmethyl)-7-methyl-3H-imidazo[4,5-b]pyridin-5-amine,
(21) 6-((3-(Cyclopropylmethyl)-7-methyl-3H-imidazo[4,5-b]pyridin-5-yl)amino)-1-methyl-1H-pyrido[2,3-b][1,4]oxazin-2(3H)-one and
(22) 6-Chloro-7-((3-(cyclopropylmethyl)-7-methyl-3H-imidazo[4,5-b]pyridin-5-yl)amino)-4-methyl-2H-benzo[b][1,4]oxazin-3(4H)-one.

(14) A gamma-aminobutyric acid A receptor subunit alpha 5 (GABA$_A$ α5) negative allosteric modulator comprising the compound represented by formula (I):

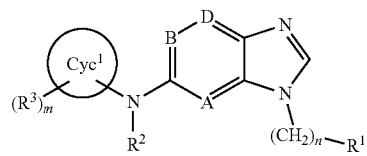

wherein A represents CR$^4$ or N;
B represents CR$^5$ or N;
D represents CR$^6$ or N;
Cyc$^1$ represents a (1) 5- to 15-membered mono-, bi- or tri-cyclic aromatic carbocyclic ring which may be partially saturated or (2) 5- to 15-membered mono-, bi- or tri-cyclic aromatic heterocyclic ring having 1 to 5 heteroatoms independently selected from nitrogen, oxygen and sulfur, which may be partially saturated;
R$^1$ represents (1) 3- to 5-membered cycloalkyl wherein one carbon atom may be replaced by oxygen, which may be substituted with one or more groups independently selected from halogen and C1-4 alkyl which may be substituted with halogen or (2) C1-4 alkyl which may be substituted with halogen;
R$^2$ represents hydrogen or C1-4 alkyl;
R$^3$ represents (1) oxo, (2) halogen, (3) cyano, (4) hydroxy, (5) C1-6 alkyl which may be substituted with R$^7$, (6) C1-6 alkoxy which may be substituted with R$^7$, (7) 3- to 5-membered cycloalkyl wherein one carbon atom may be replaced by oxygen, which may be substituted with R$^8$, (8) 5- to 12-membered mono- or bi-cyclic aromatic carbocyclic ring which may be partially or fully saturated and may be substituted with R$^8$ or (9) 5- to 12-membered mono- or bi-cyclic aromatic heterocyclic ring having 1 to 5 heteroatoms independently selected from nitrogen, oxygen and sulfur, which may be partially or fully saturated and may be substituted with R$^8$;
R$^4$ represents hydrogen or halogen;
R$^5$ represents (1) hydrogen, (2) halogen, (3) hydroxy, (4) cyano, (5) C1-6 alkyl which may be substituted with R$^9$, (6) C2-6 alkenyl which may be substituted with R$^9$, (7) C1-6 alkoxy which may be substituted with R$^9$, (8) C1-6 alkylcarbonyl which may be substituted with R$^9$ or (9) 3- to 5-membered cycloalkyl wherein one carbon atom may be replaced by oxygen, which may be substituted with R$^9$;
R$^6$ represents hydrogen, halogen or C1-4 alkyl which may be substituted with halogen;
R$^7$ represents (1) halogen, (2) hydroxy, (3) C1-4 alkoxy or (4) 3- to 5-membered cycloalkyl wherein one carbon atom may be replaced by oxygen, which may be substituted with one or more groups independently selected from halogen and hydroxy;
R$^8$ represents (1) oxo, (2) halogen, (3) cyano, (4) hydroxy, (5) C1-6 alkyl which may be substituted with one or more groups independently selected from halogen and hydroxy or (6) 3- to 5-membered cycloalkyl which may be substituted with one or more groups independently selected from halogen and hydroxy;
R$^9$ represents halogen or hydroxy;
n represents an integer of 0 to 2; and
m represents an integer of 0 to 7, wherein when m represents an integer of 2 to 7, each R$^3$ may be same or different;
with the proviso that when A is CH, B is N, D is CH, n is 1, R$^1$ is cyclopropyl and R$^2$ is hydrogen, then Cyc$^1$ is not benzene, pyridine, pyrazole or benzodioxole, a pharmaceutically acceptable salt thereof, an N-oxide thereof, a solvate thereof or a prodrug thereof, as an active ingredient.

(15) A pharmaceutical composition comprising the compound according to any one of the above item (1) to (13), a pharmaceutically acceptable salt thereof, an N-oxide thereof, a solvate thereof or a prodrug thereof as an active ingredient.

(16) The pharmaceutical composition according to the above item (15), which is a GABA$_A$ α5 negative allosteric modulator.

(17) The pharmaceutical composition according to the above item (16), which is an agent for the prevention and/or treatment of a disease which is related to the GABA$_A$ α5.

(18) The pharmaceutical composition according to the above item (17), wherein the disease which is related to the GABA$_A$ α5 is acute and/or chronic neurological disorders; cognitive disorders; Alzheimer's disease; memory deficits; mild cognitive impairment (MCI); schizophrenia; positive, negative and/or cognitive symptoms associated with schizophrenia; bipolar disorders; autism; Down syndrome; neurofibromatosis type I; sleep disorders; disorders of circadian rhythms; amyotrophic lateral sclerosis (ALS); dementia caused by AIDS; head trauma; Huntington's disease; Pick's disease; Creutzfeld Jakob disease; psychotic disorders; substance-induced psychotic disorder; anxiety disorders; generalized anxiety disorder; panic disorder; delusional disorder; obsessive/compulsive disorders; acute stress disorder; drug addictions; movement disorders; Parkinson's disease; restless leg syndrome; cognition deficiency disorders; multi-infarct dementia; mood disorders; depression; neuropsychiatric conditions; psychosis; attention-deficit/hyperactivity disorder; neuropathic pain; stroke; multiple sclerosis (MS); acute meningitis; alcoholism; Fetal Alcohol Syndrome; attentional disorders; CNS conditions occurring after stroke; or need for cognition enhancement.

(19) The pharmaceutical composition according to the above item (18), wherein the disease which is related to the GABA$_A$ α5 is Alzheimer's disease, schizophrenia, Down syndrome or CNS conditions occurring after stroke.

(20) A medicament comprising a combination of the compound according to any one of the above item (1) to (13), a pharmaceutically acceptable salt thereof, an N-oxide thereof, a solvate thereof or a prodrug thereof with a acetylcholinesterase inhibitor and/or N-methyl-D-aspartate (NMDA) receptor antagonist.

(21) A method of preventing and/or treating a disease which is related to the GABA$_A$ α5 comprising administering an effective amount of the compound according to any one of the above item (1) to (13), a pharmaceutically acceptable salt thereof, an N-oxide thereof, a solvate thereof or a prodrug thereof to a mammal.

(22) The compound according to any one of the above item (1) to (13), a pharmaceutically acceptable salt thereof, an N-oxide thereof, a solvate thereof or a prodrug thereof for use in the prevention and/or treatment of a disease which is related to the GABA$_A$ α5.

(23) Use of the compound according to any one of the above item (1) to (13), a pharmaceutically acceptable salt thereof, an N-oxide thereof, a solvate thereof or a prodrug thereof in the manufacture of a medicament for the prevention and/or treatment of a disease which is related to the GABA$_A$ α5.

(24) A compound represented by formula (I):

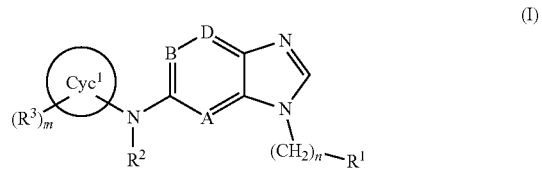

wherein A represents CR$^4$ or N;
B represents CR$^5$ or N;
D represents CR$^6$ or N;
Cyc$^1$ represents a (1) 5- to 15-membered mono-, bi- or tri-cyclic aromatic carbocyclic ring which may be partially saturated or (2) 5- to 15-membered mono-, bi- or tri-cyclic aromatic heterocyclic ring having 1 to 5 heteroatoms independently selected from nitrogen, oxygen and sulfur, which may be partially saturated;
R$^1$ represents (1) 3- to 5-membered cycloalkyl wherein one carbon atom may be replaced by oxygen, which may be substituted with one or more groups independently selected from halogen and C1-4 alkyl which may be substituted with halogen or (2) C1-4 alkyl which may be substituted with halogen;
R$^2$ represents hydrogen or C1-4 alkyl;
R$^3$ represents (1) oxo, (2) halogen, (3) cyano, (4) hydroxy, (5) C1-6 alkyl which may be substituted with R$^7$, (6) C1-6 alkoxy which may be substituted with R$^7$, (7) 3- to 5-membered cycloalkyl wherein one carbon atom may be replaced by oxygen, which may be substituted with R$^8$, (8) 5- to 12-membered mono- or bi-cyclic aromatic carbocyclic ring which may be partially or fully saturated and may be substituted with R$^8$ or (9) 5- to 12-membered mono- or bi-cyclic aromatic heterocyclic ring having 1 to 5 heteroatoms independently selected from nitrogen, oxygen and sulfur, which may be partially or fully saturated and may be substituted with R$^8$;
R$^4$ represents hydrogen or halogen;
R$^5$ represents (1) hydrogen, (2) halogen, (3) hydroxy, (4) cyano, (5) C1-6 alkyl which may be substituted with R$^9$, (6) C2-6 alkenyl which may be substituted with R$^9$, (7) C1-6 alkoxy which may be substituted with R$^9$, (8) C1-6 alkylcarbonyl which may be substituted with R$^9$ or (9) 3- to 5-membered cycloalkyl wherein one carbon atom may be replaced by oxygen, which may be substituted with R$^9$;
R$^6$ represents hydrogen, halogen or C1-4 alkyl which may be substituted with halogen;
R$^7$ represents (1) halogen, (2) hydroxy, (3) C1-4 alkoxy or (4) 3- to 5-membered cycloalkyl wherein one carbon atom may be replaced by oxygen, which may be substituted with one or more groups independently selected from halogen and hydroxy;
R$^8$ represents (1) oxo, (2) halogen, (3) cyano, (4) hydroxy or (5) C1-6 alkyl which may be substituted with one or more groups independently selected from halogen and hydroxy;
R$^9$ represents halogen or hydroxy;
n represents an integer of 1 to 2; and
m represents an integer of 0 to 7, wherein when m represents an integer of 2 to 7, each R$^3$ may be same or different;
with the proviso that when A is CH, B is N, D is CH, n is 1, R$^1$ is cyclopropyl and R$^2$ is hydrogen, then Cyc$^1$ is not benzene, pyridine, pyrazole or benzodioxole; or
a pharmaceutically acceptable salt thereof, an N-oxide thereof, a solvate thereof or a prodrug thereof.

BRIEF DESCRIPTION OF THE DRAWINGS

FIG. 1 shows the effect of example 160 on the rat Novel Object Recognition test. In the FIG. 1, the data represents mean+SEM and ** indicates P<0.01.

MODE FOR CARRYING OUT THE INVENTION

The present invention will be explained in detail below.

In the present invention, C1-4 alkyl includes, for example, methyl, ethyl, n-propyl, isopropyl, n-butyl, sec-butyl and tert-butyl.

In the present invention, C1-6 alkyl includes, for example, methyl, ethyl, propyl, butyl, pentyl, hexyl and isomeric groups thereof.

In the present invention, C2-4 alkenyl includes, for example, ethenyl, n-propenyl, iso-propenyl, n-butenyl, sec-butenyl, t-butenyl and isomeric groups thereof.

In the present invention, C2-6 alkenyl includes, for example, ethenyl, propenyl, butenyl, pentenyl, hexenyl and isomeric groups thereof.

In the present invention, C1-4 alkoxy includes, for example, methoxy, ethoxy, propoxy, butoxy and isomeric groups thereof.

In the present invention, C1-6 alkoxy includes, for example, methoxy, ethoxy, propoxy, butoxy, pentyloxy, hexyloxy and isomeric groups thereof.

In the present invention, C1-4 alkyl-carbonyl means a radical of the formula: —C(O)—C1-4 alkyl, wherein C1-4 alkyl has the same meaning as described above.

In the present invention, C1-6 alkyl-carbonyl means a radical of the formula: —C(O)—C1-6 alkyl, wherein C1-6 alkyl has the same meaning as described above.

In the present invention, "3- to 5-membered cycloalkyl wherein one carbon atom may be replaced by oxygen" includes, for example, cyclopropyl, cyclobutyl, cyclopentyl, oxiranyl, oxetanyl, tetrahydrofuranyl and the like.

In the present invention, "—$(CH_2)_p$-(3- to 5-membered cycloalkyl), wherein one carbon atom in cycloalkyl may be replaced by oxygen and p represents 0 or 1" includes, for example, cyclopropyl, cyclobutyl, cyclopentyl, oxiranyl, oxetanyl, tetrahydrofuranyl, —$CH_2$— cyclopropyl, —$CH_2$— cyclobutyl, —$CH_2$— cyclopentyl, —$CH_2$— oxiranyl, —$CH_2$— oxetanyl, —$CH_2$— tetrahydrofuranyl and the like.

In the present invention, halogen includes, for example, fluorine, chlorine, bromine, iodine and the like, preferably fluorine or chlorine.

In the present invention, "C1-4 alkyl which may be substituted with halogen" means both C1-4 alkyl and C1-4 alkyl substituted with halogen (C1-4 haloalkyl). "C1-4 alkyl which may be substituted with halogen" includes, for example, C1-4 alkyl which may be substituted with one to five halogen. Representative examples of C1-4 haloalkyl include fluoromethyl, difluoromethyl, trifluoromethyl, fluoroethyl, difluoroethyl, 1,2-dichloroethyl, trichloroethyl and the like.

In the present invention, "5- to 15-membered mono-, bi- or tri-cyclic aromatic carbocyclic ring which may be partially saturated" includes, for example, cyclopentene, cyclohexene, cycloheptene, cyclooctene, cyclopentadiene, cyclohexadiene, cycloheptadiene, cyclooctadiene, benzene, pentalene, azulene, indene, indan, naphthalene, dihydronaphthalene, tetrahydronaphthalene, heptalene, biphenylene, as-indacene, s-indacene, acenaphthylene, acenaphthene, fluorene, phenalene, phenanthrene, anthracene and the like.

In the present invention, "5- to 15-membered mono-, bi- or tri-cyclic aromatic heterocyclic ring having 1 to 5 heteroatoms independently selected from nitrogen, oxygen and sulfur, which may be partially saturated" includes, for example, tetrazoline, tetrazole, triazoline, dihydrofurazan, dihydrooxadiazole, dihydrothiadiazole, triazole, furazan, oxadiazole, thiadiazole, imidazoline, pyrazoline, dihydrooxazole, dihydroisoxazole, dihydrothiazole, dihydroisothiazole, imidazole, pyrazole, oxazole, isoxazole, thiazole, isothiazole, pyrroline, dihydrofuran, dihydrothiophene, pyrrole, furan, thiophene, oxadiazine, thiadiazine, dihydrooxadiazine, dihydrothiadiazine, oxazine, thiazine, dihydropyrazine, tetrahydropyrazine, dihydropyrimidine, tetrahydropyrimidine, dihydropyridazine, tetrahydropyridazine, dihydrooxazine, dihydrothiazine, pyrazine, pyrimidine, pyridazine, pyran, thiopyran, dihydropyridine, tetrahydropyridine, dihydropyran, dihydrothiopyran, pyridine, oxadiazepine, thiadiazepine, dihydrooxadiazepine, tetrahydrooxadiazepine, dihydrothiadiazepine, tetrahydrothiadiazepine, diazepine, oxazepine, thiazepine, dihydrodiazepine, tetrahydrodiazepine, dihydrooxazepine, tetrahydrooxazepine, dihydrothiazepine, tetrahydrothiazepine, azepine, oxepine, thiepine, dihydroazepine, tetrahydroazepine, dihydrooxepine, tetrahydrooxepine, dihydrothiepine, tetrahydrothiepine, purine, benzofurazan, benzothiadiazole, benzotriazole, dihydroindazole, dihydrobenzoxazole, dihydrobenzothiazole, dihydrobenzimidazole, benzodioxole, benzodithiolane, indazole, benzoxazole, benzothiazole, benzimidazole, indolizine, indoline, isoindoline, dihydrobenzofuran, dihydroisobenzofuran, dihydrobenzothiophene, dihydroisobenzothiophene, indole, isoindole, benzofuran, isobenzofuran, benzothiophene, isobenzothiophene, pyrrolepyridine, imidazopyridine, pyrazinomorpholine, pteridine, dithianaphthalene, dihydrophthalazine, tetrahydrophthalazine, dihydronaphthyridine, tetrahydronaphthyridine, dihydroquinoxaline, tetrahydroquinoxaline, dihydroquinazoline, tetrahydroquinazoline, dihydrocinnoline, tetrahydrocinnoline, benzoxathiane, dihydrobenzoxazine, dihydropyridooxazine, dihydrobenzothiazine, benzodioxane, benzodithiane, phthalazine, naphthyridine, quinoxaline, quinazoline, cinnoline, quinolizine, chromene, dihydroquinoline, tetrahydroquinoline, dihydroisoquinoline, tetrahydroisoquinoline, chroman, quinoline, isoquinoline, benzoxadiazepine, benzothiadiazepine, benzoxazepine, benzothiazepine, benzodiazepine, dihydrobenzodiazepine, tetrahydrobenzodiazepine, benzodioxepane, dihydrobenzoxazepine, tetrahydrobenzoxazepine, benzoxepine, benzothiepine, benzazepine, dihydrobenzazepine, tetrahydrobenzazepine, perimidine, beta-carboline, dihydrocarbazole, tetrahydrocarbazole, dihydrodibenzofuran, dihydrodibenzothiophene, tetrahydrodibenzofuran, tetrahydrodibenzothiophene, carbazole, dibenzofuran, dibenzothiophene, phenothiazine, phenoxazine, phenoxathiin, thianthrene, phenazine, phenanthroline, xanthene, dihydroacridine, tetrahydroacridine, acridine, phenanthridine, dihydrobenzoimidazooxazine (2,4-dihydro-1H-benzo[b]imidazo[1,2-d][1,4]oxazine) and the like.

In the present invention, "5- to 12-membered mono- or bi-cyclic aromatic carbocyclic ring which may be partially or fully saturated" includes, for example, cyclopentane, cyclopentene, cyclohexene, cycloheptene, cyclooctene, cyclopentadiene, cyclohexadiene, cycloheptadiene, cyclooctadiene, benzene, pentalene, perhydropentalene, azulene, perhydroazulene, indene, perhydroindene, indan, naphthalene, dihydronaphthalene, tetrahydronaphthalene, perhydronaphthalene, heptalene, perhydroheptalene, cyclohexane, cycloheptane, cyclooctane and the like.

In the present invention, "5- to 12-membered mono- or bi-cyclic aromatic heterocyclic ring having 1 to 5 heteroatoms independently selected from nitrogen, oxygen and sulfur, which may be partially or fully saturated", includes, for example, pyrrole, imidazole, triazole, tetrazole, pyrazole, pyridine, pyrazine, pyrimidine, pyridazine, azepine, diazepine, furan, pyran, oxepine, thiophene, thiopyran, thiepine, oxazole, isoxazole, thiazole, isothiazole, furazan, oxadiazole, oxazine, oxadiazine, oxazepine, oxadiazepine, thiadiazole, thiazine, thiadiazine, thiazepine, thiadiazepine, indole, isoindole, indolizine, benzofuran, isobenzofuran, benzothiophene, isobenzothiophene, dithianaphthalene, indazole, quinoline, isoquinoline, quinolizine, purine, phthalazine, pteridine, naphthyridine, quinoxaline, quinazoline, cinnoline, benzoxazole, benzothiazole, benzimidazole, chromene, benzoxepine, benzoxazepine, benzoxadiazepine, benzothiepine, benzothiazepine, benzothiadiazepine, benzazepine, benzodiazepine, benzofurazan, benzothiadiazole, benzotriazole, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, dihydrofuran, tetrahydrofuran, dihydropyran, tetrahydropyran, dihydrooxepine, tetrahydrooxepine, perhydrooxepine, dihydrothiophene, tetrahydrothiophene, dihydrothiopyran, tetrahydrothiopyran, dihydrothiepine, tetrahydrothiepine, perhydrothiepine, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, benzoxathiane, dihydrobenzoxazine, dihydrobenzothiazine, pyrazinomorpholine, dihydrobenzoxazole, perhydrobenzoxazole, dihydrobenzothiazole, perhydrobenzothiazole, dihydrobenzimidazole, perhydrobenzimidazole, dihydrobenzazepine, tetrahydrobenzazepine, dihydrobenzodiazepine, tetrahydrobenzodiazepine, benzodioxepane, dihydrobenzoxazepine, tetrahydrobenzoxazepine, dioxolane, dioxane, dithiolane, dithiane, benzodioxole, benzodioxane, chroman, benzodithiolane, benzodithiane, dihydropyrroloimidazole, imidazopyrimidine and the like.

In the present invention, "5- to 6-membered mono-cyclic aromatic heterocyclic ring having 1 to 3 heteroatoms independently selected from nitrogen, oxygen and sulfur, which may be partially or fully saturated" includes, for example, pyrrole, imidazole, triazole, pyrazole, pyridine, pyrazine, pyrimidine, pyridazine, furan, pyran, thiophene, thiopyran, oxazole, isoxazole, thiazole, isothiazole, furazan, oxadiazole, oxazine, oxadiazine, thiadiazole, thiazine, thiadiazine, pyrroline, pyrrolidine, imidazoline, imidazolidine, triazoline, triazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydrofuran, tetrahydrofuran, dihydropyran, tetrahydropyran, dihydrothiophene, tetrahydrothiophene, dihydrothiopyran, tetrahydrothiopyran, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrothiadiazole, tetrahydrothiadiazole (thiadiazolidine), dihydrothiazine, tetrahydrothiazine, dihydrothiadiazine, tetrahydrothiadiazine, morpholine, thiomorpholine, oxathiane, dioxolane, dioxane, dithiolane, dithiane and the like.

In the present invention, "8- to 12-membered bicyclic aromatic heterocyclic ring having 1 to 5 heteroatoms independently selected from nitrogen, oxygen and sulfur, which may be partially or fully saturated" includes, for example, indole, isoindole, indolizine, benzofuran, isobenzofuran, benzothiophene, isobenzothiophene, dithianaphthalene, indazole, quinoline, isoquinoline, quinolizine, purine, phthalazine, pteridine, naphthyridine, quinoxaline, quinazoline, cinnoline, benzoxazole, benzothiazole, benzimidazole, chromene, benzoxepine, benzoxazepine, benzoxadiazepine, benzothiepine, benzothiazepine, benzothiadiazepine, benzazepine, benzodiazepine, benzofurazan, benzothiadiazole, benzotriazole, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, benzoxathiane, dihydrobenzoxazine, dihydrobenzothiazine, pyrazinomorpholine, dihydrobenzoxazole, perhydrobenzoxazole, dihydrobenzothiazole, perhydrobenzothiazole, dihydrobenzimidazole, perhydrobenzimidazole, dihydrobenzazepine, tetrahydrobenzazepine, dihydrobenzodiazepine, tetrahydrobenzodiazepine, benzodioxepane, dihydrobenzoxazepine, tetrahydrobenzoxazepine, benzodioxole, benzodioxane, chroman, benzodithiolane, benzodithiane, dihydropyrroloimidazole, imidazopyrimidine and the like.

In the present invention, "6-membered mono-cyclic aromatic ring having 0 to 2 nitrogen atom" includes, for example, benzene, pyridine, pyrazine, pyrimidine, pyridazine.

In the present invention, "5- to 7-membered mono-cyclic aromatic carbocyclic ring which is partially or fully saturated" includes, for example, cyclopentane, cyclohexane, cycloheptane, cyclopentene, cyclohexene, cycloheptene, cyclopentadiene, cyclohexadiene, cycloheptadiene and the like.

In the present invention, "5- to 7-membered mono-cyclic aromatic carbocyclic ring which may be partially saturated" includes, for example, cyclopentene, cyclohexene, cycloheptene, cyclopentadiene, cyclohexadiene, cycloheptadiene, benzene and the like.

In the present invention, "5- to 7-membered mono-cyclic aromatic heterocyclic ring having 1 to 3 heteroatoms independently selected from nitrogen and oxygen, which is partially or fully saturated" includes, for example, pyrroline, pyrrolidine, imidazoline, imidazolidine, triazoline, triazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, dihydrofuran, tetrahydrofuran, dihydropyran, tetrahydropyran, dihydrooxepine, tetrahydrooxepine, perhydrooxepine, dihydrooxazole, tetrahydrooxazole (oxazolidine), dihydroisoxazole, tetrahydroisoxazole (isoxazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, morpholine, dioxolane, dioxane and the like.

In the present invention, "5- to 7-membered mono-cyclic aromatic heterocyclic ring having 1 to 3 heteroatoms independently selected from nitrogen, oxygen and sulfer, which may be partially saturated" includes, for example, pyrroline, dihydrofuran, dihydrothiophene, pyrrole, furan, thiophene, imidazoline, pyrazoline, dihydrooxazole, dihydroisoxazole, dihydrothiazole, dihydroisothiazole, imidazole, pyrazole, oxazole, isoxazole, triazole, isothiazole, triazoline, dihydrofurazan, dihydrooxadiazole, dihydrothiadiazole, triazole, furazan, oxadiazole, thiadiazole, pyran, thiopyran, dihydropyridine, tetrahydropyridine, dihydropyran, dihydrothiopyran, pyridine, oxazine, thiazine, dihydropyrazine, tetrahydropyrazine, dihydropyrimidine, tetrahydropyrimidine, dihydropyridazine, tetrahydropyridazine, dihydrooxazine, dihydrothiazine, pyrazine, pyrimidine, pyridazine, oxadiazine, thiadiazine, dihydrooxadiazine, dihydrothiadiazine, azepine, oxepine, thiepine, dihydroazepine, tetrahydroazepine, dihydrooxepine, tetrahydrooxepine, dihydrothiepine, tetrahydrothiepine, diazepine, oxazepine, thiazepine, dihydrodiazepine, tetrahydrodiazepine, dihydrooxazepine, tetrahydrooxazepine, dihydrothiazepine, tetrahydrothiazepine, oxadiazepine, thiadiazepine, dihydrooxadiazepine, tetrahydrooxadiazepine, dihydrothiadiazepine, tetrahydrothiadiazepine and the like.

In the present invention, "8- to 10-membered bicyclic aromatic heterocyclic ring having 1 to 3 heteroatoms independently selected from nitrogen and oxygen, which is partially or fully saturated" includes, for example, indoline, isoindoline, dihydrobenzofuran, perhydrobenzofuran, perhydroisobenzofuran, dihydroindazole, perhydroindazole, dihydrobenzoxazole, perhydrobenzoxazole, dihydrobenzimidazole, perhydrobenzimidazole, quinolizine, chromene, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, dihydrobenzoxazine, pyrazinomorpholine, benzodioxane, chroman, dihydroimidazooxazine and the like.

In the present invention, "nitrogen-containing 5- to 7-membered mono-cyclic aromatic heterocyclic ring having 1 to 3 heteroatoms independently selected from nitrogen and oxygen, which may be partially or fully saturated" includes, for example, pyrrole, imidazole, triazole, pyrazole, pyridine, pyrazine, pyrimidine, pyridazine, oxazole, isoxazole, furazan, oxadiazole, azepine, diazepine, oxazine, oxadiazine, oxazepine, oxadiazepine, pyrroline, pyrrolidine, imidazoline, imidazolidine, triazoline, triazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, dihydrooxazole, tetrahydrooxazole (oxazolidine), dihydroisoxazole, tetrahydroisoxazole (isoxazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, morpholine and the like.

In the present invention, "nitrogen-containing 5- to 6-membered mono-cyclic aromatic heterocyclic ring having 1 to 3 heteroatoms independently selected from nitrogen, oxygen and sulfer" includes, for example, pyrrole, imidazole, triazole, pyrazole, pyridine, pyrazine, pyrimidine, pyridazine, oxazole, isoxazole, thiazole, isothiazole, furazan, oxadiazole, thiadiazole and the like.

Preferably, n represents 0 or 1.

Preferably, $R^1$ represents (1) cyclopropyl, cyclobutyl, oxetanyl or tetrahydrofuranyl, any of which may be substituted with 1 to 5 groups selected from halogen and C1-4 alkyl which may be substituted with 1 to 3 halogen, or (2) n-propyl, isopropyl, butyl, sec-butyl or tert-butyl, any of which may be substituted with 1 to 3 halogen, more preferably cyclopropyl, cyclobutyl, oxetanyl, tetrahydrofuranyl, n-propyl or isopropyl, any of which may be substituted with 1 to 3 halogen and especially preferably cyclopropyl, cyclobutyl, n-propyl or isopropyl.

Preferably, $R^2$ represents hydrogen or methyl, more preferably hydrogen.

Preferably, $R^3$ represents (1) oxo, (2) halogen, (3) cyano, (4) hydroxy, (5) C1-6 alkyl which may be substituted with 1 to 5 groups selected from halogen, hydroxy and C1-4 alkoxy, (6) C1-6 alkoxy which may be substituted with 1 to 5 groups selected from halogen, hydroxy and C1-4 alkoxy, (7) —$(CH_2)_p$-(3- to 5-membered cycloalkyl), wherein one carbon atom in cycloalkyl may be replaced by oxygen and p represents 0 or 1, which may be substituted with 1 to 3 groups selected from halogen and hydroxy, (8) benzene which may be substituted with 1 to 3 groups selected from halogen, cyano, hydroxy and C1-4 alkyl which may be substituted with 1 to 3 groups selected from halogen and hydroxy, (9) 5- to 6-membered mono-cyclic aromatic heterocyclic ring having 1 to 3 heteroatoms independently selected from nitrogen, oxygen and sulfur, which may be partially or fully saturated and may be substituted with 1 to 3 groups selected from oxo, halogen, cyano, hydroxy and C1-4 alkyl which may be substituted with 1 to 3 groups selected from halogen and hydroxy or (10) 8- to 12-membered bicyclic aromatic heterocyclic ring having 1 to 5 heteroatoms independently selected from nitrogen, oxygen and sulfur, which may be partially or fully saturated and may be substituted with 1 to 5 groups selected from oxo, halogen, cyano, hydroxy and C1-4 alkyl which may be substituted with 1 to 3 groups selected from halogen and hydroxy.

Preferably, "(9) 5- to 6-membered mono-cyclic aromatic heterocyclic ring having 1 to 3 heteroatoms independently selected from nitrogen, oxygen and sulfur, which may be partially or fully saturated and may be substituted with 1 to 3 groups selected from oxo, halogen, cyano, hydroxy and C1-4 alkyl which may be substituted with 1 to 3 groups selected from halogen and hydroxy" as $R^3$ represents nitrogen-containing 5- to 6-membered mono-cyclic aromatic heterocyclic ring having 1 to 3 heteroatoms independently selected from nitrogen, oxygen and sulfur, which may be partially or fully saturated (e.g. pyrrole, imidazole, triazole, pyrazole, pyridine, pyrazine, pyrimidine, pyridazine, oxazole, isoxazole, thiazole, isothiazole, furazan, oxadiazole, oxazine, oxadiazine, thiadiazole, thiazine, thiadiazine, pyrroline, pyrrolidine, imidazoline, imidazolidine, triazoline, triazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydrooxazole, tetrahydrooxazole (oxazolidine), dihydroisoxazole, tetrahydroisoxazole (isoxazolidine), dihydrothiazole, tetrahydrothiazole (triazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrothiadiazole, tetrahydrothiadiazole (thiadiazolidine), dihydrothiazine, tetrahydrothiazine, dihydrothiadiazine, tetrahydrothiadiazine, morpholine, thiomorpholine, azabicyclo[2.2.1]heptane, azabicyclo[3.1.1]heptane, azabicyclo[2.2.2]octane, diazabicyclo[2.2.2]octane) and may be substituted with 1 to 3 groups selected from oxo, halogen, cyano, hydroxy and C1-4 alkyl which may be substituted with 1 to 3 groups selected from halogen and hydroxy, more preferably nitrogen-containing 5- to 6-membered mono-cyclic aromatic heterocyclic ring having 1 to 3 heteroatoms independently selected from nitrogen, oxygen and sulfur (e.g. pyrrole, imidazole, triazole, pyrazole, oxazole, isoxazole, thiazole, isothiazole, furazan, oxadiazole, thiadiazole, pyridine, pyrazine, pyrimidine, pyridazine), which may be substituted with 1 to 3 groups selected from halogen, cyano, hydroxy and C1-4 alkyl which may be substituted with 1 to 3 groups selected from halogen and hydroxy.

Preferably, "(10) 8- to 12-membered bicyclic aromatic heterocyclic ring having 1 to 5 heteroatoms independently selected from nitrogen, oxygen and sulfur, which may be partially or fully saturated and may be substituted with 1 to 5 groups selected from oxo, halogen, cyano, hydroxy and C1-4 alkyl which may be substituted with 1 to 3 groups selected from halogen and hydroxy" as $R^3$ represents nitrogen-containing 8- to 9-membered bicyclic aromatic heterocyclic ring having 1 to 3 heteroatoms independently selected from nitrogen, oxygen and sulfur, which may be partially or fully saturated (e.g. dihydropyrroloimidazole, indole, isoindole, indolizine, indazole, benzoxazole, benzothiazole, benzimidazole, benzofurazan, benzothiadiazole, benzotriazole, indoline, isoindoline, dihydroindazole, perhydroindazole, dihydrobenzoxazole, perhydrobenzoxazole, dihydrobenzothiazole, perhydrobenzothiazole, dihydrobenzimidazole, perhydrobenzimidazole, imidazopyrimidine) and may be substituted with 1 to 5 groups selected from oxo, halogen, cyano, hydroxy and C1-4 alkyl which may be substituted with 1 to 3 groups selected from halogen and hydroxy, more preferably nitrogen-containing 8- to 9-membered bicyclic aromatic heterocyclic ring having 1 to 3 heteroatoms independently selected from nitrogen, oxygen and sulfur (e.g. indole, isoindole, indazole, benzoxazole, benzothiazole, benzimidazole, benzofurazan, benzothiadiazole, benzotriazole, imidazopyrimidine), which may be substituted with 1 to 3 groups selected from halogen, cyano, hydroxy and C1-4 alkyl which may be substituted with 1 to 3 groups selected from halogen and hydroxy.

Preferably, $R^4$ represents hydrogen or halogen, more preferably hydrogen.

Preferably, $R^5$ represents (1) hydrogen, (2) halogen, (3) hydroxy, (4) cyano, (5) C1-4 alkyl which may be substituted with 1 to 3 groups selected from halogen and hydroxy, (6) C2-4 alkenyl which may be substituted with 1 to 3 groups selected from halogen and hydroxy, (7) C1-4 alkoxy which may be substituted with 1 to 3 groups selected from halogen and hydroxy, (8) C1-4 alkyl-carbonyl which may be substituted with 1 to 3 groups selected from halogen and hydroxy or (9) 3- to 5-membered cycloalkyl wherein one carbon atom may be replaced by oxygen, which may be substituted with 1 to 3 groups selected from halogen and hydroxy, more preferably (1) hydrogen, (2) halogen, (3) hydroxy, (4) cyano, (5) methyl or ethyl, (6) ethenyl, (7) methoxy which may be substituted with halogen or (8) cyclopropyl.

Preferably, $R^6$ represents hydrogen, halogen or methyl which may be substituted with halogen. More preferably, $R^6$ represents halogen or methyl which may be substituted with halogen.

Preferably, 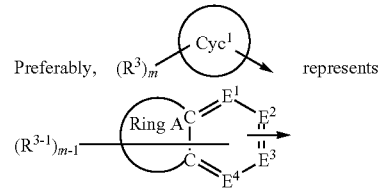 represents wherein $E^1$, $E^2$, $E^3$ and $E^4$ each independently represent a carbon atom or a nitrogen atom, with the proviso that at least two of $E^1$ through $E^4$ are carbon atoms (preferably at least three of $E^1$ through $E^4$ are carbon atoms); Ring A represents (1) 5- to 7-membered mono-cyclic aromatic carbocyclic ring which is partially or fully saturated, (2) 5- to 7-membered mono-cyclic aromatic heterocyclic ring having 1 to 3 heteroatoms independently selected from nitrogen and oxygen, which is partially or fully saturated or (3) 8- to 10-membered bicyclic aromatic heterocyclic ring having 1 to 3 heteroatoms independently selected from nitrogen and oxygen, which is partially or fully saturated; $R^{3-1}$ represents (1) oxo, (2) halogen, (3) cyano, (4) hydroxy, (5) C1-6 alkyl which may be substituted with 1 to 5 groups selected from halogen, hydroxy and C1-4 alkoxy, (6) C1-6 alkoxy which may be substituted with 1 to 5 groups selected from halogen, hydroxy and C1-4 alkoxy, (7) —$(CH_2)_p$-(3- to 5-membered cycloalkyl), wherein one carbon atom in cycloalkyl may be replaced by oxygen and p represents 0 or 1, which may be substituted with 1 to 3 groups selected from halogen and hydroxy; m-1 represents an integer of 0 to 7, wherein when m-1 represents an integer of 2 to 7, each $R^{3-1}$ may be same or different; and the starting point of the arrow is any one of $E^1$ through $E^4$ and the arrow represents a binding position to the $N(R^2)$.

Preferably, Ring A represents 5- to 7-membered mono-cyclic aromatic heterocyclic ring having 1 to 3 heteroatoms independently selected from nitrogen and oxygen, which is partially or fully saturated.

Preferably, $R^{3-1}$ represents (1) oxo, (2) halogen, (3) C1-4 alkyl which may be substituted with 1 to 3 groups selected from halogen, hydroxy and methoxy, (4) —$(CH_2)_p$-(3- to 5-membered cycloalkyl), wherein one carbon atom in cycloalkyl may be replaced by oxygen and p represents 0 or 1.

Preferably, "5- to 7-membered mono-cyclic aromatic heterocyclic ring having 1 to 3 heteroatoms independently selected from nitrogen and oxygen, which is partially or fully saturated" as Ring A represents nitrogen-containing 5- to 6-membered mono-cyclic aromatic ring having 1 to 2 heteroatoms independently selected from nitrogen and oxygen, which is partially or fully saturated (e.g. pyrroline, pyrrolidine, imidazoline, imidazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydrooxazole, tetrahydrooxazole (oxazolidine), dihydroisoxazole, tetrahydroisoxazole (isoxazolidine), dihydrooxazine, tetrahydrooxazine, morpholine and the like), and more preferably morpholine, piperidine, perhydropyrimidine, tetrahydropyrimidine, imidazoline, pyrrolidine, dihydrooxazole, tetrahydrooxazole.

Also preferably, 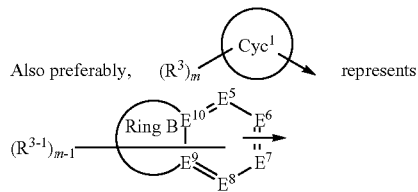 represents

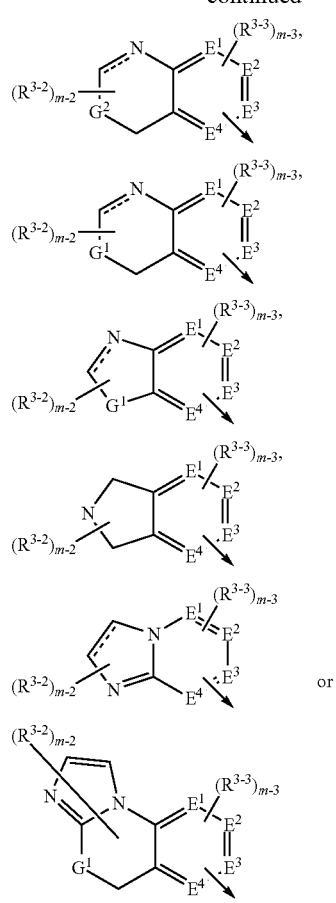

wherein $E^5$, $E^6$, $E^7$, $E^8$, $E^9$ and $E^{10}$ each independently represent a carbon atom or a nitrogen atom, with the proviso that at least four of $E^5$ through $E^{10}$ are carbon atoms and at least one of $E^9$ and $E^{10}$ is a nitrogen atom; Ring B represents nitrogen-containing 5- to 7-membered mono-cyclic aromatic heterocyclic ring having 1 to 3 heteroatoms independently selected from nitrogen and oxygen, which may be partially or fully saturated; the starting point of the arrow is any one of $E^5$ through $E^8$ and the arrow represents a binding position to the $N(R^2)$; and the other symbols have the same meanings as described above and the same preferred definitions as set out above.

More preferably, 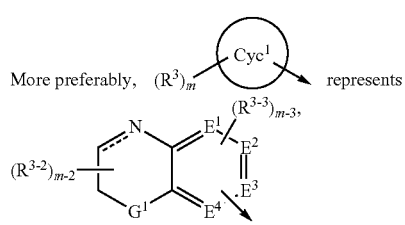 represents wherein $E^1$, $E^2$, $E^3$ and $E^4$ each independently represent a carbon atom or a nitrogen atom, with the proviso that at least three of $E^1$ through $E^4$ are carbon atoms; $G^1$ represents a carbon atom, a nitrogen atom or an oxygen, atom; $G^2$ represents a nitrogen atom or an oxygen atom; $R^{3-2}$ represents (1) oxo, (2) halogen, (3) C1-4 alkyl which may be substituted with 1 to 3 groups selected from halogen, hydroxy and methoxy, (4) —$(CH_2)_p$-(3- to 5-membered cycloalkyl), wherein one carbon atom in cycloalkyl may be replaced by oxygen and p represents 0 or 1; $R^{3-3}$ represents halogen or C1-4 alkyl; m-2 represents an integer of 0 to 5, wherein when m-2 represents an integer of 2 to 5, each $R^{3-2}$ may be same or different; m-3 represents an integer of 0 to 2, wherein when m-3 represents an integer of 2, each $R^{3-3}$ may be same or different; the starting point of the arrow is $E^2$ or $E^3$ and the arrow represents a binding position to the $N(R^2)$; and ═══ represents a single bond or a double bond.

Further preferably, 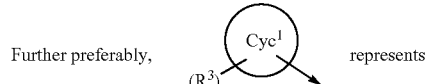 represents

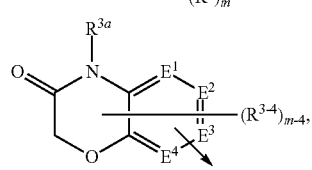

-continued

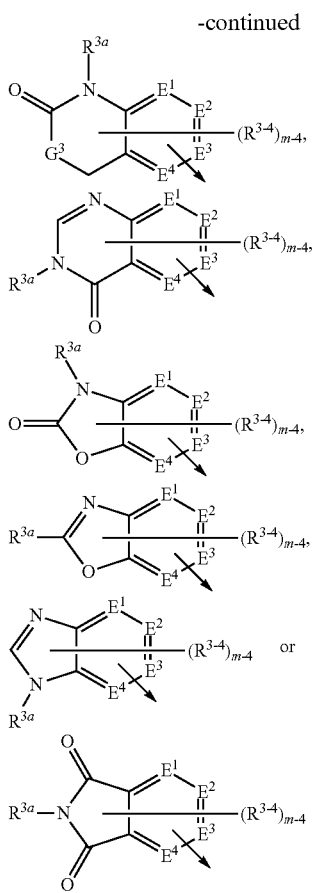

wherein $E^1$, $E^2$, $E^3$ and $E^4$ each independently represent a carbon atom or a nitrogen atom, with the proviso that at least three of $E^1$ through $E^4$ are carbon atoms; $G^3$ represents a carbon atom or a nitrogen atom; $R^{3a}$ represents (1) hydrogen, (2) C1-4 alkyl which may be substituted with 1 to 3 groups selected from halogen, hydroxy and methoxy (preferably (i) C1-4 alkyl, (ii) C1-4 alkyl substituted with 1 to 3 halogen, (iii) C1-4 alkyl substituted with hydroxy or (iv) C1-4 alkyl substituted with methoxy) or (3) —(CH$_2$)$_p$-(3- to 5-membered cycloalkyl), wherein one carbon atom in cycloalkyl may be replaced by oxygen and p represents 0 or 1 (preferably cyclopropyl, cyclobutyl, oxetanyl, —CH$_2$— cyclopropyl, —CH$_2$— cyclobutyl or —CH$_2$— oxetanyl); $R^{3-4}$ represents halogen or C1-4 alkyl; m-4 represents an integer of 0 to 3, wherein when m-4 represents an integer of 2 to 3, each $R^{3-4}$ may be same or different; and the starting point of the arrow is $E^2$ or $E^3$ and the arrow represents a binding position to the $N(R^2)$.

Especially preferably, 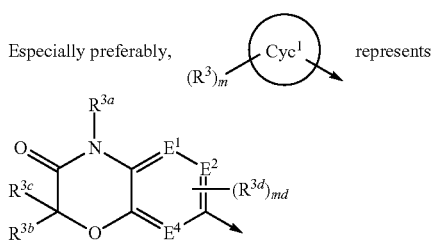 represents two of $E^1$, $E^2$ and $E^4$ are carbon atoms; $R^{3a}$ have the same meanings as described above and the same preferred definitions as set out above; $R^{3b}$ and $R^{3c}$ each independently represent (1) hydrogen, (2) halogen or (3) C1-4 alkyl (e.g. methyl); $R^{3d}$ represents halogen or C1-4 alkyl; md represents an integer of 0 to 2, wherein when md represents 2, each $R^{3d}$ may be same or different; and the arrow represents a binding position to the $N(R^2)$.

Preferably, $R^{3d}$ represents halogen.

Also preferably, 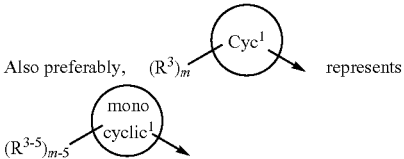 represents wherein monocyclic$^1$ represents (1) 5- to 7-membered mono-cyclic aromatic carbocyclic ring which may be partially saturated or (2) 5- to 7-membered mono-cyclic aromatic heterocyclic ring having 1 to 3 heteroatoms independently selected from nitrogen, oxygen and sulfur, which may be partially saturated (preferably 6-membered mono-cyclic aromatic ring having 0 to 2 nitrogen atom, more preferably benzene or pyridine); $R^{3-5}$ represents (1) halogen, (2) cyano, (3) hydroxy, (4) C1-4 alkyl which may be substituted with 1 to 3 groups selected from halogen, hydroxy and methoxy, (5) C1-4 alkoxy (preferably methoxy), (6) 5- to 6-membered mono-cyclic aromatic heterocyclic ring having 1 to 3 heteroatoms independently selected from nitrogen, oxygen and sulfur, which may be partially or fully saturated and may be substituted with 1 to 3 groups selected from oxo, halogen, cyano, hydroxy and C1-4 alkyl which may be substituted with 1 to 3 groups selected from halogen and hydroxy or (7) 8- to 12-membered bicyclic aromatic heterocyclic ring having 1 to 5 heteroatoms independently selected from nitrogen, oxygen and sulfur, which may be partially or fully saturated and may be substituted with 1 to 5 groups selected from oxo, halogen, cyano, hydroxy and C1-4 alkyl which may be substituted with 1 to 3 groups selected from halogen and hydroxy; and m-5 represents 0 to 3 (preferably 1 to 3), wherein when m-5 represents 2 or 3, each $R^{3-5}$ may be same or different.

Preferably, $R^{3-5}$ represents the same definition as set above, with the proviso that $R^{3-5}$ is not piperazine.

Preferably, "(6) 5- to 6-membered mono-cyclic aromatic heterocyclic ring having 1 to 3 heteroatoms independently selected from nitrogen, oxygen and sulfur, which may be partially or fully saturated and may be substituted with 1 to 3 groups selected from oxo, halogen, cyano, hydroxy and C1-4 alkyl which may be substituted with 1 to 3 groups selected from halogen and hydroxy" as $R^{3-5}$ represents nitrogen-containing 5- to 6-membered mono-cyclic aromatic heterocyclic ring having 1 to 3 heteroatoms independently selected from nitrogen, oxygen and sulfur, which may be partially or fully saturated and may be substituted with 1 to 3 groups selected from oxo, halogen, hydroxy, cyano and C1-4 alkyl which may be substituted with 1 to 3 groups selected from halogen and hydroxy, more preferably nitrogen-containing 5- to 6-membered mono-cyclic aromatic heterocyclic ring having 1 to 3 heteroatoms independently selected from nitrogen, oxygen and sulfur, which may be substituted with 1 to 3 groups selected from halogen, cyano, hydroxy and C1-4 alkyl which may be substituted with 1 to 3 groups selected from halogen and hydroxy, further preferably nitrogen-containing 5-membered mono-cyclic aromatic heterocyclic ring having 1 to 3 heteroatoms independently selected from nitrogen, oxygen and sulfur, which may be substituted with 1 to 3 groups selected from halogen, hydroxyl, cyano and C1-4 alkyl which may be substituted with 1 to 3 groups selected from halogen and hydroxy.

Preferably, "(7) 8- to 12-membered bicyclic aromatic heterocyclic ring having 1 to 5 heteroatoms independently selected from nitrogen, oxygen and sulfur, which may be partially or fully saturated, which may be substituted with 1 to 5 groups selected from oxo, halogen, cyano, hydroxy and C1-4 alkyl which may be substituted with 1 to 3 groups selected from halogen and hydroxy" as $R^{3-5}$ represents nitrogen-containing 8- to 9-membered bicyclic aromatic heterocyclic ring having 1 to 3 heteroatoms independently selected from nitrogen, oxygen and sulfur, which may be partially or fully saturated and may be substituted with 1 to 5 groups selected from oxo, halogen, cyano, hydroxy and C1-4 alkyl which may be substituted with 1 to 3 groups selected from halogen and hydroxy, more preferably nitrogen-containing 8- to 9-membered bicyclic aromatic heterocyclic ring having 1 to 3 heteroatoms independently selected from nitrogen, oxygen and sulfur, which may be substituted with 1 to 3 groups selected from halogen, hydroxyl, cyano and C1-4 alkyl which may be substituted with 1 to 3 groups selected from halogen and hydroxy.

More preferably, 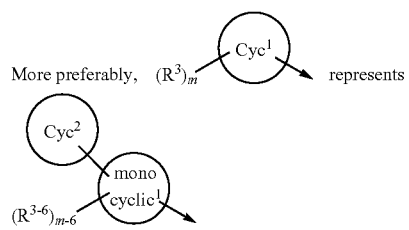 represents wherein monocyclic¹ have the same meanings as described above and the same preferred definitions as set out above; $Cyc^2$ represents (1) 5- to 6-membered mono-cyclic aromatic heterocyclic ring having 1 to 3 heteroatoms independently selected from nitrogen, oxygen and sulfur, which may be partially or fully saturated and may be substituted with 1 to 3 groups selected from oxo, halogen, cyano, hydroxy, and C1-4 alkyl which may be substituted with 1 to 3 groups selected from halogen and hydroxy or (2) 8- to 12-membered bicyclic aromatic heterocyclic ring having 1 to 5 heteroatoms independently selected from nitrogen, oxygen and sulfur, which may be partially or fully saturated and may be substituted with 1 to 5 groups selected from oxo, halogen, cyano, hydroxy and C1-4 alkyl which may be substituted with 1 to 3 groups selected from halogen and hydroxy (preferably (1) nitrogen-containing 5- to 6-membered mono-cyclic aromatic heterocyclic ring having 1 to 3 heteroatoms independently selected from nitrogen, oxygen and sulfur, which may be substituted with 1 to 3 groups selected from halogen, cyano, hydroxy and C1-4 alkyl which may be substituted with 1 to 3 groups selected from halogen and hydroxy or (2) nitrogen-containing 8- to 9-membered bicyclic aromatic ring having 1 to 3 heteroatoms independently selected from nitrogen, oxygen and sulfur, which may be substituted with 1 to 3 groups selected from halogen, cyano, hydroxy and C1-4 alkyl which may be substituted with 1 to 3 groups selected from halogen and hydroxy, more preferably nitrogen-containing 5- to 6-membered mono-cyclic aromatic heterocyclic ring having 1 to 3 heteroatoms independently selected from nitrogen, oxygen and sulfur, which may be substituted with 1 to 3 groups selected from halogen, cyano, hydroxy and C1-4 alkyl which may be substituted with 1 to 3 groups selected from halogen and hydroxy, further preferably nitrogen-containing 5-membered mono-cyclic aromatic heterocyclic ring having 1 to 3 heteroatoms independently selected from nitrogen, oxygen and sulfur, which may be substituted with 1 to 3 groups selected from halogen, hydroxyl, cyano and C1-4 alkyl which may be substituted with 1 to 3 groups selected from halogen and hydroxyl); $R^{3-6}$ represents halogen or C1-4 alkyl which may be substituted with 1 to 3 halogen; and m-6 represents 0 to 2, wherein when m-6 represents 2, each $R^{3-6}$ may be same or different.

Preferably, 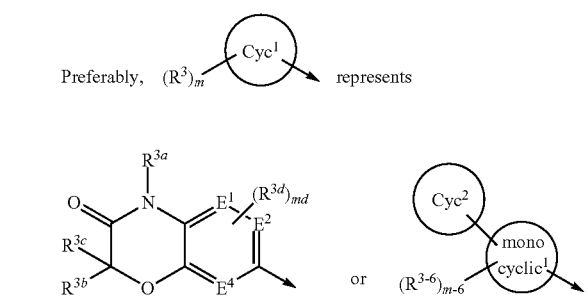 represents wherein all symbols have the same meanings as described above and the same preferred definitions as set out above (alone or in combination).

Preferred compounds of formula (I) include a compound represented by formula (I-A):

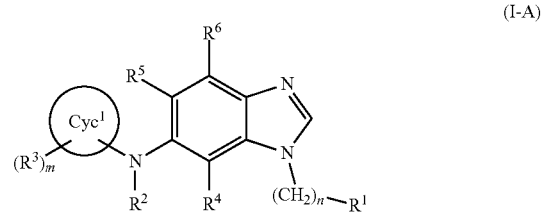

(I-A)

wherein all symbols have the same meanings as described above and the same preferred definitions as set out above (alone or in combination), a compound represented by formula (I-B):

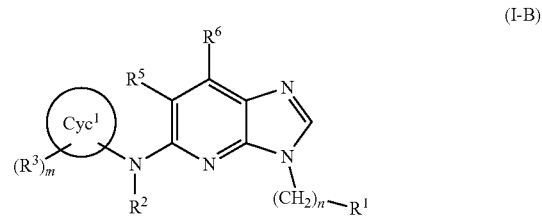

(I-B)

wherein all symbols have the same meanings as described above and the same preferred definitions as set out above (alone or in combination), a compound represented by formula (I-C):

(I-C)

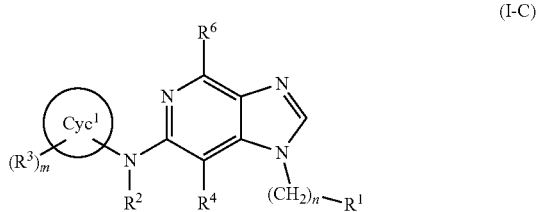

wherein all symbols have the same meanings as described above and the same preferred definitions as set out above (alone or in combination), a compound represented by formula (I-D):

(I-D)

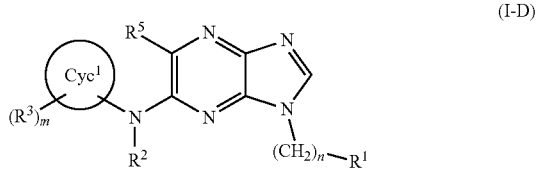

wherein all symbols have the same meanings as described above and the same preferred definitions as set out above (alone or in combination), or a compound represented by formula (I-E):

(I-E)

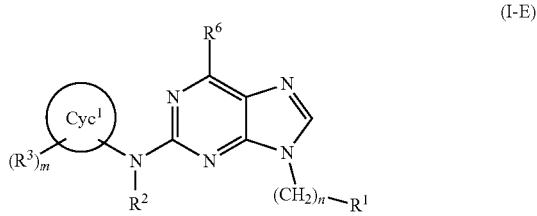

wherein all symbols have the same meanings as described above and the same preferred definitions as set out above (alone or in combination).

Preferred compounds of formula (I) include a compound represented by formula (II):

(II)

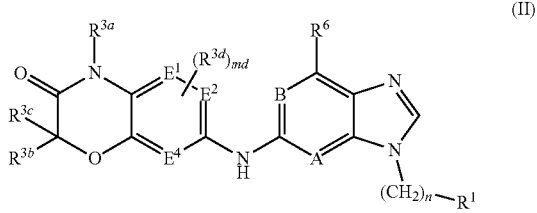

wherein A represents $CR^4$ or N; B represents $CR^5$ or N; $R^1$ represents cyclopropyl, cyclobutyl, oxetanyl, tetrahydrofuranyl, n-propyl or isopropyl, any of which may be substituted with 1 to 3 halogen (preferably cyclopropyl, cyclobutyl, n-propyl or isopropyl); $R^4$ represents hydrogen or halogen (preferably hydrogen); $R^5$ represents (1) hydrogen, (2) halogen, (3) hydroxy, (4) cyano, (5) C1-4 alkyl which may be substituted with 1 to 3 groups selected from halogen and hydroxy, (6) C2-4 alkenyl which may be substituted with 1 to 3 groups selected from halogen and hydroxy, (7) C1-4 alkoxy which may be substituted with 1 to 3 groups selected from halogen and hydroxy, (8) C1-4 alkyl-carbonyl which may be substituted with 1 to 3 groups selected from halogen and hydroxy or (9) 3- to 5-membered cycloalkyl wherein one carbon atom may be replaced by oxygen, which may be substituted with 1 to 3 groups selected from halogen and hydroxyl (preferably (1) hydrogen, (2) halogen, (3) hydroxy, (4) cyano, (5) methyl or ethyl, (6) ethenyl, (7) methoxy which may be substituted with halogen or (8) cyclopropyl); $R^6$ represents halogen or methyl which may be substituted with halogen; n represents 0 or 1; $E^1$, $E^2$ and $E^4$ each independently represent a carbon atom or a nitrogen atom, with the proviso that at least two of $E^1$, $E^2$ and $E^4$ are carbon atoms; $R^{3a}$ represents (1) hydrogen, (2) C1-4 alkyl which may be substituted with 1 to 3 groups selected from halogen, hydroxy and methoxy (preferably (i) C1-4 alkyl, (ii) C1-4 alkyl substituted with 1 to 3 halogen, (iii) C1-4 alkyl substituted with hydroxy or (iv) C1-4 alkyl substituted with methoxy) or (3) —$(CH_2)_p$-(3- to 5-membered cycloalkyl), wherein one carbon atom in cycloalkyl may be replaced by oxygen and p represents 0 or 1 (preferably cyclopropyl, cyclobutyl, oxetanyl, —$CH_2$— cyclopropyl, —$CH_2$— cyclobutyl or —$CH_2$— oxetanyl); $R^{3b}$ and $R^{3c}$ each independently represent (1) hydrogen, (2) halogen or (3) C1-4 alkyl (e.g. methyl); $R^{3d}$ represents halogen or C1-4 alkyl (preferably halogen); md represents an integer of 0 to 2, wherein when md represents 2, each $R^{3d}$ may be same or different.

More preferred compounds of formula (I) include a compound represented by formula (II-1):

(II-1)

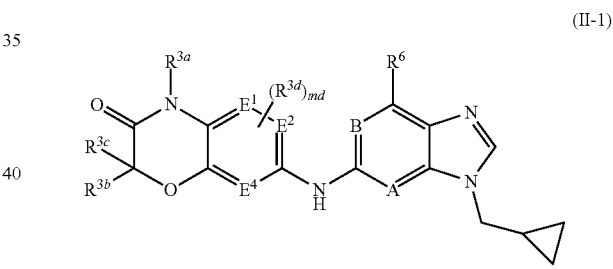

wherein all symbols have the same meanings as described above formula (II) and the same preferred definitions as set out above formula (II) (alone or in combination).

More preferred compounds of formula (I) include a compound represented by formula (II-A):

(II-A)

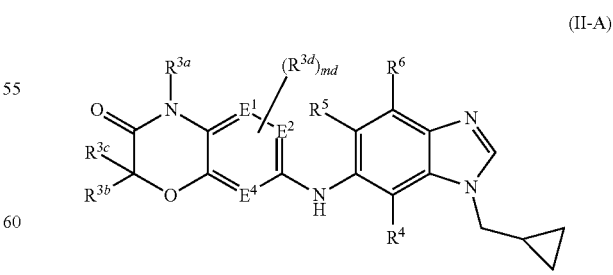

wherein all symbols have the same meanings as described above formula (II) and the same preferred definitions as set out above formula (II) (alone or in combination), a compound represented by formula (II-B):

(II-B)

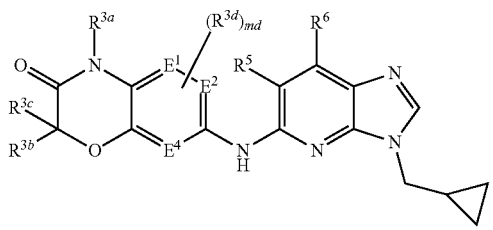

wherein all symbols have the same meanings as described above formula (II) and the same preferred definitions as set out above formula (II) (alone or in combination), a compound represented by formula (II-C):

(II-C)

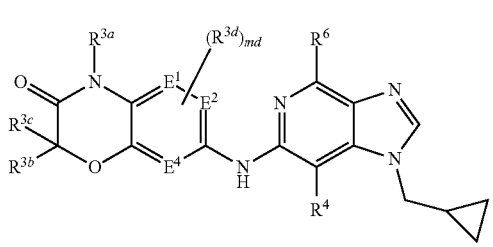

wherein all symbols have the same meanings as described above formula (II) and the same preferred definitions as set out above formula (II) (alone or in combination), a compound represented by formula (II-D):

(II-D)

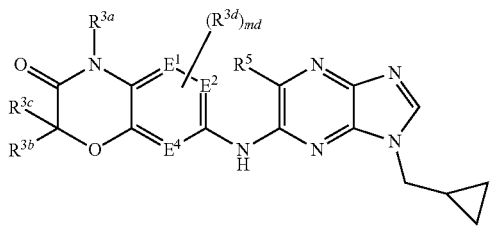

wherein all symbols have the same meanings as described above formula (II) and the same preferred definitions as set out above formula (II) (alone or in combination), or a compound represented by formula (II-E):

(II-E)

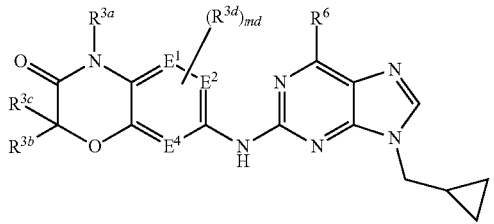

wherein all symbols have the same meanings as described above formula (II) and the same preferred definitions as set out above formula (II) (alone or in combination).

Preferred compounds of formula (I) include a compound represented by formula (III):

(III)

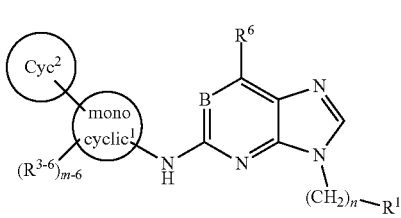

wherein A represents $CR^4$ or N; B represents $CR^5$ or N; $R^1$ represents cyclopropyl, cyclobutyl, oxetanyl, tetrahydrofuranyl, n-propyl or isopropyl, any of which may be substituted with 1 to 3 halogen (preferably cyclopropyl, cyclobutyl, n-propyl or isopropyl); $R^4$ represents hydrogen or halogen (preferably hydrogen); $R^5$ represents (1) hydrogen, (2) halogen, (3) hydroxy, (4) cyano, (5) C1-4 alkyl which may be substituted with 1 to 3 groups selected from halogen and hydroxy, (6) C2-4 alkenyl which may be substituted with 1 to 3 groups selected from halogen and hydroxy, (7) C1-4 alkoxy which may be substituted with 1 to 3 groups selected from halogen and hydroxy, (8) C1-4 alkyl-carbonyl which may be substituted with 1 to 3 groups selected from halogen and hydroxy or (9) 3- to 5-membered cycloalkyl wherein one carbon atom may be replaced by oxygen, which may be substituted with 1 to 3 groups selected from halogen and hydroxyl (preferably (1) hydrogen, (2) halogen, (3) hydroxy, (4) cyano, (5) methyl or ethyl, (6) ethenyl, (7) methoxy which may be substituted with halogen or (8) cyclopropyl); $R^6$ represents halogen or methyl which may be substituted with halogen; n represents 0 or 1; monocyclic$^1$ represents (1) 5- to 7-membered mono-cyclic aromatic carbocyclic ring which may be partially saturated or (2) 5- to 7-membered mono-cyclic aromatic heterocyclic ring having 1 to 3 heteroatoms independently selected from nitrogen, oxygen and sulfur, which may be partially saturated (preferably 6-membered mono-cyclic aromatic ring having 0 to 2 nitrogen atom, more preferably benzene or pyridine); $Cyc^2$ represents (1) 5- to 6-membered mono-cyclic aromatic heterocyclic ring having 1 to 3 heteroatoms independently selected from nitrogen, oxygen and sulfur, which may be partially or fully saturated and may be substituted with 1 to 3 groups selected from oxo, halogen, cyano, hydroxy, and C1-4 alkyl which may be substituted with 1 to 3 groups selected from halogen and hydroxy or (2) 8- to 12-membered bicyclic aromatic heterocyclic ring having 1 to 5 heteroatoms independently selected from nitrogen, oxygen and sulfur, which may be partially or fully saturated and may be substituted with 1 to 5 groups selected from oxo, halogen, cyano, hydroxy and C1-4 alkyl which may be substituted with 1 to 3 groups selected from halogen and hydroxy (preferably (1) nitrogen-containing 5- to 6-membered mono-cyclic aromatic heterocyclic ring having 1 to 3 heteroatoms independently selected from nitrogen, oxygen and sulfur, which may be substituted with 1 to 3 groups selected from halogen, cyano, hydroxy and C1-4 alkyl which may be substituted with 1 to 3 groups selected from halogen and hydroxyl or (2) nitrogen-containing 8- to 9-membered bicyclic aromatic heterocyclic ring having 1 to 3 heteroatoms independently selected from nitrogen, oxygen and sulfur, any of which may be substituted with 1 to 3 groups selected from halogen, cyano, hydroxy and C1-4 alkyl which may be substituted with 1 to 3 groups selected from halogen and hydroxy, more preferably nitrogen-containing 5- to 6-membered mono-cyclic aromatic heterocyclic ring having 1 to 3 heteroatoms independently selected from nitrogen, oxygen and sulfur, which may be substituted with 1 to 3 groups selected from halogen, cyano, hydroxy and C1-4 alkyl which may be substituted with 1 to 3 groups selected from halogen and hydroxy, further preferably nitrogen-containing 5-membered mono-cyclic aromatic heterocyclic ring having 1 to 3 heteroatoms independently selected from nitrogen, oxygen and sulfur, which may be substituted with 1 to 3 groups selected from halogen, hydroxyl, cyano and C1-4 alkyl which may be substituted with 1 to 3 groups selected from halogen and hydroxyl); $R^{3-6}$ represents halogen or C1-4 alkyl which may be substituted with 1 to 3 halogen; and m-6 represents 0 to 2, wherein when m-6 represents 2, each $R^{3-6}$ may be same or different.

More preferred compounds of formula (I) include a compound represented by formula (III-A):

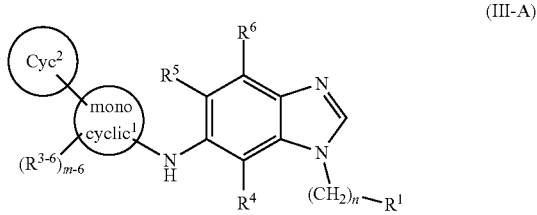

(III-A)

wherein all symbols have the same meanings as described above formula (III) and the same preferred definitions as set out above formula (III) (alone or in combination), a compound represented by the formula (III-B):

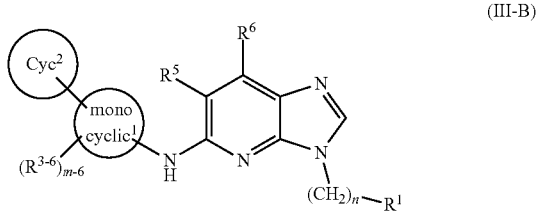

(III-B)

wherein all symbols have the same meanings as described above formula (III) and the same preferred definitions as set out above formula (III) (alone or in combination), a compound represented by the formula (III-C):

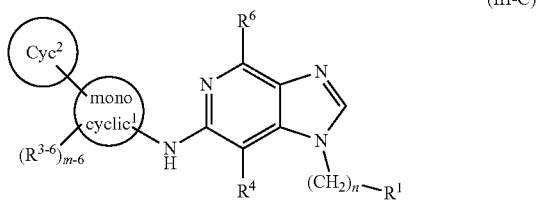

(III-C)

wherein all symbols have the same meanings as described above formula (III) and the same preferred definitions as set out above formula (III) (alone or in combination), a compound represented by the formula (III-D):

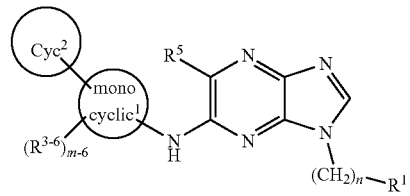

(III-D)

wherein all symbols have the same meanings as described above formula (III) and the same preferred definitions as set out above formula (III) (alone or in combination), or a compound represented by the formula (III-E):

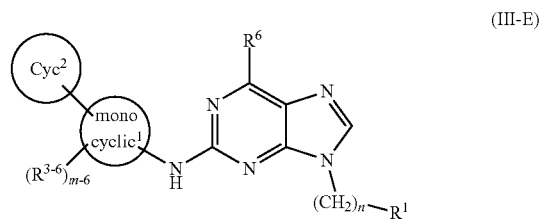

(III-E)

wherein all symbols have the same meanings as described above formula (III) and the same preferred definitions as set out above formula (III) (alone or in combination).

Preferred compounds of formula (I) include a compound represented by formula (IV):

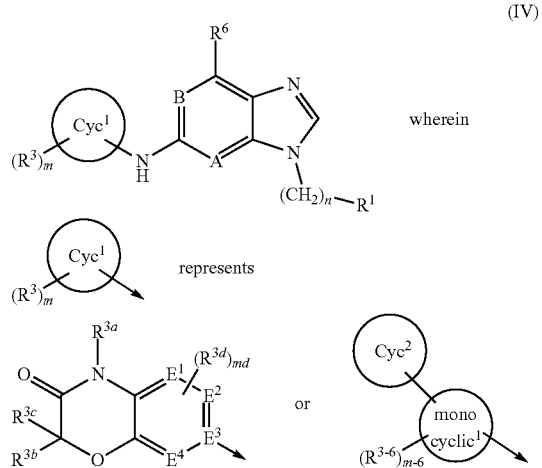

(IV)

wherein $Cyc^1$ represents the other symbols have the same meanings as described above formula (II) or formula (III) and the same preferred definitions as set out above formula (II) or formula (III) (alone or in combination).

Unless otherwise specifically mentioned, all isomers are included in the present invention. For example, alkyl, alkenyl, alkynyl, and alkoxy may be straight chain or branched. Moreover, all isomers due to double bond, ring and fused ring (E-, Z-, cis- and trans-forms), isomers due to the presence of asymmetric carbon(s) etc. (R-, S-, α- and β-configuration, enantiomer and diastereomer), optically active substances having optical rotation (D-, L-, d- and l-forms), polar compounds by chromatographic separation (more polar compounds and less polar compounds), equilibrium compounds, rotational isomers, a mixture thereof in any proportion and a racemic mixture are included in the present invention.

The compound represented by the general formula (I) is converted into corresponding salt by the known method. The salt of the compound represented by formula (I) includes all nontoxic salts or pharmaceutically acceptable salts. With regard to the pharmaceutically acceptable salts, those which are low-toxicity and soluble in water are preferred. Examples of appropriate salts of the compounds represented by formula (I) are salt with alkaline metal (such as potassium, sodium and lithium), salt with alkaline earth metal (such as calcium and magnesium), ammonium salt (such as ammonium salt, tetramethylammonium salt and tetrabutylammonium salt), salt with organic amine (such as triethylamine, methylamine, dimethylamine, cyclopentylamine, benzylamine, phenethylamine, piperidine, monoethanolamine, diethanolamine, tris(hydroxymethyl) methylamine, lysine, arginine and N-methyl-D-glucamine) and acid addition salt (such as inorganic acid salt (e.g. hydrochloride, hydrobromide, hydroiodide, sulfate, phosphate and nitrate) and organic acid salt (e.g. formate, acetate, trifluoroacetate, lactate, tartrate, oxalate, fumarate, maleate, benzoate, citrate, methanesulfonate, ethanesulfonate, benzenesulfonate, toluenesulfonate, isothionate, glucuronate and gluconate)).

The compounds represented by the general formula (I) and salts thereof can be also converted into solvates. It is preferable that the solvate is low-toxic and water-soluble. Examples of suitable solvates include solvates with, for example, water, or alcohol-based solvents (e.g. ethanol).

The compound of the present invention can be converted into an N-oxide by known methods. The N-oxide is the compound wherein nitrogen of the compound represented by formula (I) is oxidized.

A prodrug of the compound represented by formula (I) means a compound which is converted to the compound represented by formula (I) by reaction with an enzyme, gastric acid or the like in the living body. For example, with regard to a prodrug of the compound represented by formula (I), when the compound represented by formula (I) has an amino group, the prodrug is a compound in which the amino group is, for example, acylated, alkylated or phosphorylated (e.g. a compound in which the amino group of the compound represented by formula (I) is eicosanoylated, alanylated, pentylaminocarbonylated, (5-methyl-2-oxo-1,3-dioxolen-4-yl)methoxycarbonylated, tetrahydrofuranylated, pyrrolidyl-methylated, pivaloyloxymethylated, acetoxymethylated, tert-butylated, etc.); when the compound represented by formula (I) has a hydroxyl group, the prodrug is a compound wherein the hydroxyl group is, for example, acylated, alkylated, phosphorylated or borated (e.g. a compound in which the hydroxyl group of the compound represented by formula (I) is acetylated, palmitoylated, propanoylated, pivaloylated, succinylated, fumarylated, alanylated or dimethylaminomethylcarbonylated). Those compounds may be produced by a known method per se. The prodrug of the compound represented by formula (I) may be either a hydrate or a non-hydrate. A prodrug of the compound represented by formula (I) may also be a compound which is converted to the compound represented by formula (I) under physiological conditions as described in "Iyakuhin no kaihatsu, Vol. 7 (Bunshi-sekkei), pp. 163-198 (Hirokawa-Shoten), 1990". Further, the compound represented by formula (I) may also be labeled by a radio isotope (such as $^2H$, $^3H$, $^{11}C$, $^{13}C$, $^{14}C$, $^{13}N$, $^{15}N$, $^{15}O$, $^{17}O$, $^{18}O$, $^{35}S$, $^{18}F$, $^{36}Cl$, $^{123}I$, $^{125}I$, etc.).

Processes for the Preparation of the Compound of the Present Invention:

The compound of the invention can, for example, be prepared according to the following reaction schemes.

The compound of the present invention represented by the formula (I) may be prepared by known methods, for example, a method combining the following methods, the method according to these methods, the methods described in the examples and/or methods described in Comprehensive Organic Transformations: A Guide to Functional Group Preparations, 2nd Edition (Richard C. Larock, John Wiley & Sons Inc, 1999), etc., which are appropriately modified in each following method for the preparation. Salts of the starting materials may be used.

The compound of the present invention represented by the formula (I) can be prepared as outlined in Reaction Scheme 1, wherein the symbols have the meanings described above.

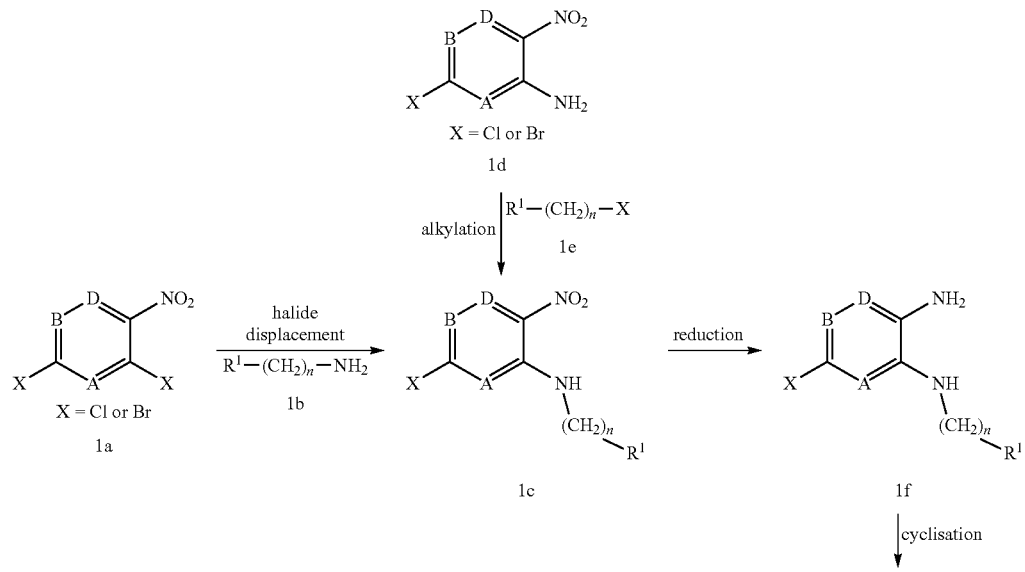

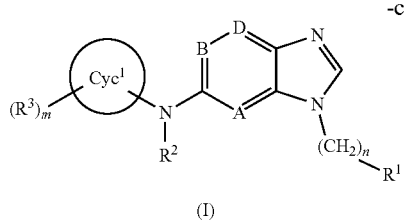
(I)

-continued

Pd-catalysed amination

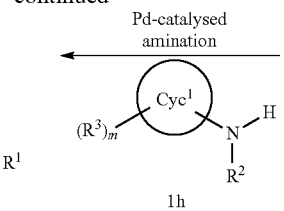
1h

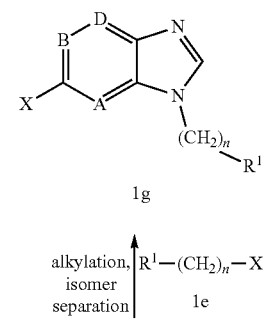
1g alkylation, isomer separation  $R^1$—$(CH_2)_n$—X
1e

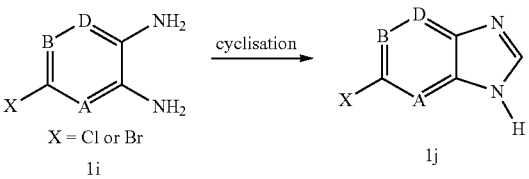
X = Cl or Br
1i cyclisation

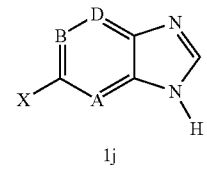
1j

In Reaction Scheme 1, the compound represented by formula (I) can be prepared from the compound represented by formula 1a.

In the first step, halide displacement from the compound represented by formula 1a using an amine represented by the formula 1b gives the compound represented by formula 1c. Typically, the halide displacement reaction can be conducted in an organic solvent such as tetrahydrofuran, using a base such as diisopropylethylamine. Alternatively, the compound represented by formula 1c can be synthesized by an alkylation reaction of the compound represented by formula 1d with an alkylating agent represented by formula 1e. Typically, the alkylation reaction can be conducted in an organic solvent such as dimethylformamide, using a base such as sodium hydride or potassium carbonate.

Reduction of the nitro group of the compound represented by formula 1c gives the amino compound represented by formula 1f. Typically, this reaction can be conducted in an organic solvent such as ethanol, using a reducing agent such as iron powder at 90° C.

Cyclisation of the diamino compound represented by formula 1f gives the fused imidazole compound represented by formula 1g. Typically, the cyclisation is achieved by reaction with trimethylorthoformate in the presence of catalytic para-toluene sulfonic acid at 90° C. Alternatively, the compound represented by formula 1g can be prepared by cyclisation of the diamine represented by formula 1i to give the fused imidazole compound represented by formula 1j, followed by alkylation of the compound represented by formula 1j with an alkylating agent represented by formula 1e.

Palladium-catalysed amination of the fused imidazole compound represented by formula 1g with an amine represented by formula 1h gives the compounds of the present invention represented by the formula (I). Typically, the amination reaction is achieved by use of a source of palladium, [e.g. tris(dibenzylideneacetone)dipalladium(0)], a phosphine ligand [e.g. 4,5-bis(diphenylphosphino)-9,9-dimethylxanthene (Xantphos)], an inorganic base (e.g. cesium carbonate), and an organic solvent (e.g. dioxan) at 100° C.

Representative examples of the amines represented by formula 1h were prepared as outlined in Reaction Scheme 2, wherein the symbols have the meanings described above.

Reaction Scheem 2

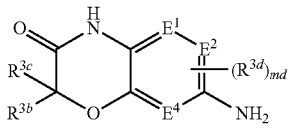
2a alkylation
$R^{3a}$—X
2b

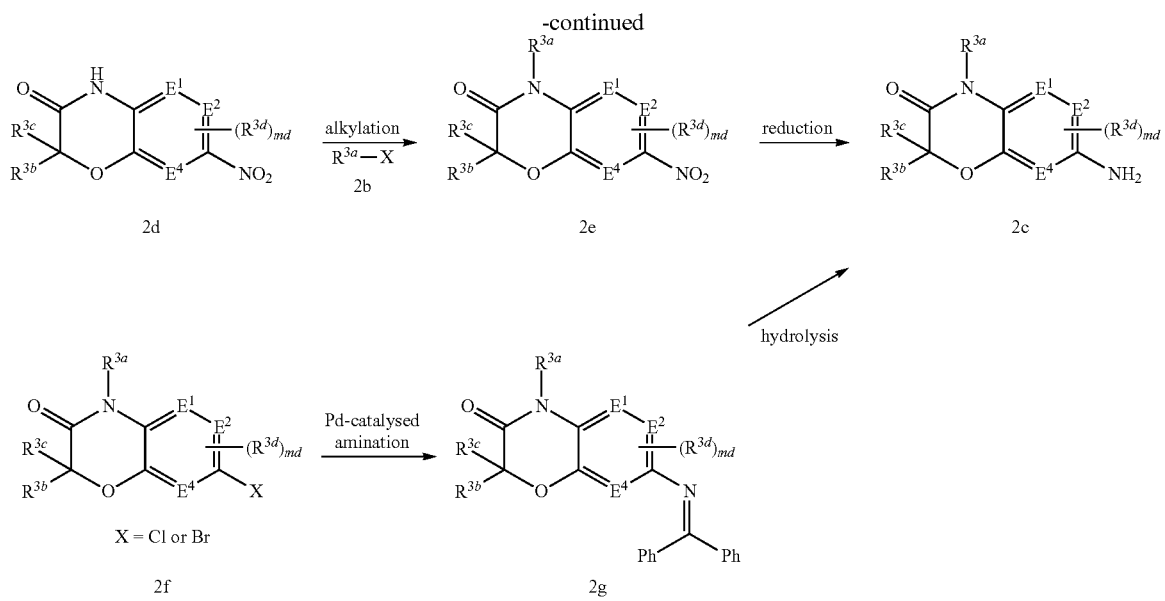

In the first step, alkylation of the compound represented by formula 2a with an alkyl halide represented by the formula 2b gives the compound represented by formula 2c, which represents a sub-set of the compounds represented by formula 1h in Reaction Scheme 1. Typically, the alkylation reaction can be achieved using a base such as sodium hydride in an organic solvent such as dimethylformamide.

Alternatively, the compound represented by formula 2c can be prepared by a similar alkylation reaction of the compound represented by formula 2d with an alkylating agent represented by formula 2b, followed by reduction of the nitro group of the compound represented by formula 2e. Typically, the reduction reaction can be conducted in an organic solvent such as ethanol, using a reducing agent such as iron powder at 90° C.

Alternatively, the compound represented by formula 2c can be prepared by a palladium-catalysed amination reaction of the compound represented by formula 2f, followed by hydrolysis. Typically, the palladium-catalysed amination reaction can be conducted using an amine (e.g. benzophenone imine), a source of palladium, [e.g. tris(dibenzylideneacetone)dipalladium(0)], a phosphine ligand [e.g. 2,2'-bis(diphenylphosphino)-1,1'-binaphthyl (BINAP)], an inorganic base (e.g. sodium tert-butoxide), and an organic solvent (e.g. toluene) at 110° C. Typically, the hydrolysis reaction of the compound represented by formula 2g can be conducted using an organic solvent such as tetrahydrofuran, and an aqueous acid, such as dilute hydrochloric acid.

Representative examples of the amines represented by formula 1h were also prepared as outlined in Reaction Scheme 3, wherein the symbols have the meanings described above:

Reaction Scheme 3

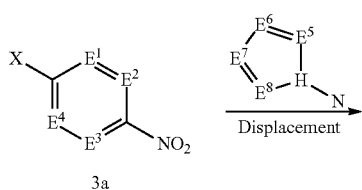

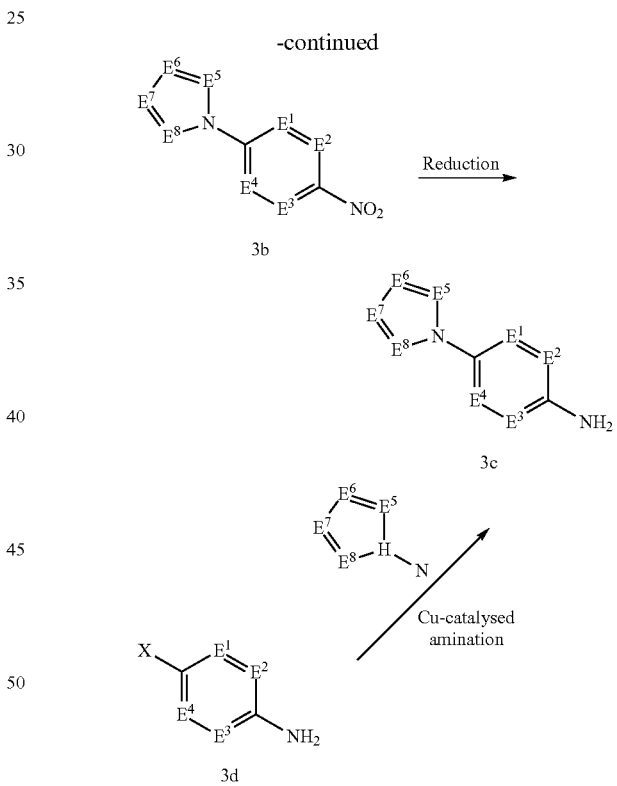

In the first step, reaction of the compound represented by formula 3a with a heterocyclic amine gives the compound represented by formula 3b. Typically, the amination reaction can be achieved using an amine such as imidazole in an organic solvent such as dimethylsulfoxide. Reduction of the nitro group of the compound represented by 3b gives the compound represented by formula 3c, which represent a sub-set of the compounds represented by formula 1h in Reaction Scheme 1. Typically, the reduction reaction can be conducted in an organic solvent such as ethanol, using a reducing agent such as iron powder at 90° C.

Alternatively, the compound represented by formula 3c can be prepared by a copper-catalysed amination reaction of the compound represented by formula 3d. Typically, the amination reaction can be conducted using an amine (e.g. 4-chloroimidazole), a source of copper, [e.g. copper(I) iodide], a ligand [e.g. N,N,N',N'-tetramethylethylenediamine], an inorganic base (e.g. potassium phosphate), and an organic solvent (e.g. DMF) at 130° C.

Representative examples of the amines represented by formula 1h were also prepared as outlined in Reaction Scheme 4, wherein the symbols have the meanings described above:

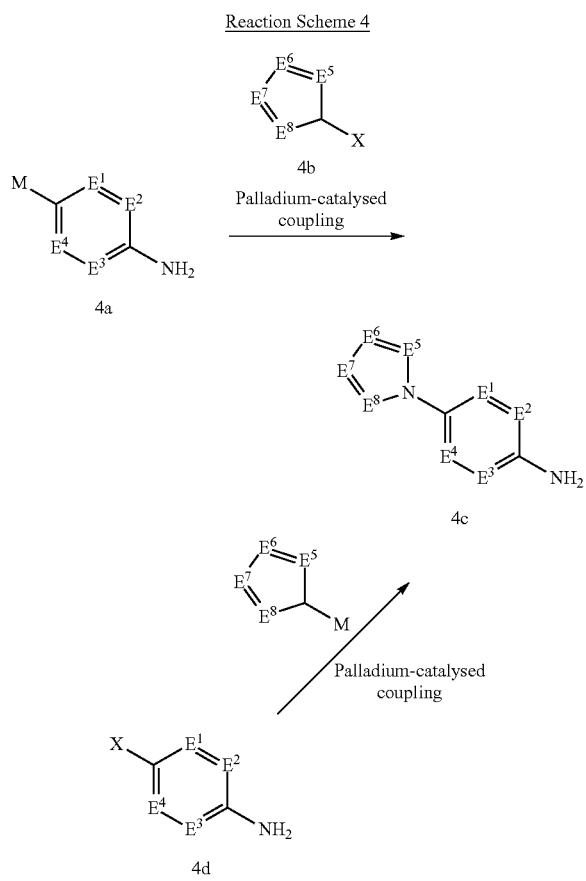

Palladium-catalysed reaction of a (hetero)aryl boronate ester or stannane represented by formula 4a with a heteroaryl halide represented by the formula 4b gives the compound represented by formula 4c, which represents a sub-set of the compounds represented by formula 1h in Reaction Scheme 1. Alternatively, the compound represented by formula 4c can be prepared by palladium-catalysed reaction of a (hetero)aryl halide represented by formula 4d with a heteroaryl boronate ester represented by the formula 4e. Typically, the coupling reaction can be conducted using a palladium catalyst [e.g. tetrakis(triphenylphosphine)palladium(0)], an inorganic base (e.g. sodium carbonate), water, and an organic solvent (e.g. DMF) at 90° C.

The compounds of the present invention can be prepared by the reactions or modified variants of the reactions described above.

Starting compounds (e.g. formula 1a, 1b, 1d, 1e, 1i, 2a, 2b, 2d, 2f, 3a, 3d, 4a, 4b, 4d, 4e) or compounds used as reagents are known per se or can be easily prepared by using the methods described in Examples of the present specification, or any conventional known method, for example, methods described in Comprehensive Organic Transformations: A Guide to Functional Group Preparations, 2nd Edition (Richard C. Larock, John Wiley & Sons Inc, 1999) or Elmer J. Rauckman et al., J. Org. Chem., Vol. 41, No. 3, 1976, p 564-565 etc.

In each reaction of the specification, the reactions with heating, as will be apparent to those skilled in the art, may be carried out using a water bath, an oil bath, a sand bath, a heating block or by microwave.

In each reaction of the specification, a solid phase reagent may be used which is supported by a polymer (for example, polystyrene, polyacrylamide, polypropylene or polyethyleneglycol etc.).

In each reaction of the specification, the products obtained may be purified by conventional techniques. For example, the purification may be carried out by distillation at atmospheric or reduced pressure, by high performance liquid chromatography with silica gel or magnesium silicate, by thin layer chromatography, by ion-exchange resin, by scavenger resin, by column chromatography, by washing, trituration or recrystallization. The purification may be carried out after each reaction stage or after several reaction stages.

Toxicity:

The toxicity of the compound of the present invention is very low and therefore it may be considered safe for pharmaceutical use.

Application to Pharmaceuticals:

The compound of the present invention is therapeutically useful. The present invention therefore provides a compound represented by formula (I), as defined above, or a pharmaceutically acceptable salt thereof, an N-oxide thereof, a solvate thereof or a prodrug thereof, for use in the treatment of the human or animal body by therapy.

Also provided is a pharmaceutical composition or medicament comprising a compound represented by formula (I), as defined above, or a pharmaceutically acceptable salt thereof, an N-oxide thereof, a solvate thereof or a prodrug thereof, and a pharmaceutically acceptable carrier or diluents.

The compound of the present invention may normally be administered systemically or locally, usually by oral or parenteral administration.

A therapeutically effective amount of a compound of the present invention is administered to mammals (preferably patients). The doses to be administered are determined depending upon, for example, age, body weight, symptom, the desired therapeutic effect, the route of administration, and the duration of the treatment. In general, the doses per person are generally from 0.1 mg to 1000 mg, by oral administration, up to several times per day, and from 0.01 mg to 100 mg, by parenteral administration (preferably intravenous administration), up to several times per day, or continuous administration from 1 to 24 hours per day from vein.

As mentioned above, the doses to be used depend upon various conditions. Therefore, there are cases in which doses lower than or greater than the ranges specified above may be used.

The compound or pharmaceutical composition of the present invention may be administered for example, in the form of a solid for oral administration, liquid forms for oral administration, injections, liniments or suppositories for parenteral administration.

Preferably, the compound or pharmaceutical composition of the present invention is administered orally.

Solid forms for oral administration include compressed tablets, pills, capsules, dispersible powders, and granules. Capsules include hard capsules and soft capsules.

In such solid forms, one or more of the active compound(s) may be admixed with excipients (such as lactose, mannitol, glucose, microcrystalline cellulose or starch), binders (such as hydroxypropyl cellulose, polyvinylpyrrolidone or magnesium metasilicate aluminate), disintegrants (such as cellulose calcium glycolate), lubricants (such as magnesium stearate), stabilizing agents, solubilizing agents (such as glutamic acid or aspartic acid) or the like, and prepared according to methods well known in normal pharmaceutical practice, for example, by means of mixing, granulating, tableting, sugar coating, or film coating processes. The solid forms may, if desired, be coated with coating agents (such as sugar, gelatin, hydroxypropyl cellulose or hydroxypropylmethyl cellulose phthalate), or be coated with two or more films. Furthermore, coating may include containment within capsules of absorbable materials such as gelatin.

Liquid forms for oral administration include pharmaceutically acceptable solutions, suspensions, emulsions, syrups and elixirs. In such forms, one or more of the active compound(s) may be dissolved, suspended or emulsified into diluent(s) commonly used in the art (such as purified water, ethanol or a mixture thereof). Besides such liquid forms may also comprise some additives, such as wetting agents, suspending agents, emulsifying agents, sweetening agents, flavoring agents, aroma, preservative or buffering agent.

The injections for parenteral administration include, for example, solutions, suspensions, emulsions, and solid formulations for injection which are dissolved, suspended or emulsified into solvent(s) for injection before use. The injections are prepared by dissolving, suspending or emulsifying one or more active substances in a solvent. Examples of the solvent may include distilled water for injection, saline, vegetable oil, propylene glycol, polyethylene glycol or alcohols such as ethanol, and any combination thereof. The injections may further contain a stabilizing agent, a solubilizing agent (such as glutamic acid, aspartic acid, polysorbate 80 (registered trademark)), a suspending agent, an emulsifying agent, a soothing agent, a buffer or a preservative, etc. These are prepared by sterilizing in the final process or by a sterile operation method. Alternatively, they may be used by firstly producing sterile solid formulations such as freeze-dried formulations and dissolving them in sterilized or sterile distilled water for injection or another sterile solvent prior to their use.

Other forms for parenteral administration include liquids for external use, ointments and endermic liniments, inhalations, sprays, suppositories and vaginal suppositories which comprise one or more of the active compound(s) and may be prepared by methods known per se.

Sprays may comprise additional substances other than diluents, used commonly, stabilizers such as sodium hydrogensulfite and buffers capable of imparting isotonicity, for example, isotonic buffers such as sodium chloride, sodium citrate or citric acid. For the preparation of the spray formulation, details thereof can be found, for example, in U.S. Pat. Nos. 2,868,691 and 3,095,355.

Effect of the Invention

The compound of the present invention represented by formula (I) acts as potent and selective $GABA_A$ α5 negative allosteric modulator. In the present invention, negative allosteric modulators (NAM) act as non-competitive antagonists and can have inverse agonist properties. The compound of the present invention can therefore be used for the treatment or prevention of diseases which are related to the $GABA_A$ α5 receptor.

The present invention therefore provides a compound represented by formula (I) as defined above, a pharmaceutically acceptable salt thereof, an N-oxide thereof, a solvate thereof or a prodrug thereof for use in the prevention and/or treatment of a disease which is related to the $GABA_A$ α5. Also provided is a method of treating a patient suffering from or susceptible to a disease which is related to the $GABA_A$ α5, which comprises administering to said patient an effective amount of a compound represented by formula (I) as defined above, a pharmaceutically acceptable salt thereof, an N-oxide thereof, a solvate thereof or a prodrug thereof. Further provided is the use of a compound represented by formula (I) as defined above, a pharmaceutically acceptable salt thereof, an N-oxide thereof, a solvate thereof or a prodrug thereof in the manufacture of a medicament for the prevention and/or treatment of a disease which is related to the $GABA_A$ α5.

The diseases which are related to the $GABA_A$ α5 may be, for example, selected from the group consisting of acute and/or chronic neurological disorders, cognitive disorders; Alzheimer's disease; memory deficits; mild cognitive impairment (MCI); schizophrenia; positive, negative and/or cognitive symptoms associated with schizophrenia; bipolar disorders; autism; Down syndrome; neurofibromatosis type I; sleep disorders; disorders of circadian rhythms; amyotrophic lateral sclerosis (ALS); dementia caused by AIDS; head trauma; Huntington's disease; Pick's disease; Creutzfeld Jakob disease; psychotic disorders; substance-induced psychotic disorder; anxiety disorders; generalized anxiety disorder; panic disorder; delusional disorder; obsessive/compulsive disorders; acute stress disorder; drug addictions; movement disorders; Parkinson's disease; restless leg syndrome; cognition deficiency disorders; multi-infarct dementia; mood disorders; depression; neuropsychiatric conditions; psychosis; attention-deficit/hyperactivity disorder; neuropathic pain; stroke; multiple sclerosis (MS); acute meningitis; alcoholism; Fetal Alcohol Syndrome; attentional disorders; and central nervous system (CNS) conditions occurring after stroke; and need for cognition enhancement.

The present invention provides the use of the compound represented by formula (I) as described above for the prevention, treatment and/or delay of progression of CNS conditions in Down Syndrome, in autism, in neurofibromatosis type I or occurring after stroke.

The prevention and/or treatment of Alzheimer's disease, schizophrenia, Down syndrome and CNS conditions occurring after stroke are particular embodiments of present invention.

The compound of the present invention may be administered in combination with one or more other drugs for:
1) complementing and/or potentiating the preventing and/or treating effect of the compound,
2) improving pharmacokinetics and absorption of the compound, decreasing a dose, and/or
3) alleviating side effect of the compound.

Such other drug(s) may be administered, by a route and in an amount commonly used therefore, contemporaneously or sequentially with a compound of the present invention. When a compound of the present invention is used contemporaneously with one or more other drugs, a pharmaceutical composition in unit dosage form containing such other drugs and the compound of the present invention is envisioned. However, the combination therapy may also include therapies in which the compound of the present invention and one or more other drugs are administered on different overlapping schedules. It is also contemplated that when used in combination with one or more other active ingredients, the compound of the present invention and the other active ingredients may be used in lower doses than when each is used singly.

The other drug(s) for the prevention and/or treatment of Alzheimer's disease is at least one drug selected from acetylcholinesterase inhibitors (e.g. tacrine, donepezil, rivastigmine or galantamine), N-methyl-D-aspartate (NMDA) receptor antagonists (e.g. memantine), amyloid beta vaccine, anti-amyloid beta antibody, γ-secretase inhibitors, β-secretase inhibitors, tau aggregation inhibitors, etc.

The other drug(s) for the prevention and/or treatment of schizophrenia is at least one drug selected from typical antipsychotics (e.g. chlorpromazine, fluphenazine, haloperidol, sulpiride) and atypical antipsychotics such as serotonin-dopamine antagonist (e.g. risperidone, perospirone, blonanserin), multi-acting receptor targeted antipsychotics (e.g. olanzapine, quetiapine, clozapine), dopamine partial agonist (e.g. aripiprazole), etc.

EXAMPLES

Although the present invention will be described in more detail by the following Examples and Biological Examples, it is not limited thereto.

The parenthesized solvents as indicated in the position of chromatographic separation and TLC denote the elution solvents or developing solvents as used, with the ratio being on a volume basis. The parenthesized solvent as indicated under the heading of NMR denotes the solvent used in the measurement.

Compounds in the following Examples were named using the Struct=Name in Chemdraw Ultra 12.0.3.

Example 1

7-Amino-4-(2-methoxyethyl)-2H-benzo[b][1,4]oxazin-3(4H)-one

2-Bromoethyl methyl ether (1.20 mmol, 0.11 mL) was added to a suspension of 7-amino-2H-benzo[b][1,4]oxazin-3(4H)-one (1.00 mmol, 0.16 g) and potassium carbonate (2.00 mmol, 0.28 g) in DMF (5 mL) and the mixture was stirred for 24 hours. Water was added and the mixture was extracted with ethyl acetate. The combined organic extracts were dried ($MgSO_4$) and concentrated under reduced pressure. The residue was purified by column chromatography (silica gel, gradient of 0-5% methanol in dichloromethane) to give the title compound as a yellow solid (0.05 g, 22%).

Example 2

7-Amino-6-chloro-4-(2,2-difluoroethyl)-2H-benzo[b][1,4]oxazin-3(4H)-one

Sodium hydride (60% w/w in mineral oil, 2.64 mmol, 0.105 g) was added to a solution of 7-amino-6-chloro-2H-benzo[b][1,4]oxazin-3(4H)-one (2.51 mmol, 0.50 g) in DMF (5 mL) under $N_2$. After 10 minutes, 2,2-difluoroiodoethane (3.01 mmol, 0.286 mL) was added and the mixture heated at 80° C. for 8 hours. The mixture was cooled and water added. The resulting precipitate was isolated by filtration, washed with water and dried under suction to give the title compound (506 mg, 77%).

Example 3

5-Chloro-7-nitro-2H-benzo[b][1,4]oxazin-3(4H)-one

Boron tribromide (1M in dichloromethane, 2.97 mmol, 2.97 mL) was added drop-wise to a solution of 2-chloro-6-methoxy-4-nitroaniline (2.48 mmol, 0.50 g) in dichloromethane (10 mL) at 0° C. under $N_2$. The mixture was stirred at 0° C. for 30 minutes then allowed to warm to room temperature. Stirring was continued for a further 4.5 hours. Ethanol (5 mL) was added and the mixture was stirred for 10 minutes before being diluted with ethyl acetate. The organics were washed with water then brine, dried ($MgSO_4$) and concentrated under reduced pressure to give a black solid. This was dissolved in DMF (5 mL) and methyl bromoacetate (2.73 mmol, 0.26 mL) and potassium fluoride (6.20 mmol, 0.36 g) were added. The mixture was heated at 90° C. under $N_2$ for 40 hours. The cooled mixture was then poured into water and extracted with ethyl acetate. The organics were dried ($MgSO_4$) then concentrated under reduced pressure. The residue was purified by column chromatography (silica gel, gradient of 0-5% methanol in dichloromethane) to give the title compound as a purple solid (0.41 g, 72%).

Example 4

5-Chloro-4-methyl-7-nitro-2H-benzo[b][1,4]oxazin-3(4H)-one

Methyl iodide (2.15 mmol, 0.13 mL) was added to a suspension of 5-chloro-7-nitro-2H-benzo[b][1,4]oxazin-3(4H)-one (1.79 mmol, 0.41 g) and potassium carbonate (3.58 mmol, 0.49 g) in DMF (5 mL). The mixture was stirred at room temperature for 6 hours then poured into water and extracted with ethyl acetate. The organic extracts were dried ($MgSO_4$) and concentrated under reduced pressure to give the title compound as a dark solid (0.39 g, 90%).

Example 5

7-Amino-5-chloro-4-methyl-2H-benzo[b][1,4]oxazin-3(4H)-one

Iron powder (8.08 mmol, 0.45 g) was added to a solution of 5-chloro-4-methyl-7-nitro-2H-benzo[b][1,4]oxazin-3(4H)-one (1.62 mmol, 0.39 g) in ethanol (15 mL) and 20% aqueous AcOH (3 mL). The mixture was heated at 90° C. for 50 minutes. The mixture was then cooled, diluted with ethyl acetate then filtered through Celite®. The solvents were removed under reduced pressure then the residue was purified by column chromatography (silica gel, gradient of 0-5% methanol in dichloromethane) to give the title compound as dark oil (0.27 g, 78%).

Example 6

7-Amino-2,2-difluoro-4-methyl-2H-benzo[b][1,4]oxazin-3(4H)-one

Triethylamine (25.8 mmol, 3.6 mL) was added to an ice-cooled solution of 2-amino-5-nitrophenol (12.97 mmol, 2.0 g) in dry THF (25 mL). 2-Bromo-2,2-difluoroacetyl chloride (14.4 mmol, 1.36 mL) was added drop-wise and the suspension was allowed to warm to room temperature and stirred for 18 hours. The mixture was diluted with ethyl acetate and the solution washed with water, saturated ammonium chloride solution, saturated sodium bicarbonate solution, and dried (MgSO$_4$). Removal of the solvent under reduced pressure gave an orange solid, which was re-dissolved in DMF (30 mL). Potassium carbonate (36.30 mmol, 5.00 g) was added and the suspension was heated at 50° C. with stirring for 18 h. After cooling to room temperature the mixture was diluted with water and extracted with ethyl acetate. The organic extract was washed with brine and dried (MgSO$_4$). Removal of the solvent under reduced pressure give crude 7-nitro-2,2-difluoro-2H-benzo[b][1,4]oxazin-3(4H)-one as black oil (0.72 g, 24%). Alkylation of this material with methyl iodide using a similar procedure to that for Example 4, followed by reduction using a similar procedure to that for Example 5 gave the title compound (0.25 g, 37%).

Example 7

7-Amino-4-ethyl-2H-benzo[b][1,4]oxazin-3(4H)-one

Using a similar procedure to that for Example 2, the title compound was prepared from 7-amino-2H-benzo[b][1,4]oxazin-3(4H)-one and ethyl iodide in 76% yield.

Example 8

Oxetan-3-ylmethyl methanesulfonate

Triethylamine (10.8 mmol, 1.5 mL) was added to an ice-cooled solution of 3-oxetane methanol (5.20 mmol, 0.46 g) in dichloromethane (5 mL) followed by methanesulfonyl chloride (6.20 mmol, 0.48 mL). After stirring for 72 hours, the mixture was diluted with dichloromethane and washed with saturated sodium bicarbonate solution. The solution was dried (MgSO$_4$) and concentrated under reduced pressure to give the title compound as colourless oil (0.78 g, 89%).

Example 9

7-Amino-4-(oxetan-3-ylmethyl)-2H-benzo[b][1,4]oxazin-3(4H)-one

Alkylation of 7-nitro-2H-benzo[b][1,4]oxazin-3(4H)-one with oxetan-3-ylmethyl methanesulfonate using a similar procedure to Example 4 followed by reduction using a similar procedure to that for Example 5 gave the title compound in 69% yield.

Example 10

7-Amino-4-(2-hydroxy-2-methylpropyl)-2H-benzo[b][1,4]oxazin-3(4H)-one

Alkylation of 7-nitro-2H-benzo[b][1,4]oxazin-3(4H)-one with isobutylene oxide using a similar procedure to Example 4 followed by reduction using a similar procedure to that for Example 5 gave the title compound in 15% yield.

Example 11

7-Amino-4-(2-fluoroethyl)-2H-benzo[b][1,4]oxazin-3(4H)-one

Alkylation of 7-nitro-2H-benzo[b][1,4]oxazin-3(4H)-one with 1-fluoro-2-iodoethane using a similar procedure to Example 4 followed by reduction using a similar procedure to that for Example 5 gave the title compound in 93% yield.

Example 12

7-Amino-4-(2,2-difluoroethyl)-2H-benzo[b][1,4]oxazin-3(4H)-one

Alkylation of 7-nitro-2H-benzo[b][1,4]oxazin-3(4H)-one with 2-iodo-1,1-difluoroethane using a similar procedure to Example 4 followed by reduction using a similar procedure to that for Example 5 gave the title compound in 82% yield.

Example 13

7-Amino-6-chloro-4-methyl-2H-benzo[b][1,4]oxazin-3(4H)-one

Using a similar procedure to that for Example 1, the title compound was prepared from 7-amino-6-chloro-2H-benzo[b][1,4]oxazin-3(4H)-one in 73% yield.

Example 14

7-Amino-4-cyclopropyl-2H-benzo[b][1,4]oxazin-3(4H)-one

A suspension of 7-nitro-2H-1,4-benzoxazin-3-(4H)-one (1.44 mmol, 0.28 g), cyclopropylboronic acid (2.91 mmol, 0.25 g), 4-dimethylaminopyridine (4.34 mmol, 0.53 g), sodium hexamethyldisilazide (1.44 mmol, 0.26 g) and copper(II) acetate (1.44 mmol, 0.26 g) in toluene (5 mL) was heated at 95° C. in a sealed tube under air for 18 hours. After cooling, additional copper(II) acetate (1.1 mmol, 0.20 g), cyclopropylboronic acid (2.33 mmol, 0.20 g), and toluene (5 mL) were added and heating was continued under air at 95° C. for 1 hour. The mixture was cooled to room temperature and diluted with ethyl acetate and water. The organic phase was separated and the aqueous phase re-extracted with ethyl acetate. The combined organic extracts were washed with dilute aqueous hydrochloric acid (2M), then dried (MgSO$_4$) and concentrated under reduced pressure to give 7-nitro-4-cyclopropyl-2H-benzo[b][1,4]oxazin-3(4H)-one (0.28 g, 83%), which was re-dissolved in ethanol (15 mL) and water (1.5 mL). Iron powder (6.0 mmol, 0.33 g) and ammonium chloride (10.8 mmol, 0.58 g) were added and the suspension was heated at 80° C. with vigorous stirring for 90 minutes. The mixture was cooled to room temperature and filtered through Celite®. The filtrate was evaporated and the crude product re-suspended in ethyl acetate. The suspension was washed with saturated aqueous sodium bicarbonate solution, dried (MgSO$_4$) and concentrated under reduced pressure to give the title compound as a yellow solid (0.20 g, 81%).

Example 15

7-Amino-6-chloro-1-methyl-1H-pyrido[2,3-b][1,4]oxazin-2(3H)-one

Benzophenone imine (2.16 mmol, 0.36 mL) was added to a degassed suspension of 7-bromo-6-chloro-1-methyl-1H-pyrido[2,3-b][1,4]oxazin-2(3H)-one (1.80 mmol, 0.50 g), palladium acetate (5 mol %, 20 mg), (±)-BINAP (10 mol %, 120 mg) and NaOtBu (3.6 mmol, 1.17 g) in THF (20 mL). The mixture was heated in a microwave reactor at 100° C. for 90 minutes the cooled and filtered through Celite®. Aqueous hydrochloric acid (2M, 10 mL) was added and the mixture was stirred for 1 hour. The solution was concentrated under reduced pressure then the residue was taken up in 2M HCl and washed with diethyl ether. The aqueous phase was basified (5M NaOH) then extracted with dichloromethane. The organic extract was dried (MgSO$_4$) then concentrated under reduced pressure to give the crude title compound which was used without further purification (0.32 g, 83%).

Example 16

7-Amino-1-methyl-1H-pyrido[2,3-b][1,4]oxazin-2(3H)-one

Ammonium formate (5.96 mmol, 0.38 g) then 10% palladium on carbon (0.05 g) were added to a solution of 7-amino-6-chloro-1-methyl-1H-pyrido[2,3-b][1,4]oxazin-2(3H)-one (1.49 mmol, 0.32 g) in methanol (3 mL). The mixture was heated in a microwave reactor at 100° C. for 15 minutes then cooled and filtered through Celite®. The solution was concentrated under reduced pressure and the residue partitioned between ethyl acetate and 10% aqueous sodium carbonate solution. The organic extract was dried (MgSO$_4$) and concentrated under reduced pressure to give the title compound which was used without further purification (0.13 g, 48%).

Example 17

Oxazolo[4,5-b]pyridin-2(3H)-one

A suspension of carbonyl diimidazole (118.2 mmol, 19.1 g) and 2-amino-3-hydroxy-pyridine (90.9 mmol, 10.00 g) in THF (100 mL) was heated at reflux for 1.5 hours. The mixture was cooled and concentrated under reduced pressure. The residue was taken up in dichloromethane and extracted with 2M aqueous sodium hydroxide solution. The aqueous phase was cooled (ice/water bath) and acidified to pH5 with concentrated hydrochloric acid. The resulting precipitate was isolated by filtration, washed with water and THF then dried under suction to give the title compound as a grey powder (8.81 g, 71%).

Example 18

6-Nitrooxazolo[4,5-b]pyridin-2(3H)-one

Fuming nitric acid (27 mL) was added drop-wise to a suspension of oxazolo[4,5-b]pyridin-2(3H)-one (96.98 mmol, 13.19 g) in concentrated sulphuric acid (30 mL), cooled in an ice/water bath, over 10 minutes. The resulting solution was heated at 45° C. overnight then cooled and poured into an ice/water with vigorous stirring. The resulting precipitate was isolated by filtration, washed with water then dried under suction to give the title compound as a beige powder (7.00 g, 40%).

Example 19

2-Amino-5-nitropyridin-3-ol

10% Aqueous sodium hydroxide solution (44.40 mmol, 17.8 mL) was added to a suspension of 6-nitrooxazolo[4,5-b]pyridin-2(3H)-one (11.10 mmol, 2.00 g) in THF (10 mL). The mixture was heated at 85° C. for 2 hours. The mixture was cooled (ice/water bath) then acidified to pH6 (concentrated hydrochloric acid). The resulting precipitate was isolated by filtration, washed with water then dried under suction to give the title compound as an orange powder (4.30 g, 37%).

Example 20

7-Nitro-2H-pyrido[3,2-b][1,4]oxazin-3(4H)-one

Methyl bromoacetate (39.22 mmol, 3.71 mL) was added drop-wise to a suspension of 2-amino-5-nitropyridin-3-ol (35.66 mmol, 5.53 g) and potassium fluoride (89.15 mmol, 5.17 g) in DMF (50 mL). The mixture was heated at 65° C. for 5 hours then cooled and poured into ice/water with stirring. The resulting precipitate was isolated by filtration, washed with water then dried under suction to give the title compound as a beige powder (6.45 g, 93%).

Example 21

4-Methyl-7-nitro-2H-pyrido[3,2-b][1,4]oxazin-3(4H)-one

Methyl iodide (30.83 mmol, 1.92 mL) was added drop-wise over 5 minutes to a suspension of 7-nitro-2H-pyrido[3,2-b][1,4]oxazin-3(4H)-one (25.69 mmol, 5.01 g) and potassium carbonate (51.38 mmol, 7.09 g) in DMF (45 mL). The mixture was stirred for 5.5 hours, poured into water then extracted with ethyl acetate. The combined organic extracts were dried (MgSO$_4$) then concentrated under reduced pressure. The residue was triturated (diethyl ether containing a few drops of methanol) then dried under suction to give the title compound as a beige solid (3.66 g, 68%).

Example 22

7-Amino-4-methyl-2H-pyrido[3,2-b][1,4]oxazin-3(4H)-one

Iron powder (87.55 mmol, 4.90 g) was added to a suspension of 4-methyl-7-nitro-2H-pyrido[3,2-b][1,4]oxazin-3(4H)-one (17.51 mmol, 3.66 g) in ethanol (60 mL) and 20% (v/v) aqueous acetic acid (15 mL) under N$_2$. The mixture was heated at reflux for 30 minutes then cooled and diluted with ethyl acetate then dried over MgSO$_4$ for 30 minutes. The resulting suspension was filtered through Celite® then concentrated under reduced pressure. The residue was triturated with diethyl ether then dried under reduced pressure to give the title compound as a cream solid (2.43 g, 77%).
$^1$H NMR (400 MHz, d6-DMSO) 7.42 (1H, d, J=2.3 Hz), 6.65 (1H, d, J=2.3 Hz), 5.19 (2H, s), 4.65 (2H, s), 3.27 (3H, s).

Example 23

7-Amino-4-ethyl-2H-pyrido[3,2-b][1,4]oxazin-3(4H)-one

Alkylation of 7-nitro-2H-pyrido[3,2-b][1,4]oxazin-3(4H)-one with ethyl iodide using a similar procedure to that for Example 21 followed by reduction using a similar procedure to that for Example 22 gave the title compound in 63% yield.

Example 24

6-Chloro-1-methyl-1H-pyrido[2,3-b][1,4]oxazin-2(3H)-one

7-Bromo-6-chloro-1-methyl-1H-pyrido[2,3-b][1,4]oxazin-2(3H)-one (3.99 mmol, 1.10 g) was added to a suspension of zinc dust (15.96 mmol, 1.04 g) in saturated aqueous ammonium chloride solution (15 mL) and THF (15 mL) and the mixture was stirred vigorously overnight. The mixture was filtered through Celite® then the filtrate was concentrated under reduced pressure. The residue was suspended in water then filtered. The collected solid was washed with water then diethyl ether and dried under vacuum to give the title compound as a white solid (0.72 g, 92%).

Example 25

6-Amino-1-methyl-1H-pyrido[2,3-b][1,4]oxazin-2(3H)-one

A degassed suspension of 6-chloro-1-methyl-1H-pyrido[2,3-b][1,4]oxazin-2(3H)-one (2.52 mmol, 0.5 g), benzophenone imine (3.03 mmol, 0.51 mL), palladium acetate (5 mol %, 28 mg), (±)-BINAP (0.25 mmol, 157 mg) and cesium carbonate (5.04 mmol, 1.64 g) in THF (20 mL) was heated in a microwave reactor for 2 hours (conversion incomplete). The mixture was filtered through Celite® then HCl (2N, 10 mL) was added. The mixture was stirred for 1.5 hours. The mixture was concentrated in vacuo then the residue suspended between ethyl acetate and 2M aqueous hydrochloric acid. The aqueous layer was cooled (ice/water bath) then extracted with dichloromethane. The organic extracts were dried (MgSO$_4$) and concentrated under reduced pressure to give the title compound as a yellow solid (0.19 g, 43%).

Example 26

4-Chloro-5-nitropyridin-2-ol

Ammonia gas (100 mL) was condensed into THF (300 mL) at −78° C. in a cardice/acetone bath. Potassium tert-butoxide (395 mmol, 44.25 g) was then added portion-wise with stirring. After 5 minutes, the cardice bath was lowered so only the bottom quarter of the flask was immersed and stirring was continued for a further 20 minutes. Concurrently, tert-butyl hydroperoxide (158 mmol, 26.3 mL) was added to a suspension of 4-chloro-3-nitropyridine (158 mmol, 25 g) in THF (100 mL) cooled in an ice/water bath. This mixture was stirred for 45 minutes then transferred to a dropping funnel and added drop-wise over 1.25 hours to the ammonia solution prepared above. The mixture was stirred for a further 3 hours then saturated aqueous ammonium chloride solution (35 mL) was added carefully. The mixture was allowed to warm to room temperature overnight allowing the ammonia to vent to atmosphere. The solvents were then removed under reduced pressure and the residue triturated with ice-cold saturated aqueous ammonium chloride solution (50 mL). The resulting solid was collected by filtration, washed with ice-cold water (2×50 mL) then dried under suction prior to further drying by azeotroping with toluene (5×100 mL) then in a vacuum oven at 40° C. overnight to give the title compound as a brown solid (24.96 g, 90%).

Example 27

2,4-Dichloro-5-nitropyridine

A suspension of 2-hydroxy-4-chloro-5-nitropyridine (86.2 mmol, 15 g) in phosphorus oxychloride (50 mL) was heated at 80° C. for 3.5 hours. The excess phosphorus oxychloride was removed under reduced pressure and the residue partitioned between dichloromethane and 10% aqueous sodium carbonate solution. The aqueous phase was further extracted with dichloromethane (3×100 mL). The combined organic extracts were dried (MgSO$_4$) then concentrated under reduced pressure to give the title compound as dark oil which solidified on standing (7.19 g, 43%).

Example 28

Methyl 2-((2-chloro-5-nitropyridin-4-yl)oxy)acetate

Sodium hydride (60% in mineral oil, 31.2 mmol, 1.25 g) was added to a solution of 2,4-dichloro-5-nitropyridine (26 mmol, 5.00 g) and methyl glycolate (31.2 mmol, 2.41 mL) in DMF (50 mL) cooled in an ice-water bath. The mixture was stirred overnight then poured into saturated aqueous ammonium chloride solution (30 mL). The mixture was extracted with ethyl acetate (3×50 mL). The combined organic extracts were dried (MgSO$_4$) then concentrated under reduced pressure to give dark oil which solidified on standing. The solid was triturated with isohexane containing a few drops of dichloromethane then filtered and dried under suction to give the title compound as a dark brown solid (4.32 g, 67%).

Example 29

7-Chloro-2H-pyrido[4,3-b][1,4]oxazin-3(4H)-one

Iron powder (87.5 mmol, 4.90 g) was added to a suspension of methyl 2-((2-chloro-5-nitropyridin-4-yl)oxy)acetate (17.5 mmol, 4.32 g) in ethanol (80 mL) and 20% (v/v) acetic acid (15 mL) under nitrogen. The mixture was heated to 80° C. for 20 hours at which point it was cooled to room temperature and diluted with ethyl acetate (100 mL). The mixture was filtered through Celite® then concentrated under reduced pressure to give the title compound as a pale solid (3.18 g, 98%).

Example 30

7-Chloro-4-methyl-2H-pyrido[4,3-b][1,4]oxazin-3(4H)-one

Potassium carbonate (34.6 mmol, 4.77 g) then methyl iodide (20.8 mmol, 1.29 mL) were added to a solution of 7-chloro-2H-pyrido[4,3-b][1,4]oxazin-3(4H)-one (17.3 mmol, 3.18 g) in DMF (30 mL). The mixture was stirred for 18 hours then partitioned between water (30 mL) and ethyl acetate (60 mL). The aqueous phase was extracted with ethyl acetate (3×50 mL). The combined organic extracts were dried (MgSO$_4$) and concentrated under reduced pressure to give the title compound as a brown solid (2.72 g, 79%).

Example 31

7-Amino-4-methyl-2H-pyrido[4,3-b][1,4]oxazin-3(4H)-one hydrochloride

A solution of 7-chloro-4-methyl-2H-pyrido[4,3-b][1,4]oxazin-3(4H)-one (13.75 mmol, 2.72 g), and benzophenone imine (16.50 mmol, 2.76 mL) in toluene (100 mL) was purged with nitrogen for 10 minutes. Sodium tert-butoxide (20.62 mmol, 1.98 g), (±)-BINAP (0.55 mmol, 0.34 g) and tris(dibenzylidineacetone)dipalladium (0.275 mmol, 0.25 g) were added and the mixture heated at 100° C. for 18 hours. The mixture was partitioned between water (50 mL) and ethyl acetate (50 mL) then the aqueous phase was extracted with ethyl acetate (3×50 mL). The combined organic extracts were dried (MgSO$_4$) and concentrated under reduced pressure to give brown oil which was purified by column chromatography (silica gel, 4% methanol in dichloromethane). The purified product was dissolved in THF (15 mL) and 2M aqueous hydrochloric acid (1 mL) was added. The mixture was stirred for 10 hours then filtered. The solid was washed with THF then dried under suction to give the title compound (0.76 g, 26%).

Example 32

6-Amino-1-methyl-3,4-dihydroquinazolin-2(1H)-one

Sodium hydride (60% in mineral oil, 5.28 mmol, 0.21 g) was added portion-wise to a solution of 6-nitro-3,4-dihydroquinazolin-2(1H)-one (5.28 mmol, 1.02 g) in DMF (15 mL) cooled in an ice/water bath. The mixture was stirred for 5 minutes then methyl iodide (5.28 mmol 0.32 mL) was added drop-wise. The mixture was stirred at room temperature for 3 hours then concentrated under reduced pressure. The residue was suspended in ethanol (40 mL) and water (40 mL). Ammonium chloride (42.24 mmol, 2.24 g) and iron powder (26.40 mmol, 1.48 g) were added and the mixture was heated at 90° C. for 2.5 hours. The mixture was cooled, filtered through Celite® and concentrated under reduced pressure onto silica gel. Purification by column chromatography (silica gel, gradient of methanol in dichloromethane) gave the title compound as a yellow solid (0.59 g, 63%).

Example 33

3-Ethyl-6-nitroquinazolin-4(3H)-one

Ethyl iodide (2.88 mmol, 0.23 mL) was added drop-wise to a suspension of 6-nitroquinazolin-4(3H)-one (2.62 mmol, 0.50 g) and potassium carbonate (2.88 mmol, 0.40 g) in DMF (10 mL) cooled in an ice/water bath. The resulting mixture was stirred for 4 hours then diluted with ethyl acetate and filtered through Celite®. The solvents were removed under reduced pressure to give the crude title compound as a yellow powder (0.97 g, >100%).

Example 34

6-Amino-3-ethylquinazolin-4(3H)-one

Iron powder (13.10 mmol, 0.73 g) was added to a solution of 3-ethyl-6-nitroquinazolin-4(3H)-one (ca. 2.62 mmol) and 20% aqueous acetic acid (3 mL) in ethanol (20 mL). The mixture was heated at 85° C. for 40 minutes then cooled to room temperature and diluted with ethyl acetate. The mixture was filtered through Celite® then the solvents removed under reduced pressure. The residue was triturated with diethyl ether, washed with water and dried under suction to give the title compound as a beige solid (0.33 g, 67%).
$^1$H NMR (400 MHz, d6-DMSO) 8.08 (1H, s), 7.40 (1H, d, J=8.6 Hz), 7.24 (1H, d, J=2.5 Hz), 7.09 (1H, dd, J=2.8, 8.6 Hz), 5.66 (2H, s), 3.97 (2H, q, J=7.1 Hz), 1.28 (3H, t, J=7.1 Hz).

Example 35

2-Chloro-N-(cyclopropylmethyl)-5-nitropyridin-4-amine

Cyclopropylmethylamine (45.73 mmol, 3.96 mL) was added dropwise over 5 minutes to a solution of 2, 4-dichloro-5-nitropyridine (41.67 mmol, 8.00 g) and DIPEA (56.20 mmol, 9.77 mL) in dichloromethane (100 mL) cooled in an ice/water bath. The resulting green/brown suspension was stirred for 20 hours at room temperature. The mixture was diluted with dichloromethane then washed with saturated aqueous ammonium chloride then brine, dried over MgSO$_4$ then concentrated under reduced pressure to give a yellow solid. This was washed with water and dried under suction to give the title compound (8.79 g, 93%).

Example 36

6-Chloro-1-(cyclopropylmethyl)-1H-imidazo[4,5-c]pyridine

Iron powder (58.03 mmol, 3.24 g) was stirred in glacial AcOH (65 mL) at 80° C. for 30 minutes after which a solution of 2-chloro-N-(cyclopropylmethyl)-5-nitropyridin-4-amine (17.39 mmol, 3.96 g) in acetic acid (65 mL) was added drop-wise over 30 minutes. The mixture was heated at 80° C. for 1 hour then filtered hot through Celite®, washing with hot acetic acid then ethyl acetate. The solvents were removed under reduced pressure then the residue was suspended in ethyl acetate and saturated aqueous sodium bicarbonate solution. The suspension was filtered then the phases were separated. The aqueous phase was extracted with ethyl acetate. The combined organic extracts were dried (MgSO$_4$) then concentrated under reduced pressure to give brown oil. This was suspended in trimethylorthoformate (70 mL) and formic acid (1.5 mL) then heated at 100° C. for 3 hours. The mixture was cooled then concentrated under reduced pressure. The residue was partitioned between ethyl acetate and saturated aqueous sodium bicarbonate solution. The organic extracts were dried (MgSO$_4$) then concentrated under reduced pressure to give brown oil. This was purified by column chromatography (silica gel, gradient of 0.5-8% methanol in dichloromethane) to give the title compound as brown oil which solidified on standing (1.04 g, 29%).

Example 37

4-Cyclopropyl-7-((1-(cyclopropylmethyl)-1H-imidazo[4,5-c]pyridin-6-yl)amino)-2H-benzo[b][1,4]oxazin-3(4H)-one

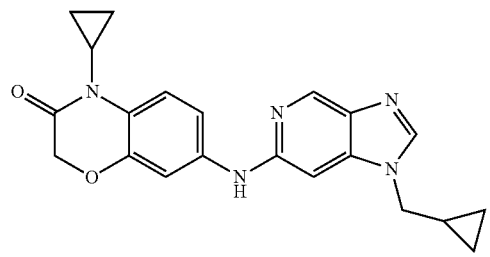 [SMILES: O=C1COc2cc(Nc3cc4c(cn3)ncn4CC3CC3)ccc2N1C1CC1]

6-Chloro-1-(cyclopropylmethyl)-1H-imidazo[4,5-c]pyridine (0.45 mmol, 0.093 g), 7-amino-4-cyclopropyl-2H-benzo[b][1,4]oxazin-3(4H)-one (0.54 mmol, 0.11 g), Cs$_2$CO$_3$ (0.90 mmol, 0.30 g), Xantphos (0.045 mmol, 0.026 g) and Pd$_2$(dba)$_3$ (0.022 mmol, 0.021 g) in dioxane (2.5 mL) were combined and heated with vigorous stirring at 120° C. for 30 min in the microwave; alternatively, the mixture was heated at 90° C. using conventional heating for 18 hours. The mixture was filtered through Celite®, washed with dichloromethane and the filtrate was concentrated under reduced pressure. The crude product was purified using preparative HPLC to give the title compound as an off-white solid (0.0087 g, 5%).

Example 38

7-((1-(Cyclopropylmethyl)-1H-imidazo[4,5-c]pyridin-6-yl)amino)-2,2-difluoro-4-methyl-2H-benzo[b][1,4]oxazin-3(4H)-one Using a similar procedure to that for Example 37, the title compound was prepared from 7-amino-2,2-difluoro-4-methyl-2H-benzo[b][1,4]oxazin-3(4H)-one and 6-chloro-1-(cyclopropylmethyl)-1H-imidazo[4,5-c]pyridine in 35% yield.

Example 39

7-((1-(Cyclopropylmethyl)-1H-imidazo[4,5-c]pyridin-6-yl)amino)-4-methyl-2H-pyrido[3,2-b][1,4]oxazin-3(4H)-one Using a similar procedure to that for Example 37, the title compound was prepared from 7-amino-4-methyl-2H-pyrido[3,2-b][1,4]oxazin-3(4H)-one and 6-chloro-1-(cyclopropylmethyl)-1H-imidazo[4,5-c]pyridine in 34% yield.
$^1$H NMR (400 MHz, d6-DMSO) 9.04 (1H, s), 8.60 (1H, s), 8.22-8.18 (2H, m), 7.92 (1H, d, J=2.1 Hz), 6.96 (1H, s), 4.74 (2H, s), 4.05 (2H, d, J=7.0 Hz), 1.30-1.16 (1H, m), 0.61-0.55 (2H, m), 0.46-0.40 (2H, m).

Example 40

6-((1-(Cyclopropylmethyl)-1H-imidazo[4,5-c]pyridin-6-yl)amino)-1-methyl-3,4-dihydroquinazolin-2(1H)-one Using a similar procedure to that for Example 37, the title compound was prepared from 6-amino-1-methyl-3,4-dihydroquinazolin-2(1H)-one and 6-chloro-1-(cyclopropylmethyl)-1H-imidazo[4,5-c]pyridine in 9% yield.

Example 41

6-Bromo-1-(cyclopropylmethyl)-1H-imidazo[4,5-b]pyrazine

A solution of 3,5-dibromopyrazin-2-amine (3.97 mmol, 1.00 g), cyclopropylmethylamine (4.36 mmol, 0.38 mL) and diisopropylethylamine (4.36 mmol, 0.78 mL) in ethanol (10 mL) was heated at 150° C. in a microwave reactor for 30 minutes then at 170° C. for 30 minutes. A further 0.17 mL (1.98 mmol) of cyclopropylmethylamine was added and the mixture was heated at 170° C. for a further 1.5 hours. The solvents were removed under reduced pressure and the residue taken up in ethyl acetate (20 mL). The organic extracts were washed with water, dried (MgSO$_4$) and concentrated under reduced pressure to give dark oil which was dissolved in trimethylorthoformate (20 mL). Catalytic para-toluene sulfonic acid monohydrate was added and the mixture was heated to 90° C. for 2 hours. The solvents were removed under reduced pressure and the residue purified by column chromatography (silica gel, gradient of 10-75% ethyl acetate in isohexane) to give the title compound as a white solid (0.589 g, 59%).

Example 42

7-((1-(Cyclopropylmethyl)-1H-imidazo[4,5-b]pyrazin-6-yl)amino)-4-methyl-2H-benzo[b][1,4]oxazin-3(4H)-one

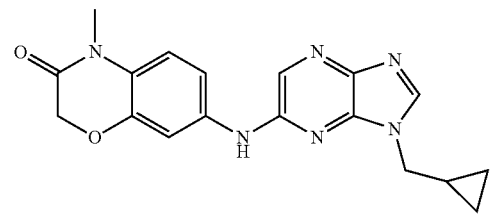 [SMILES: CN1C(=O)COc2cc(Nc3cnc4ncn(CC5CC5)c4n3)ccc21]

Using a similar procedure to that for Example 37, the title compound was prepared from 7-amino-4-methyl-2H-benzo[b][1,4]oxazin-3(4H)-one and 6-bromo-1-(cyclopropylmethyl)-1H-imidazo[4,5-b]pyrazine in 78% yield.

Example 43

6-((1-(Cyclopropylmethyl)-1H-imidazo[4,5-b]pyrazin-6-yl)amino)-3-methylbenzo[d]oxazol-2(3H)-one

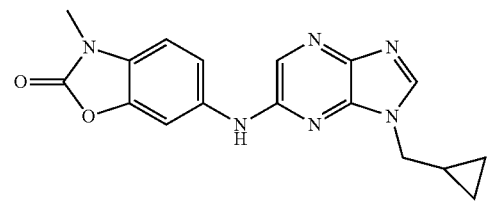 [SMILES: Cn1c(=O)oc2cc(Nc3cnc4ncn(CC5CC5)c4n3)ccc21]

Using a similar procedure to that for Example 37, the title compound was prepared from 6-amino-3-methylbenzo[d]oxazol-2(3H)-one and 6-bromo-1-(cyclopropylmethyl)-1H-imidazo[4,5-b]pyrazine in 20% yield.

Example 44

2-Chloro-9-(cyclopropylmethyl)-9H-purine

Cyclopropylmethylamine (10.32 mmol, 0.73 g) was added drop-wise to a solution of 2, 4-dichloro-5-nitropyrimidine (5.16 mmol, 1.00 g) in THF (5 mL), cooled in an ice-water bath, over 5 minutes. The resulting suspension was stirred for 20 hours at room temperature then the solvents were removed under reduced pressure. The residue was partitioned between ethyl acetate and water then the aqueous phase was extracted with ethyl acetate. The combined organic extracts were dried (MgSO$_4$) then concentrated under reduced pressure to give a brown gum (1.81 g). This was suspended in ethanol (100 mL) and water (10 mL) and ammonium chloride (42.99 mmol, 2.30 g) and iron powder (25.06 mmol, 1.40 g) were added. The mixture was heated at 95° C. for 1.5 hours then cooled. Trimethylorthoformate (30 mL) was added followed by catalytic para-toluene sulfonic acid monohydrate and the mixture was heated at 105° C. for 7 hours. The mixture was cooled, filtered then concentrated under reduced pressure onto silica gel. Partial purification by column chromatography (silica gel, gradient of 5-100% ethyl acetate in isohexane) gave the product (0.17 g) which was used without further purification.

Example 45

7-((9-(cyclopropylmethyl)-9H-purin-2-yl)amino)-4-methyl-2H-benzo[b][1,4]oxazin-3(4H)-one Using a similar procedure to that for Example 37, the title compound was prepared from 7-amino-4-methyl-2H-benzo[b][1,4]oxazin-3(4H)-one and 2-chloro-9-(cyclopropylmethyl)-9H-purine in 34% yield.
$^1$H NMR (400 MHz, CDCl$_3$) 8.81 (1H, s), 7.95 (1H, s), 7.59 (1H, d, J=2.5 Hz), 7.26-7.20 (2H, m), 6.94 (1H, d, J=8.6 Hz), 4.64 (2H, s), 4.03 (2H, d, J=7.1 Hz), 3.38 (3H, s), 1.39-1.30 (1H, m), 0.75-0.69 (2H, m), 0.52-0.48 (2H, m).

Example 46

7-((9-(Cyclopropylmethyl)-9H-purin-2-yl)amino)-4-(2-methoxyethyl)-2H-benzo[b][1,4]oxazin-3(4H)-one

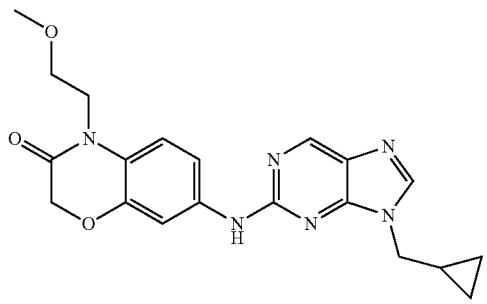 [SMILES: COCCN1C(=O)COc2cc(Nc3ncc4ncn(CC5CC5)c4n3)ccc21]

Using a similar procedure to that for Example 37, the title compound was prepared from 7-amino-4-(2-methoxyethyl)-2H-benzo[b][1,4]oxazin-3(4H)-one and 2-chloro-9-(cyclopropylmethyl)-9H-purine in 35% yield.

Example 47

3-Oxocyclobutanecarbonitrile

Sodium periodate (43.0 mmol, 9.20 g) was added portionwise to a solution of 3-methylenecyclobutanecarbonitrile (21.5 mmol, 2.00 g) and ruthenium trichloride (0.47 mmol, 98 mg) in dichloromethane:acetonitrile:water (1:1:1.5; 175 mL). The resulting suspension was vigorously stirred overnight. The organic phase was separated then the aqueous phase was further extracted with dichloromethane (3×50 mL). The combined organic extracts were dried (MgSO$_4$) then passed through a silica plug. The solvents were removed under reduced pressure to give the title compound as a dark solid (1.58 g, 74%).

Example 48

3,3-Difluorocyclobutanecarbonitrile

Diethylaminosulfur trifluoride (32.10 mmol, 4.24 mL) was added drop-wise to a solution of 3-oxocyclobutanecarbonitrile (16.00 mmol, 1.52 g) in dichloromethane (50 mL) under N$_2$ over 5 minutes. The mixture was allowed to warm to room temperature then stirred overnight. A further 2.12 mL of diethylaminosulfur trifluoride was added then the mixture was heated at reflux for 4 hours then allowed to cool to room temperature. The mixture was poured into ice-cold saturated aqueous sodium bicarbonate solution with vigorous stirring. The organics were isolated by phase separator cartridge then concentrated under reduced pressure without external heating. The crude product was purified by column chromatography (silica gel, diethyl ether) to give the title compound as brown oil (1.72 g, 92%).

Example 49

(3,3-Difluorocyclobutyl)methanamine hydrochloride

Borane-THF (1 M in THF, 16.20 mmol, 16.20 mL) was added drop-wise over 5 minutes to a solution of 3,3-difluorocyclobutanecarbonitrile (14.70 mmol, 1.72 g) in THF (5 mL) under N$_2$. The resulting solution was then heated to reflux for 20 hours then cooled in an ice-water bath. Methanol (20 mL) was added drop-wise. The resulting mixture was concentrated under reduced pressure. The residue was dissolved in methanol (10 mL) and concentrated hydrochloric acid (10 mL) and heated at reflux for 2 hours. The mixture was concentrated under reduced pressure and the residue azeotroped twice with ethanol before being suspended in diethyl ether. The resulting cream solid was isolated by filtration and dried under suction to give the title compound as a white solid (1.48 g, 64%).

Example 50

5-Bromo-N-((3,3-difluorocyclobutyl)methyl)-5-fluoro-2-nitroaniline

A solution of (3,3-difluorocyclobutyl)methanamine hydrochloride (2.32 mmol, 0.36 g), 2,5-difluoro-4-bromonitrobenzene (2.11 mmol, 0.50 g) and diisopropylethylamine (1.10 mL) in DMF (10 mL) was heated at 90° C. for 4 hours then cooled to room temperature and diluted with ethyl acetate (30 mL). The organic extracts were washed with water, dried (MgSO$_4$) and concentrated under reduced pressure to give the title compound as orange oil (0.68 g, 95%) which was used without further purification.

Example 51

6-Bromo-1-((3,3-difluorocyclobutyl)methyl)-5-fluoro-1H-benzo[d]imidazole

Iron powder (10.05 mmol, 0.59 g) was added in one portion to a rapidly stirred suspension of 5-bromo-N-((3,3-difluorocyclobutyl)methyl)-5-fluoro-2-nitroaniline (2.01 mmol, 0.68 g) in ethanol (15 mL) and 20% aqueous acetic acid (3 mL). The mixture was heated to 90° C. for 30 minutes then cooled to room temperature and diluted with ethyl acetate (80 mL) with stirring. The resulting suspension was filtered through Celite® eluting with ethyl acetate. The solvents were removed under reduced pressure to give gold-coloured oil which was dissolved in trimethylorthoformate (15 mL). Catalytic para-toluene sulfonic acid monohydrate was added and the mixture was heated at 90° C. overnight. The solvents were removed under reduced pressure and the residue was purified by column chromatography (silica gel, gradient of 20-75% ethyl acetate in isohexane) to give the title compound as a white solid (0.49 g, 76%).

Example 52

7-((1-((3,3-Difluorocyclobutyl)methyl)-5-fluoro-1H-benzo[d]imidazol-6-yl)amino)-4-methyl-2H-pyrido[3,2-b][1,4]oxazin-3(4H)-one

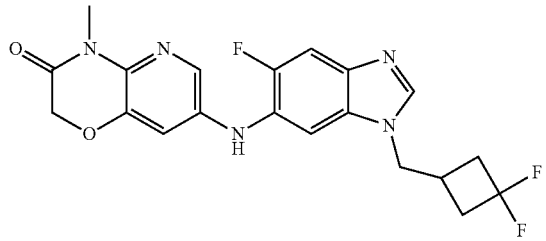 [SMILES: CN1C(=O)COc2cc(Nc3cc4c(cc3F)ncn4CC3CC(F)(F)C3)cnc21]

Using a similar procedure to that for Example 37, the title compound was prepared from 7-amino-4-methyl-2H-pyrido[3,2-b][1,4]oxazin-3(4H)-one and 6-Bromo-1-((3,3-difluorocyclobutyl)methyl)-5-fluoro-1H-benzo[d]imidazole in 43% yield.

$^1$H NMR (400 MHz, DMSO D6) 8.24 (1H, s), 8.04 (1H, s), 7.81 (1H, d, J=2.3 Hz), 7.56-7.51 (2H, m), 7.00 (1H, d, J=2.3 Hz), 4.71 (2H, s), 4.33 (2H, d, J=5.8 Hz), 3.31 (3H, s), 2.68-2.55 (3H, m), 2.47-2.36 (2H, m).

Example 53

6-Chloro-N-((3,3-difluorocyclobutyl)methyl)-2-methyl-3-nitropyridin-4-amine (3,3-Difluorocyclobutyl)methanamine hydrochloride (3.98 mmol, 0.63 g) was added portion-wise to a solution of 3-nitro-4,6-dichloro-2-methyl-pyridine (3.62 mmol, 0.75 g) and diisopropylethylamine (9.05 mmol, 1.57 mL) in dichloromethane (10 mL) cooled in an ice-water bath. The cooling bath was removed and the mixture was stirred for 3.5 hours then diluted with dichloromethane, washed with water, dried (MgSO$_4$) and concentrated under reduced pressure to give the title compound as a yellow solid (0.91 g, 86%).

Example 54

6-Chloro-1-((3,3-difluorocyclobutyl)methyl)-4-methyl-1H-imidazo[4,5-c]pyridine

Using a similar procedure to that for Example 51, the title compound was synthesized from 6-chloro-N-((3,3-difluorocyclobutyl)methyl)-2-methyl-3-nitropyridin-4-amine in 65% yield.

$^1$H NMR (400 MHz, d6-DMSO) 8.46 (1H, s), 7.79 (1H, s), 4.41 (2H, d, J=7.1 Hz), 2.70-2.68 (6H, m), 2.51-2.41 (2H, m).

Example 55

6-((1-((3,3-Difluorocyclobutyl)methyl)-4-methyl-1H-imidazo[4,5-c]pyridin-6-yl)amino)-3-methyl-benzo[d]oxazol-2(3H)-one Using a similar procedure to that for Example 37, the title compound was prepared from 6-amino-3-methylbenzo[d] oxazol-2(3H)-one and 6-chloro-1-((3,3-difluorocyclobutyl) methyl)-4-methyl-1H-imidazo[4,5-c]pyridine in 51% yield.

Example 56

5-Bromo-N-(cyclopropylmethyl)-4-fluoro-2-nitroaniline

Cyclopropylmethylamine (9.3 mmol, 0.81 mL) was added drop-wise to a solution of 4-bromo-2,5-difluoro-1-nitrobenzene (8.4 mmol, 2 g,) and diisopropylethylamine (10.1 mmol, 1.67 mL,) in n-butanol (20 mL). The resulting solution was stirred at 80° C. for 18 hours. The mixture was concentrated under reduced pressure and partitioned between water and dichloromethane. The organic extract was passed through a phase separator column and concentrated under reduced pressure to afford the crude title compound 5-bromo-N-(cyclopropylmethyl)-4-fluoro-2-nitroaniline as a brown solid (2.37 g, 98%) which was used without further purification.

Example 57

6-Bromo-1-(cyclopropylmethyl)-5-fluoro-1H-benzo[d]imidazole

A mixture of 5-bromo-N-(cyclopropylmethyl)-4-fluoro-2-nitroaniline (8.2 mmol, 2.37 g), iron powder (42.8 mmol, 2.39 g), ammonium chloride (74 mmol, 3.96 g) and water (17 mL) in ethanol (170 mL) was heated at 90° C. for 2.5 hours. The suspension was filtered hot through Celite® and the filtrate was concentrated under reduced pressure. The residue was re-suspended in trimethylorthoformate (100 mL) and para-toluene sulfonic acid monohydrate (0.55 g) was added. The suspension was heated at 115° C. for 2 hours then cooled to room temperature and concentrated under reduced pressure. Purification by column chromatography (silica gel, gradient of ethyl acetate in isohexane) gave the title compound as a pink solid (1.72 g, 79%).

Example 58

6-((1-(Cyclopropylmethyl)-5-fluoro-1H-benzo[d] imidazole-6-yl)amino)-4-methyl-2H-benzo[b][1,4] oxazin-3(4H)-one Using a similar procedure to that for Example 37, the title compound was prepared from 6-amino-4-methyl-2H-benzo [b][1,4]oxazin-3(4H)-one and 6-bromo-1-(cyclopropylmethyl)-5-fluoro-1H-benzo[d]imidazole in 34% yield.

Example 59

7-((1-(Cyclopropylmethyl)-5-fluoro-1H-benzo[d] imidazol-6-yl)-4-(2-methoxyethyl)-2H-2H-benzo[b] [1,4]oxazin-3(4H)-one Using a similar procedure to that for Example 37, the title compound was prepared from 7-amino-4-(2-methoxyethyl)-2H-benzo[b][1,4]oxazin-3(4H)-one and 6-bromo-1-(cyclopropylmethyl)-5-fluoro-1H-benzo[d]imidazole in 58% yield.

Example 60

7-((1-(Cyclopropylmethyl)-5-fluoro-1H-benzo[d]imidazol-6-yl)amino)-2H-benzo[b][1,4]oxazin-3(4H)-one Using a similar procedure to that for Example 37, the title compound was prepared from 7-amino-2H-benzo[b][1,4]oxazin-3(4H)-one and 6-bromo-1-(cyclopropylmethyl)-5-fluoro-1H-benzo[d]imidazole in 7% yield.

Example 61

7-((1-(Cyclopropylmethyl)-5-fluoro-1H-benzo[d]imidazol-6-yl)amino)-4-(2,2-difluoroethyl)-2H-benzo[b][1,4]oxazin-3(4H)-one Using a similar procedure to that for Example 37, the title compound was prepared from 7-amino-4-(2,2-difluoroethyl)-2H-benzo[b][1,4]oxazin-3(4H)-one and 6-bromo-1-(cyclopropylmethyl)-5-fluoro-1H-benzo[d]imidazole in 46% yield.

Example 62

6-Chloro-7-((1-(cyclopropylmethyl)-5-fluoro-1H-benzo[d]imidazole-6-yl)amino)-4-methyl-2H-benzo[b][1,4]oxazin-3(4H)-one Using a similar procedure to that for Example 37, the title compound was prepared from 7-amino-6-chloro-4-methyl-2H-benzo[b][1,4]oxazin-3(4H)-one and 6-bromo-1-(cyclopropylmethyl)-5-fluoro-1H-benzo[d]imidazole in 54% yield.

Example 63

7-((1-(Cyclopropylmethyl)-5-fluoro-1H-benzo[d]imidazole-6-yl)amino)-4-methyl-2H-pyrido[4,3-b][1,4]oxazin-3(4H)-one Using a similar procedure to that for Example 37, the title compound was prepared from 7-amino-4-methyl-2H-pyrido[4,3-b][1,4]oxazin-3(4H)-one hydrochloride and 6-bromo-1-(cyclopropylmethyl)-5-fluoro-1H-benzo[d]imidazole in 54% yield.

Example 64

6-Bromo-1-(2-cyclopropylethyl)-5-fluoro-1H-benzo[d]imidazole

Using similar procedures to those for Example 56 and Example 57, the title compound was prepared from 4-bromo-2,5-difluoro-1-nitrobenzene and 2-cyclopropylethanamine in 31% yield.

Example 65

7-((1-(2-Cyclopropylethyl)-5-fluoro-1H-benzo[d]imidazol-6-yl)amino)-4-methyl-2H-benzo[b][1,4]oxazin-3(4H)-one Using a similar procedure to that for Example 37, the title compound was prepared from 7-amino-4-methyl-2H-benzo[b][1,4]oxazin-3(4H)-one and 6-bromo-1-(2-cyclopropylethyl)-5-fluoro-1H-benzo[d]imidazole in 42% yield.

Example 66

7-((1-(2-Cyclopropylethyl)-5-fluoro-1H-benzo[d]imidazol-6-yl)amino)-4-(oxetan-3-ylmethyl)-2H-benzo[b][1,4]oxazin-3(4H)-one Using a similar procedure to that for Example 37, the title compound was prepared from 7-amino-4-(oxetan-3-ylmethyl)-2H-benzo[b][1,4]oxazin-3(4H)-one and 6-bromo-1-(2-cyclopropylethyl)-5-fluoro-1H-benzo[d]imidazole in 27% yield.

Example 67

7-((1-(2-Cyclopropylethyl)-5-fluoro-1H-benzo[d]imidazol-6-yl)amino)-4-methyl-2H-pyrido[3,2-b][1,4]oxazin-3(4H)-one

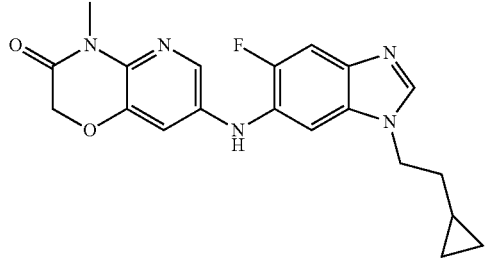 [SMILES: CN1C(=O)COc2cc(Nc3cc4c(cc3F)ncn4CCC3CC3)cnc21]

Using a similar procedure to that for Example 37, the title compound was prepared from 7-amino-4-methyl-2H-pyrido[3,2-b][1,4]oxazin-3(4H)-one and 6-bromo-1-(2-cyclopropylethyl)-5-fluoro-1H-benzo[d]imidazole in 62% yield.

Example 68

5-Bromo-N-(cyclopropylmethyl)-2-nitroaniline

Cyclopropylmethylamine (10 mmol, 0.87 mL) was added drop-wise to a solution of 4-bromo-2-fluoro-1-nitrobenzene (9.1 mmol, 2 g) and diisopropylethylamine (10.9 mmol, 1.8 mL) in n-butanol (20 mL). The resulting solution was stirred at 80° C. for 18 hours. The mixture was concentrated under reduced pressure and the residue partitioned between water and dichloromethane. The organic extract was passed through a phase separator cartridge and concentrated under reduced pressure to afford the crude title compound as a brown solid (2.44 g, 99%) which was used without further purification.

Example 69

6-Bromo-1-(cyclopropylmethyl)-1H-benzo[d]imidazole

A mixture of 5-bromo-N-(cyclopropylmethyl)-2-nitroaniline (9.0 mmol, 2.44 g), iron powder (46.8 mmol, 2.61 g), ammonium chloride (81.0 mmol, 4.33 g) and water (19.4 mL) in ethanol (190 mL) was heated at 90° C. for 3 hours. The suspension was filtered hot through Celite® and the filtrate was concentrated under reduced pressure. The residue was re-suspended in trimethylorthoformate (115 mL)

and para-toluene sulfonic acid monohydrate (0.59 g) was added. The suspension was heated at 115° C. for 4 hours then cooled to room temperature and concentrated under reduced pressure. Purification by column chromatography (silica gel, gradient of 50-100% ethyl acetate in isohexane) gave the title compound as a light brown solid (1.18 g, 52%).

Example 70

7-((1-(Cyclopropylmethyl)-1H-benzo[d]imidazol-6yl)amino)-2,2-difluoro-4-methyl-2H-benzo[b][1,4]oxazin-3(4H)-one Using a similar procedure to that for Example 37, the title compound was prepared from 7-amino-2,2-difluoro-4-methyl-2H-pyrido[3,2-b][1,4]oxazin-3(4H)-one and 6-bromo-1-(cyclopropylmethyl)-1H-benzo[d]imidazole in 60% yield.

Example 71

7-((1-(Cyclopropylmethyl)-1H-benzo[d]imidazol-6yl)amino)-4-ethyl-2H-pyrido[3,2-b][1,4]oxazin-3(4H)-one Using a similar procedure to that for Example 37, the title compound was prepared from 7-amino-4-ethyl-2H-pyrido[3,2-b][1,4]oxazin-3(4H)-one and 6-bromo-1-(cyclopropylmethyl)-1H-benzo[d]imidazole in 18% yield.

Example 72

5-Bromo-4-chloro-N-(cyclopropylmethyl)-2-nitroaniline

Cyclopropylmethylamine (4.7 mmol, 0.38 mL,) was added drop-wise to a solution of 1-bromo-2-chloro-5-fluoro-1-nitrobenzene (3.9 mmol, 1 g,) and diisopropylethylamine (4.7 mmol, 0.74 mL) in n-butanol (10 mL). The resulting solution was stirred at 80° C. for 18 hours. The mixture was concentrated under reduced pressure and partitioned between water and dichloromethane. The organic extract was passed through a phase separator cartridge and concentrated under reduced pressure to afford the crude title compound as a brown solid (1.18 g, 98%) which was used without further purification.

Example 73

6-Bromo-5-chloro-1-(cyclopropylmethyl)-1H-benzo[d]imidazole

A mixture of 5-bromo-4-chloro-N-(cyclopropylmethyl)-2-nitroaniline (3.86 mmol, 1.18 g), iron powder (20.1 mmol, 1.12 g), ammonium chloride (34.8 mmol, 1.86 g) and water (8.3 mL) in ethanol (83 mL) was heated at 95° C. for 3 hours. The suspension was filtered hot through Celite® and the filtrate was concentrated under reduced pressure. The residue was re-suspended in trimethylorthoformate (49 mL) and para-toluene sulfonic acid monohydrate (0.25 g) was added. The suspension was heated at 115° C. for 4 hours then cooled to room temperature and concentrated under reduced pressure. Purification by column chromatography (silica gel, gradient of 30-100% ethyl acetate in isohexane) gave the title compound as a brown solid (0.72 g, 65%).

Example 74

7-((5-Chloro-1-(cyclopropylmethyl)-1H-benzo[d]imidazol-6yl)amino)-4-methyl-2H-benzo[b][1,4]oxazin-3(4H)-one Using a similar procedure to that for Example 37, the title compound was prepared from 7-amino-4-methyl-2H-benzo[b][1,4]oxazin-3(4H)-one and 6-bromo-5-chloro-1-(cyclopropylmethyl)-1H-benzo[d]imidazole in 74% yield.

Example 75

7-((5-Cyclopropyl-1-(cyclopropylmethyl)-1H-benzo[d]imidazol-6-yl)amino)-4-methyl-2H-benzo[b][1,4]oxazin-3(4H)-one

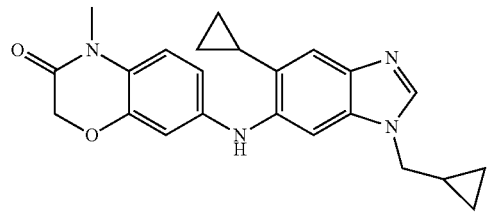 [SMILES: CN1C(=O)COc2cc(Nc3cc4c(cc3C3CC3)ncn4CC3CC3)ccc21]

7-((5-Chloro-1-(cyclopropylmethyl)-1H-benzo[d]imidazol-6yl)amino)-4-methyl-2Hbenzo[b][1,4]oxazin-3(4H)-one (0.13 mmol, 0.05 g), cyclopropyl boronic acid (0.19 mmol, 0.017 g), tribasic potassium phosphate monohydrate (0.39 mmol, 0.09 g) and $Cl_2Pd(P(cyhex)_3)_2$ (0.0085 mmol, 0.0062 g) were suspended in toluene (1.8 mL) and water (0.26 mL). Nitrogen was bubbled through the reaction mixture for 1 minute which was then heated at 130° C. for 18 hours. The mixture was diluted with dichloromethane and washed with water. The aqueous phase was extracted with dichloromethane. The combined organic extracts were passed through a phase separator cartridge and concentrated under reduced pressure. Purification by preparative HPLC gave the title compound as a white solid (0.029 g, 58%).

Example 76

7-((5-Chloro-1-(cyclopropylmethyl)-1H-benzo[d]imidazol-6-yl)amino)-4-methyl-2H-pyrido[3,2-b][1,4]oxazin-3(4H)-one Using a similar procedure to that for Example 37, the title compound was prepared from 7-amino-4-methyl-2H-pyrido[3,2-b][1,4]oxazin-3(4H)-one and 6-bromo-5-chloro-1-(cyclopropylmethyl)-1H-benzo[d]imidazole in 88% yield.

Example 77

7-((5-Cyclopropyl-1-(cyclopropylmethyl)-1H-benzo[d]imidazol-6-yl)amino)-4-methyl-2H-pyrido[3,2-b][1,4]oxazin-3(4H)-one Using a similar procedure to that for Example 75, the title compound was prepared from 7-((5-chloro-1-(cyclopropylmethyl)-1H-benzo[d]imidazol-6-yl)amino)-4-methyl-2H-pyrido[3,2-b][1,4]oxazin-3(4H)-one in 24% yield.

Example 78

1-Bromo-5-fluoro-2-methoxy-4-nitrobenzene

Methyl iodide (6.38 mmol, 0.39 mL) was added to 2-bromo-4-fluoro-5-nitrophenol (4.25 mmol, 1 g) and potassium carbonate (6.38 mmol, 0.88 g) in acetone (7 mL). The mixture was heated at reflux for 4 hours. The mixture was cooled, filtered and concentrated under reduced pressure. Purification of the crude product by column chromatography (silica gel, gradient of 0-50% ethyl acetate in isohexane) gave the title compound as a white solid (0.96 g, 91%).

Example 79

5-Bromo-N-(cyclopropylmethyl)-4-methoxy-2-nitroaniline

Cyclopropylmethylamine (4.24 mmol, 0.37 mL) was added drop-wise to a solution of 1-bromo-5-fluoro-2-methoxy-4-nitrobenzene (3.85 mmol, 0.96 g) and diisopropylethylamine (4.63 mmol, 0.76 mL) in n-butanol (8.5 mL). The resulting solution was stirred at 80° C. for 6.5 hours. The mixture was concentrated and partitioned between water and dichloromethane. The organic extract was passed through a phase separator cartridge and concentrated under reduced pressure to afford the crude title compound as an off-white solid (1.26 g, 100%) which was used without further purification.

Example 80

6-Bromo-1-(cyclopropylmethyl)-5-methoxy-1H-benzo[d]imidazole

A mixture of 5-bromo-N-(cyclopropylmethyl)-4-methoxy-2-nitroaniline (4 mmol, 1.2 g), iron powder (21 mmol, 1.16 g), ammonium chloride (53 mmol, 1.93 g) and water (8.6 mL) in ethanol (86 mL) was heated at 95° C. for 3 hours. The suspension was filtered hot through Celite® and the filtrate was concentrated under reduced pressure. The residue was re-suspended in trimethylorthoformate (50 mL) and para-toluene sulfonic acid monohydrate (0.27 g) was added. The suspension was heated at 115° C. for 3 hours, then cooled to room temperature and concentrated under reduced pressure. Purification of the crude product by column chromatography (silica gel, gradient of 30-100% ethyl acetate in isohexane) gave the title compound as an off-white solid (0.57 g, 51%).

Example 81

7-((1-(Cyclopropylmethyl)-5-methoxy-1H-benzo[d]imidazol-6-yl)amino)-4-methyl-2H-benzo[b][1,4]oxazin-3(4H)-one Using a similar procedure to that for Example 37, the title compound was prepared from 7-amino-4-methyl-2H-benzo[b][1,4]oxazin-3(4H)-one and 6-bromo-1-(cyclopropylmethyl)-5-methoxy-1H-benzo[d]imidazole in 74% yield.

Example 82

7-((1-(Cyclopropylmethyl)-5-hydroxy-1H-benzo[d]imidazol-6-yl)amino)-4-methyl-2H-benzo[b][1,4]oxazin-3(4H)-one

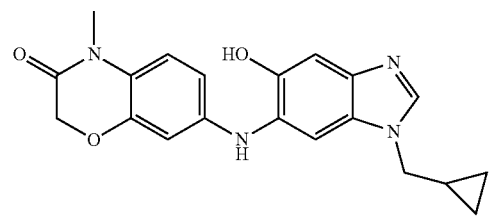 [SMILES: CN1C(=O)COc2cc(Nc3cc4c(cc3O)ncn4CC3CC3)ccc21]

Boron tribromide (1M in dichloromethane, 2.64 mL) was added to 7-((1-(cyclopropylmethyl)-5-methoxy-1H-benzo[d]imidazol-6-yl)amino)-4-methyl-2H-benzo[b][1,4]oxazin-3(4H)-one (0.132 mmol, 0.05 g) in dichloromethane (12 mL). The mixture was stirred at room temperature for 1.5 h before being quenched with methanol (1 mL) and water (1 mL). Methanol was evaporated under reduced pressure and dichloromethane was added to the resulting aqueous mixture. The resulting solid was collected by filtration, then suspended in dichloromethane and treated with saturated aqueous sodium bicarbonate solution. The aqueous phase was further extracted with dichloromethane. The organic extracts were passed through a phase separator cartridge and concentrated under reduced pressure to afford the title compound as a white solid (0.031 g, 65%).

Example 83

7-((1-(Cyclopropylmethyl)-5-methoxy-1H-benzo[d]imidazol-6-yl)amino)-2,2-difluoro-4-methyl-2H-benzo[b][1,4]oxazin-3(4H)-one Using a similar procedure to that for Example 37, the title compound was prepared from 7-amino-2,2-difluoro-4-methyl-2H-benzo[b][1,4]oxazin-3(4H)-one and 6-bromo-1-(cyclopropylmethyl)-5-methoxy-1H-benzo[d]imidazole in 12% yield.

Example 84

6-Bromo-5-fluoro-4-methyl-1H-benzo[d]imidazole

A mixture of 4-bromo-3-fluoro-2-methyl-6-nitroaniline (2 mmol, 0.5 g), iron powder (10 mmol, 0.59 g), ammonium chloride (18 mmol, 0.97 g) and water (4.3 mL) in ethanol (43 mL) was heated at 95° C. for 2 hours. The suspension was filtered hot through Celite® and the filtrate was concentrated under reduced pressure. The crude residue was re-suspended in trimethylorthoformate (25 mL) and para-toluene sulfonic acid monohydrate (0.13 g) was added. The suspension was heated at 115° C. for 1 hour 45 min, and then cooled to room temperature. The mixture was diluted with dichloromethane and washed with saturated aqueous sodium bicarbonate solution and brine. The organic extracts were passed through a phase separator cartridge and concentrated under reduced pressure to afford the title compound as a brown solid (0.31 g, 67%) which was used without further purification.

Example 85

6-Bromo-1-(cyclopropylmethyl)-5-fluoro-4-methyl-1H-benzo[d]imidazole (Bromomethyl)cyclopropane (2.07 mmol, 0.2 mL) was added drop-wise to mixture of 6-bromo-5-fluoro-4-methyl-1H-benzo[d]imidazole (1.38 mmol, 0.32 g) and potassium carbonate (2.07 mmol, 0.29 g) in DMF (4 mL). The mixture was stirred at 30° C. for 4 hours. The mixture was diluted with ethyl acetate and water and the organic extract was separated, washed with brine, dried (MgSO$_4$) and concentrated under reduced pressure. Purification of the crude product by column chromatography (silica gel, gradient of 30-100% ethyl acetate in isohexane) gave the title compound (containing ~20% of the isomeric 5-bromo-1-(cyclopropylmethyl)-6-fluoro-7-methyl-1H-benzo[d]imidazole) as an off-white solid (0.31 g, 80%).

Example 86

7-((1-(Cyclopropylmethyl)-5-fluoro-4-methyl-1H-benzo[d]imidazol-6-yl)amino)-4-methyl-2H-pyrido[3,2-b][1,4]oxazin-3(4H)-one

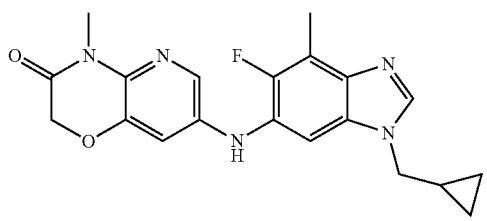 [SMILES: Cc1c(F)c(Nc2cnc3c(c2)OCC(=O)N3C)cc2c1ncn2CC1CC1]

Using a similar procedure to that for Example 37, the title compound was prepared from 7-amino-4-methyl-2H-pyrido[3,2-b][1,4]oxazin-3(4H)-one and 6-bromo-1-(cyclopropylmethyl)-5-fluoro-4-methyl-1H-benzo[d]imidazole in 58% yield.

$^1$H NMR (400 MHz, d6-DMSO) 8.19 (1H, s), 7.98 (1H, s), 7.82 (1H, d, J=2.3 Hz), 7.33 (1H, d, J=7.1 Hz), 7.01 (1H, d, J=2.3 Hz), 4.73 (2H, s), 4.07 (2H, d, J=7.1 Hz), 2.50-2.48 (3H, m), 1.28-1.20 (1H, m), 0.58-0.52 (2H, m), 0.43-0.38 (2H, m).

Example 87

7-((1-(Cyclopropylmethyl)-5-fluoro-4-methyl-1H-benzo[d]imidazol-6-yl)amino)-4-methyl-2H-pyrido[4,3-b][1,4]oxazin-3(4H)-one Using a similar procedure to that for Example 37, the title compound was prepared from 7-amino-4-methyl-2H-pyrido[4,3-b][1,4]oxazin-3(4H)-one hydrochloride and 6-bromo-1-(cyclopropylmethyl)-5-fluoro-4-methyl-1H-benzo[d]imidazole in 48% yield.

Example 88

N-(6-(1H-Imidazol-1-yl)pyridin-3-yl)-1-(cyclopropylmethyl)-5-fluoro-4-methyl-1H-benzo[d]imidazol-6-amine Using a similar procedure to that for Example 37, the title compound was prepared from 6-(1H-imidazol-1-yl)pyridin-3-amine and 6-bromo-1-(cyclopropylmethyl)-5-fluoro-4-methyl-1H-benzo[d]imidazole in 27% yield.

Example 89

6-Bromo-4-methyl-1H-benzo[d]imidazole

A mixture of 5-bromo-3-methylbenzene-1,2-diamine (2.5 mmol, 0.5 g), was suspended in trimethylorthoformate (34 mL) and para-toluene sulfonic acid monohydrate (0.17 g) was added. The suspension was heated at 115° C. for 1.5 hours, and then cooled to room temperature. The mixture was diluted with dichloromethane and washed with saturated sodium bicarbonate solution and brine. The organic extracts were combined, passed through a phase separator cartridge and concentrated under reduced pressure to afford the crude title compound as a brown solid (0.78 g, >100%) which was used without further purification.

Example 90

6-Bromo-1-(cyclopropylmethyl)-4-methyl-1H-benzo[d]imidazole (Bromomethyl)cyclopropane (3.75 mmol, 0.36 mL) was added drop-wise to mixture of 6-bromo-4-methyl-1H-benzo[d]imidazole (2.5 mmol) and potassium carbonate (3.75 mmol, 0.52 g,) in DMF (8 mL). The mixture was stirred at room temperature for 48 hours and 60° C. for 3 h. The mixture was diluted with ethyl acetate and water and the organic extract was washed with brine, dried (MgSO$_4$) and concentrated under reduced pressure. Purification of the crude product by column chromatography (silica gel, gradient of 30-100% ethyl acetate in isohexane) gave the title compound (containing ~25% of the isomeric 5-bromo-1-(cyclopropylmethyl)-7-methyl-1H-benzo[d]imidazole) as an off-white solid (0.29 g, 44%).

Example 91

7-((1-(Cyclopropylmethyl)-4-methyl-1H-benzo[d]imidazol-6-yl)amino)-4-methyl-2H-pyrido[4,3-b][1,4]oxazin-3(4H)-one Using a similar procedure to that for Example 37, the title compound was prepared from 7-amino-4-methyl-2H-pyrido[4,3-b][1,4]oxazin-3(4H)-one hydrochloride and 6-bromo-1-(cyclopropylmethyl)-4-methyl-1H-benzo[d]imidazole in 22% yield.

$^1$H NMR (400 MHz, d6-DMSO) 8.92 (1H, s), 8.08 (1H, s), 7.98 (2H, s), 7.02 (1H, s), 6.46 (1H, s), 4.75 (2H, s), 4.03 (2H, d, J=7.1 Hz), 3.32 (3H, s), 1.32-1.23 (1H, m), 0.61-0.55 (2H, m), 0.48-0.42 (2H, m).

Example 92

6-Bromo-1-(cyclopropylmethyl)-4,5-difluoro-1H-benzo[d]imidazole (Bromomethyl)cyclopropane (6.43 mmol, 0.62 mL) was added drop-wise to mixture of 6-bromo-4,5-difluorobenzimidazole (4.29 mmol, 1 g) and potassium carbonate (6.43 mmol, 0.88 g) in DMF (12 mL). The mixture was stirred at room temperature for 3.5 hours. The mixture was diluted with ethyl acetate and water and the organic extract was washed with brine, dried (MgSO$_4$) and concentrated under reduced pressure. Purification of the crude product by col-

Example 93

6-((1-(Cyclopropylmethyl)-4,5-difluoro-1H-benzo[d]imidazol-6-yl)amino)-4-methyl-2H-benzo[b][1,4]oxazin-3(4H)-one Using a similar procedure to that for Example 37, the title compound was prepared from 6-amino-4-methyl-2H-benzo[b][1,4]oxazin-3(4H)-one and 6-bromo-1-(cyclopropylmethyl)-4,5-difluoro-1H-benzo[d]imidazole in 30% yield.

Example 94

N-(1-(Cyclopropylmethyl)-4,5-difluoro-1H-benzo[d]imidazol-6-yl)-2-methylbenzo[d]oxazol-6-amine Using a similar procedure to that for Example 37, the title compound was prepared from 2-methylbenzo[d]oxazol-6-amine and 6-bromo-1-(cyclopropylmethyl)-4,5-difluoro-1H-benzo[d]imidazole in 6% yield.

$^1$H NMR (400 MHz, d6-DMSO) 8.28 (1H, s), 8.25 (1H, s), 7.51 (1H, d, J=8.6 Hz), 7.40-7.37 (1H, m), 7.26 (1H, d, J=2.0 Hz), 7.07 (1H, dd, J=1.9, 8.5 Hz), 4.08 (2H, d, J=7.1 Hz), 2.57 (3H, s), 1.30-1.22 (1H, m), 0.60-0.54 (2H, m), 0.41 (2H, q, J=5.0 Hz).

Example 95

1-(Cyclopropylmethyl)-4,5-difluoro-N-(3-fluoro-4-(1H-imidazol-1-yl)phenyl)-1H-benzo[d]imidazol-6-amine Using a similar procedure to that for Example 37, the title compound was prepared from 3-fluoro-4-(1H-imidazol-1-yl)aniline and 6-bromo-1-(cyclopropylmethyl)-4,5-difluoro-1H-benzo[d]imidazole in 37% yield.

Example 96

2-Chloro-4-fluoro-5-nitrobenzonitrile

2-Chloro-4-fluoro-benzonitrile (6.45 mmol, 1 g) was dissolved in concentrated sulphuric acid (1 mL) and cooled to 0° C. Concentrated fuming nitric acid (0.58 mL) was added drop-wise to the stirred solution at 0° C. The reaction was warmed to room temperature and stirred for 30 min before being poured into an ice/water mixture. The resulting solid was collected by filtration and dried in a vacuum oven to afford the title compound as a yellow solid (1.09 g, 84%).

Example 97

2-Chloro-4-((cyclopropylmethyl)amino)-5-nitrobenzonitrile

Cyclopropylmethylamine (5.9 mmol, 0.52 mL) was added drop-wise to a solution of 2-chloro-4-fluoro-5-nitrobenzonitrile (5.4 mmol, 1 g) and diisopropylethylamine (6.5 mmol, 1.07 mL) in ethanol (10 mL). The resulting solution was stirred at 80° C. for 2 hours. The mixture was concentrated under reduced pressure and partitioned between water and dichloromethane. The organic extract was passed through a phase separator cartridge and concentrated under reduced pressure to afford the crude title compound as a brown solid (1.34 g, 100%) which was used without further purification.

Example 98

6-Chloro-1-(cyclopropylmethyl)-1H-benzo[d]imidazole-5-carbonitrile

A mixture of 2-chloro-4-((cyclopropylmethyl)amino)-5-nitrobenzonitrile (4.3 mmol, 1.00 g), iron powder (22.3 mmol, 1.25 g), ammonium chloride (39 mmol, 2.07 g) and water (9.3 mL) in ethanol (93 mL) was heated at 95° C. for 6 hours. The suspension was filtered hot through Celite® and the filtrate was concentrated under reduced pressure. The residue was re-suspended in trimethylorthoformate (55 mL) and para-toluene sulfonic acid monohydrate (0.28 g) was added. The suspension was heated at 115° C. for 3 hours, then cooled to room temperature and concentrated under reduced pressure. The mixture was diluted with ethyl acetate and water and the organic extract was dried (MgSO$_4$) and concentrated under reduced pressure. Purification of the crude product by trituration with diethyl ether gave the title compound as a pale pink solid (0.84 g, 85%).

Example 99

1-(Cyclopropylmethyl)-6-((1-methyl-2-oxo-1,2,3,4-tetrahydroquinolin-6-yl)amino)-1H-benzo[d]imidazole-5-carbonitrile Using a similar procedure to that for Example 37, the title compound was prepared from 6-amino-1-methyl-3,4-dihydroquinolin-2(1H)-one and 6-chloro-1-(cyclopropylmethyl)-1H-benzo[d]imidazole-5-carbonitrile in 38% yield.

Example 100

2,3,6-Trichloro-5-nitropyridine 2,3,6-Trichloropyridine (62 mmol, 11.27 g) was dissolved in a mixture of fuming nitric acid (62 mL) and concentrated sulphuric acid (50 mL) and heated at 100° C. for 12 hours. The mixture was cooled, carefully poured into ice/water then extracted with dichloromethane. The organic extract was dried (MgSO$_4$) then concentrated under reduced pressure to give the title compound as pale green oil which solidified on standing (9.65 g, 68%).

Example 101

5,6-Dichloro-3-(cyclopropylmethyl)-3H-imidazo[4,5-b]pyridine

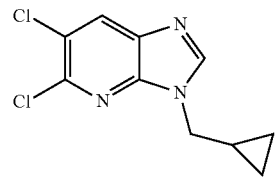 [SMILES: Clc1cc2ncn(CC3CC3)c2nc1Cl]

Cyclopropylmethylamine was (42.00 mmol, 7.50 g) was added drop-wise to a suspension of 2,3,6-trichloro-5-nitropyridine (42 mmol, 9.65 g) and potassium carbonate (54.00 mmol, 7.50 g) in acetonitrile (100 mL), cooled to −20° C. The mixture was then stirred at room temperature for 20 hours and filtered and concentrated under reduced pressure onto silica gel. Purification by column chromatography (silica gel, gradient of 5-10% ethyl acetate in isohexane) gave yellow oil. This was dissolved in ethanol (165 mL) and water (18 mL). Ammonium chloride (130 mmol, 6.95 g) then iron powder (76.16 mmol, 4.25 g) were added and the mixture was heated at 95° C. for 2 hours. The hot mixture was filtered and the filtrate was concentrated under reduced pressure. The residue was suspended in trimethylorthoformate (50 mL) and catalytic para-toluene sulfonic acid monohydrate was added. The mixture was heated at 110° C. for 3 hours then concentrated under reduced pressure onto silica gel. Purification by column chromatography (silica gel, gradient of 30-80% ethyl acetate in isohexane) gave the title compound as brown oil which solidified on standing (1.95 g, 19%).

Example 102

7-((6-Chloro-3-(cyclopropylmethyl)-3H-imidazo[4,5-b]pyridin-5-yl)amino)-4-methyl-2H-benzo[b][1,4]oxazin-3(4H)-one Using a similar procedure to that for Example 37, the title compound was prepared from 7-amino-4-methyl-2H-benzo[b][1,4]oxazin-3(4H)-one and 5,6-dichloro-3-(cyclopropylmethyl)-3H-imidazo[4,5-b]pyridine in 71% yield.

Example 103

7-((6-Chloro-3-(cyclopropylmethyl)-3H-imidazo[4,5-b]pyridin-5-yl)amino)-2,4-dimethyl-2H-benzo[b][1,4]oxazin-3(4H)-one Using a similar procedure to that for Example 37, the title compound was prepared from 7-amino-2,4-dimethyl-2H-benzo[b][1,4]oxazin-3(4H)-one and 5,6-dichloro-3-(cyclopropylmethyl)-3H-imidazo[4,5-b]pyridine in 56% yield.

Example 104

7-((3-(Cyclopropylmethyl)-6-vinyl-3H-imidazo[4,5-b]pyridin-5-yl)amino)-4-methyl-2H-benzo[b][1,4]oxazin-3(4H)-one

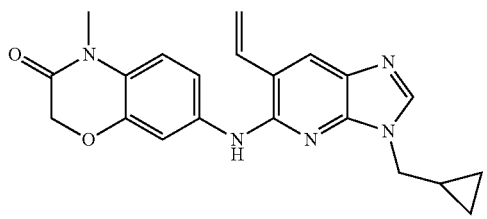 [SMILES: C=Cc1cc2ncn(CC3CC3)c2nc1Nc1ccc2c(c1)OCC(=O)N2C]

A solution of 7-((6-chloro-3-(cyclopropylmethyl)-3H-imidazo[4,5-b]pyridin-5-yl)amino)-4-methyl-2H-benzo[b][1,4]oxazin-3(4H)-one (0.26 mmol, 0.10 g), vinyl borolane (0.26 mmol, 0.04 g), palladiumtetrakistriphenylphosphine (5 mol %, 0.015 g) and aqueous sodium carbonate solution (2M, 6.50 mL) in toluene/ethanol (2:1, 6.5 mL) was heated at 150° C. in a microwave reactor for 9 hours. The mixture was charged a further two times with vinyl borolane (0.59 mmol, 0.10 mL) and palladiumtetrakistriphenylphosphine (0.005 g) with heating in a microwave reactor at 150° C. for 2×1 hour. The mixture was concentrated under reduced pressure and the product purified by preparative HPLC to give the title compound as a pale brown solid (23 mg, 24%).

Example 105

5-Bromo-3-(oxetan-3-ylmethyl)-3H-imidazo[4,5-b]pyridine

A solution of oxetan-3-ylmethyl methanesulfonate (3.25 mmol, 0.54 g), 5-bromo-3H-imidazo[4,5-b]pyridine (1.31 mmol, 0.26 g) and potassium carbonate (3.63 mmol, 0.50 g) in DMF (4 mL) was heated at 110° C. for 24 hours. The mixture was concentrated under reduced pressure then partitioned between water and dichloromethane. The organic extracts were dried (MgSO$_4$) and concentrated under reduced pressure. The residue was purified by column chromatography (silica gel, gradient of 1-5% methanol in dichloromethane) to give the title compound as a golden solid (0.27 g, 77%).

Example 106

4-Methyl-7-((3-(oxetan-3-ylmethyl)-3H-imidazo[4,5-b]pyridin-5-yl)amino)-2H-benzo[b][1,4]oxazin-3(4H)-one Using a similar procedure to that for Example 37, the title compound was prepared from 7-amino-2,4-dimethyl-2H-benzo[b][1,4]oxazin-3(4H)-one and 5-bromo-3-(oxetan-3-ylmethyl)-3H-imidazo[4,5-b]pyridine in 11% yield.

Example 107

5-Chloro-3-(cyclopropylmethyl)-3H-imidazo[4,5-b]pyridine

Using a similar procedure to that for Example 101 starting from 2,6-dichloro-3-nitropyridine, the title compound was prepared in 45% yield.

Example 108

6-((3-(Cyclopropylmethyl)-3H-imidazo[4,5-b]pyridin-5-yl)amino)-4-methyl-2H-benzo[b][1,4]oxazin-3(4H)-one Using a similar procedure to that for Example 37, the title compound was prepared from 6-amino-4-methyl-2H-benzo[b][1,4]oxazin-3(4H)-one and 5-chloro-3-(cyclopropylmethyl)-3H-imidazo[4,5-b]pyridine in 32% yield.

Example 109

5-((3-(Cyclopropylmethyl)-3H-imidazo[4,5-b]pyridin-5-yl)amino)-3-methylbenzo[d]oxazol-2(3H)-one Using a similar procedure to that for Example 37, the title compound was prepared from 5-amino-3-methylbenzo[d]oxazol-2(3H)-one and 5-chloro-3-(cyclopropylmethyl)-3H-imidazo[4,5-b]pyridine in 39% yield.

Example 110

3-(Cyclopropylmethyl)-N-(1-methyl-1H-benzo[d]
imidazol-6-yl)-3H-imidazo[4,5-b]pyridin-5-amine Using a similar procedure to that for Example 37, the title compound was prepared from 1-methyl-1H-benzo[d]imidazol-6-amine and 5-chloro-3-(cyclopropylmethyl)-3H-imidazo[4,5-b]pyridine in 45% yield.

Example 111

7-((3-(Cyclopropylmethyl)-3H-imidazo[4,5-b]pyridin-5-yl)amino)-1-methyl-1H-pyrido[2,3-b][1,4]
oxazin-2(3H)-one

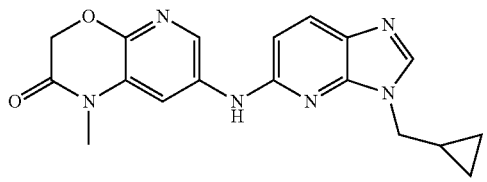 [SMILES: CN1C(=O)COc2ncc(Nc3ccc4ncn(CC5CC5)c4n3)cc21]

Using a similar procedure to that for Example 37, the title compound was prepared from 7-amino-1-methyl-1H-pyrido[2,3-b][1,4]oxazin-2(3H)-one and 5-chloro-3-(cyclopropylmethyl)-3H-imidazo[4,5-b]pyridine in 22% yield.

Example 112

6-Chloro-2-((cyclopropylmethyl)amino)-5-fluoronicotinamide

A mixture of 2,6-dichloro-5-fluoronicotinic acid (60.0 mmol, 12.60 g), cyclopropylmethylamine (69.24 mmol, 5.40 mL) and diisopropylethylamine (180 mmol, 31.4 mL) in acetonitrile (60 mL) was heated at reflux for 3 days. The mixture was concentrated under reduced pressure to give a pale purple gum. This was suspended in DMF (200 mL) and 1-hydroxybenzotriazole (72 mmol, 9.72 g), ammonium chloride (144 mmol, 7.68 g), EDC.HCl (105 mmol, 20.2 g) and triethylamine (139.5 mmol, 19 mL) were added. The mixture was stirred for 20 hours then concentrated under reduced pressure. The residue was partitioned between dichloromethane and saturated aqueous sodium bicarbonate solution. The aqueous phase was further extracted with dichloromethane. The combined organic extracts were dried (MgSO$_4$) and concentrated under reduced pressure to give brown oil. This was purified by column chromatography (silica gel, gradient of 10-50% ethyl acetate in isohexane) to give the title compound as pale brown oil (5.80 g, 40%).

Example 113 tert-Butyl (3-carbamoyl-6-chloro-5-fluoropyridin-2-yl)(cyclopropylmethyl)carbamate tert-Butyl dicarbonate (52.41 mmol, 11.43 g) and 4-dimethylaminopyridine (2.38 mmol, 0.29 g) were added to a solution of 6-chloro-2-((cyclopropylmethyl)amino)-5-fluoronicotinamide (23.8 mmol, 5.80 g) in dichloromethane (67 mL). The mixture was stirred for 3 hours then concentrated under reduced pressure. The residue was purified by column chromatography (silica gel, gradient of 5-25% ethyl acetate in isohexane) to give the title compound as colourless oil (4.29 g, 52%).

Example 114 tert-Butyl (3-amino-6-chloro-5-fluoropyridin-2-yl)
(cyclopropylmethyl)carbamate

A mixture of tert-butyl (3-carbamoyl-6-chloro-5-fluoropyridin-2-yl)(cyclopropylmethyl)carbamate (10.90 mmol, 3.76 g), diphenylphosphoryl azide (32.71 mmol, 7.05 mL) and triethylamine (109.0 mmol, 15.1 mL) in toluene (150 mL) was heated at 100° C. for 2 hours. The mixture was cooled then diluted with ethyl acetate and water. The organic extracts were dried (MgSO$_4$) and concentrated under reduced pressure to give light brown oil which was purified by column chromatography (silica gel, gradient of 5-25% ethyl acetate in isohexane) to give the title compound as brown oil (0.51 g, 15%).

Example 115

5-Chloro-3-(cyclopropylmethyl)-6-fluoro-3H-imidazo[4,5-b]pyridine

A solution of tert-butyl (3-amino-6-chloro-5-fluoropyridin-2-yl)(cyclopropylmethyl)carbamate (2.15 mmol, 0.68 g) and catalytic para-toluene sulfonic acid in trimethylorthoformate 10 mL was heated at reflux for 20 hours. The mixture was concentrated under reduced pressure onto silica gel then purified by column chromatography (silica gel, gradient of ethyl acetate in isohexane) to give the title compound as brown oil (0.052 g, 11%).

Example 116

7-((3-(Cyclopropylmethyl)-6-fluoro-3H-imidazo[4,5-b]pyridin-5-yl)amino)-4-methyl-2H-benzo[b][1,4]
oxazin-3(4H)-one Using a similar procedure to that for Example 37, the title compound was prepared from 7-amino-4-methyl-2H-benzo[b][1,4]oxazin-3(4H)-one and 5-chloro-3-(cyclopropylmethyl)-6-fluoro-3H-imidazo[4,5-b]pyridine in 16% yield.

Example 117

6-Chloro-1-(cyclopropylmethyl)-4-methyl-1H-imidazo[4,5-c]pyridine

Using a similar procedures to that for Example 101, the title compound was prepared from 4,6-dichloro-2-methyl-3-nitropyridine in 70% yield.

Example 118

7-((1-(Cyclopropylmethyl)-4-methyl-1H-imidazo[4,5-c]pyridin-6-yl)amino)-4-methyl-2H-benzo[b][1,4]
oxazin-3(4H)-one Using a similar procedure to that for Example 37, the title compound was prepared from 7-amino-4-methyl-2H-benzo[b][1,4]oxazin-3(4H)-one and 6-chloro-1-(cyclopropylmethyl)-4-methyl-1H-imidazo[4,5-c]pyridine in 53% yield.

Example 119

7-((1-Butyl-4-methyl-1H-imidazo[4,5-c]pyridin-6-yl)amino)-4-methyl-2H-benzo[b][1,4]oxazin-3(4H)-one Using a similar procedure to that for Example 37, the title compound was isolated as a by-product from the reaction of 7-amino-4-methyl-2H-benzo[b][1,4]oxazin-3(4H)-one and 6-chloro-1-(cyclopropylmethyl)-4-methyl-1H-imidazo[4,5-c]pyridine in 14% yield.

Example 120

7-((1-(Cyclopropylmethyl)-4-methyl-1H-imidazo[4,5-c]pyridin-6-yl)amino)-4-methyl-2H-pyrido[3,2-b][1,4]oxazin-3(4H)-one Using a similar procedure to that for Example 37, the title compound was prepared from 7-amino-4-methyl-2H-pyrido[3,2-b][1,4]oxazin-3(4H)-one and 6-chloro-1-(cyclopropylmethyl)-4-methyl-1H-imidazo[4,5-c]pyridine in 49% yield.

Example 121

6-Chloro-7-((1-(cyclopropylmethyl)-4-methyl-1H-imidazo[4,5-c]pyridin-6-yl)amino)-4-methyl-2H-benzo[b][1,4]oxazin-3(4H)-one Using a similar procedure to that for Example 37, the title compound was prepared from 6-chloro-7-amino-4-methyl-2H-benzo[b][1,4]oxazin-3(4H)-one and 6-chloro-1-(cyclopropylmethyl)-4-methyl-1H-imidazo[4,5-c]pyridine in 9% yield.

Example 122

7-((1-(Cyclopropylmethyl)-4-methyl-1H-imidazo[4,5-c]pyridin-6-yl)amino)-4-(2-hydroxy-2-methylpropyl)-2H-benzo[b][1,4]oxazin-3(4H)-one Using a similar procedure to that for Example 37, the title compound was prepared from 7-amino-4-(2-hydroxy-2-methylpropyl)-2H-benzo[b][1,4]oxazin-3(4H)-one and 6-chloro-1-(cyclopropylmethyl)-4-methyl-1H-imidazo[4,5-c]pyridine in 60% yield.

Example 123

7-((1-(Cyclopropylmethyl)-4-methyl-1H-imidazo[4,5-c]pyridin-6-yl)amino)-4-(2-methoxyethyl)-2H-benzo[b][1,4]oxazin-3(4H)-one Using a similar procedure to that for Example 37, the title compound was prepared from 7-amino-4-(2-methoxyethyl)-2H-benzo[b][1,4]oxazin-3(4H)-one and 6-chloro-1-(cyclopropylmethyl)-4-methyl-1H-imidazo[4,5-c]pyridine in 40% yield.

Example 124

6-((1-(Cyclopropylmethyl)-4-methyl-1H-imidazo[4,5-c]pyridin-6-yl)amino)-1-methyl-1H-pyrido[2,3-b][1,4]oxazin-2(3H)-one Using a similar procedure to that for Example 37, the title compound was prepared from 6-amino-1-methyl-1H-pyrido[2,3-b][1,4]oxazin-2(3H)-one and 6-chloro-1-(cyclopropylmethyl)-4-methyl-1H-imidazo[4,5-c]pyridine in 48% yield.

Example 125

N-(1-(Cyclopropylmethyl)-4-methyl-1H-imidazo[4,5-c]pyridin-6-yl)-2-methylbenzo[d]oxazol-6-amine Using a similar procedure to that for Example 37, the title compound was prepared from 2-methylbenzo[d]oxazol-6-amine and 2-methylbenzo[d]oxazol-6-amine and 6-chloro-1-(cyclopropylmethyl)-4-methyl-1H-imidazo[4,5-c]pyridine in 21% yield.

Example 126

4-Cyclopropyl-7-((1-(cyclopropylmethyl)-4-methyl-1H-imidazo[4,5-c]pyridin-6-yl)amino)-2H-benzo[b][1,4]oxazin-3(4H)-one Using a similar procedure to that for Example 37, the title compound was prepared from 7-amino-4-cyclopropyl-2H-benzo[b][1,4]oxazin-3(4H)-one and 6-chloro-1-(cyclopropylmethyl)-4-methyl-1H-imidazo[4,5-c]pyridine in 20% yield.

Example 127

7-((1-(Cyclopropylmethyl)-4-methyl-1H-imidazo[4,5-c]pyridin-6-yl)amino)-4-ethyl-2H-pyrido[3,2-b][1,4]oxazin-3(4H)-one Using a similar procedure to that for Example 37, the title compound was prepared from 7-amino-4-ethyl-2H-pyrido[3,2-b][1,4]oxazin-3(4H)-one and 6-chloro-1-(cyclopropylmethyl)-4-methyl-1H-imidazo[4,5-c]pyridine in 38% yield.

Example 128

7-((1-(Cyclopropylmethyl)-4-methyl-1H-imidazo[4,5-c]pyridin-6-yl)amino)-4-(2,2-difluoroethyl)-2H-benzo[b][1,4]oxazin-3(4H)-one Using a similar procedure to that for Example 37, the title compound was prepared from 7-amino-4-(2,2-difluoroethyl)-2H-benzo[b][1,4]oxazin-3(4H)-one and 6-chloro-1-(cyclopropylmethyl)-4-methyl-1H-imidazo[4,5-c]pyridine in 65% yield.

Example 129

7-((1-(Cyclopropylmethyl)-4-methyl-1H-imidazo[4,5-c]pyridin-6-yl)amino)-4-(2-fluoroethyl)-2H-benzo[b][1,4]oxazin-3(4H)-one Using a similar procedure to that for Example 37, the title compound was prepared from 7-amino-4-(2-fluoroethyl)-2H-benzo[b][1,4]oxazin-3(4H)-one and 6-chloro-1-(2-cyclopropylethyl)-4-methyl-1H-imidazo[4,5-c]pyridine in 26% yield.

Example 130

5-Chloro-7-((1-(cyclopropylmethyl)-4-methyl-1H-imidazo[4,5-c]pyridin-6-yl)amino)-4-methyl-2H-benzo[b][1,4]oxazin-3(4H)-one Using a similar procedure to that for Example 37, the title compound was prepared from 7-amino-4-methyl-5-chloro- 2H-benzo[b][1,4]oxazin-3(4H)-one and 6-chloro-1-(2-cyclopropylethyl)-4-methyl-1H-imidazo[4,5-c]pyridine in 10% yield.

¹H NMR (400 MHz, d6-DMSO) 9.08 (1H, s), 8.18 (1H, s), 7.52-7.47 (2H, m), 6.83 (1H, s), 4.59 (2H, s), 4.05 (2H, d, J=7.1 Hz), 3.41 (3H, s), 2.67 (3H, s), 1.29-1.21 (1H, m), 0.61-0.55 (2H, m), 0.46-0.41 (2H, m).

Example 131

6-Chloro-1-(cyclopropylmethyl)-4-methyl-1H-imidazo[4,5-c]pyrimidine

Using a similar procedures to that for Example 101, the title compound was prepared from 2,4-dichloro-6-methyl-5-nitropyrimidine in 70% yield.

Example 132

7-((9-(Cyclopropylmethyl)-6-methyl-9H-purin-2-yl)amino)-4-methyl-2H-benzo[b][1,4]oxazin-3(4H)-one Using a similar procedure to that for Example 37, the title compound was prepared from 7-amino-4-methyl-2H-benzo[b][1,4]oxazin-3(4H)-one and 6-Chloro-1-(cyclopropylmethyl)-4-methyl-1H-imidazo[4,5-c]pyrimidine in 52% yield.

Example 133

6-Chloro-7-((9-(cyclopropylmethyl)-6-methyl-9H-purin-2-yl)amino)-4-(2,2-difluoroethyl)-2H-benzo[b][1,4]oxazin-3(4H)-one Using a similar procedure to that for Example 37, the title compound was prepared from 7-amino-6-chloro-4-(2,2-difluoroethyl)-2H-benzo[b][1,4]oxazin-3(4H)-one and 6-chloro-1-(cyclopropylmethyl)-4-methyl-1H-imidazo[4,5-c]pyrimidine in 24% yield.

Example 134

6-Chloro-7-((9-(cyclopropylmethyl)-6-methyl-9H-purin-2-yl)amino)-4-methyl-2H-benzo[b][1,4]oxazin-3(4H)-one Using a similar procedure to that for Example 37, the title compound was prepared from 7-amino-6-chloro-4-methyl-2H-benzo[b][1,4]oxazin-3(4H)-one and 6-Chloro-1-(cyclopropylmethyl)-4-methyl-1H-imidazo[4,5-c]pyrimidine in 47% yield.

Example 135

7-((9-(Cyclopropylmethyl)-6-methyl-9H-purin-2-yl)amino)-4-ethyl-2H-benzo[b][1,4]oxazin-3(4H)-one Using a similar procedure to that for Example 37, the title compound was prepared from 7-amino-4-ethyl-2H-benzo[b][1,4]oxazin-3(4H)-one and 6-Chloro-1-(cyclopropylmethyl)-4-methyl-1H-imidazo[4,5-c]pyrimidine in 55% yield.

¹H NMR (400 MHz, CDCl₃) 7.89 (1H, s), 7.61 (1H, d, J=2.3 Hz), 7.25-7.22 (1H, m), 7.11 (1H, s), 6.96 (1H, d, J=8.8 Hz), 4.61 (2H, s), 4.04-3.98 (4H, m), 2.74 (3H, s), 1.33-1.27 (4H, m), 0.74-0.68 (2H, m), 0.51-0.47 (2H, m).

Example 136

7-((9-(Cyclopropylmethyl)-6-methyl-9H-purin-2-yl)amino)-2,2-difluoro-4-methyl-2H-benzo[b][1,4]oxazin-3(4H)-one Using a similar procedure to that for Example 37, the title compound was prepared from 7-amino-2,2-difluoro-4-methyl-2H-benzo[b][1,4]oxazin-3(4H)-one and 6-chloro-1-(cyclopropylmethyl)-4-methyl-1H-imidazo[4,5-c]pyrimidine in 30% yield.

Example 137

7-((9-(Cyclopropylmethyl)-6-methyl-9H-purin-2-yl)amino)-4-(oxetan-3-ylmethyl)-2H-benzo[b][1,4]oxazin-3(4H)-one Using a similar procedure to that for Example 37, the title compound was prepared from 7-amino-4-(oxetan-3-ylmethyl)-2H-benzo[b][1,4]oxazin-3(4H)-one and 6-chloro-1-(cyclopropylmethyl)-4-methyl-1H-imidazo[4,5-c]pyrimidine in 63% yield.

Example 138

7-((9-(2-cyclopropylethyl)-6-methyl-9H-purin-2-yl)amino)-4-(2-fluoroethyl)-2H-benzo[b][1,4]oxazin-3(4H)-one Using a similar procedure to that for Example 37, the title compound was prepared from 7-amino-4-(2-fluoroethyl)-2H-benzo[b][1,4]oxazin-3(4H)-one and 6-chloro-1-(cyclopropylmethyl)-4-methyl-1H-imidazo[4,5-c]pyrimidine in 58% yield.

Example 139

5-Bromo-N-(cyclopropylmethyl)-2-nitro-4-(trifluoromethoxy)aniline

Sodium hydride (60% w/w, 3.75 mmol, 0.15 g) was added portion-wise to a solution of 5-bromo-2-nitro-4-(trifluoromethoxy)aniline (3.42 mmol, 1.03 g) and bromomethylcyclopropane (17.07 mmol, 1.66 mL) in THF (12 mL). The mixture was heated at reflux for 4 hours then concentrated under reduced pressure to give the crude title compound (3.51 g) which was used without further purification.

Example 140

6-Bromo-1-(cyclopropylmethyl)-5-(trifluoromethoxy)-1H-benzo[d]imidazole

Using a similar procedures to that for Example 98, the title compound was prepared from 5-bromo-N-(cyclopropylmethyl)-2-nitro-4-(trifluoromethoxy)aniline in 15% yield.

Example 141

6-((1-(Cyclopropylmethyl)-5-(trifluoromethoxy)-1H-benzo[d]imidazol-6-yl)amino)-1-methyl-1H-pyrido[2,3-b][1,4]oxazin-2(3H)-one Using a similar procedure to that for Example 37, the title compound was prepared from 6-amino-1-methyl-1H-pyrido

Example 142

7-((1-(Cyclopropylmethyl)-5-(trifluoromethoxy)-1H-benzo[d]imidazol-6-yl)amino)-2,2-difluoro-4-methyl-2H-benzo[b][1,4]oxazin-3(4H)-one Using a similar procedure to that for Example 37, the title compound was prepared from 7-amino-2,2-difluoro-4-methyl-2H-benzo[b][1,4]oxazin-3(4H)-one and 6-bromo-1-(cyclopropylmethyl)-5-(trifluoromethoxy)-1H-benzo[d]imidazole in 7% yield.

Example 143

7-((1-(Cyclopropylmethyl)-5-(trifluoromethoxy)-1H-benzo[d]imidazol-6-yl)amino)-4-methyl-2H-pyrido[3,2-b][1,4]oxazin-3(4H)-one Using a similar procedure to that for Example 37, the title compound was prepared from 7-amino-4-methyl-2H-pyrido[3,2-b][1,4]oxazin-3(4H)-one and 6-bromo-1-(cyclopropylmethyl)-5-(trifluoromethoxy)-1H-benzo[d]imidazole in 39% yield.

Example 144

6-Bromo-1-(cyclopropylmethyl)-7-fluoro-1H-benzo[d]imidazole

Using similar procedures to those for Example 56 and Example 57, the title compound was prepared from 2,3-difluoro-4-bromo-nitrobenzene in 78% yield.

Example 145

7-((1-(Cyclopropylmethyl)-7-fluoro-1H-benzo[d]imidazol-6-yl)amino)-4-ethyl-2H-pyrido[3,2-b][1,4]oxazin-3(4H)-one Using a similar procedure to that for Example 37, the title compound was prepared from 7-amino-4-ethyl-2H-pyrido[3,2-b][1,4]oxazin-3(4H)-one and 6-bromo-1-(cyclopropylmethyl)-7-fluoro-1H-benzo[d]imidazole in 41% yield.

Example 146

6-Chloro-1-(2-cyclopropylethyl)-4-methyl-1H-imidazo[4,5-c]pyridine

Using a similar procedure to that for Example 101, the title compound was prepared from 4,6-dichloro-2-methyl-3-nitropyridine and 1-(cyclopropylethyl)amine in 33% yield.

Example 147

7-((1-(2-Cyclopropylethyl)-4-methyl-1H-imidazo[4,5-c]pyridin-6-yl)amino)-4-methyl-2H-pyrido[3,2-b][1,4]oxazin-3(4H)-one Using a similar procedure to that for Example 37, the title compound was prepared from 7-amino-4-methyl-2H-pyrido[3,2-b][1,4]oxazin-3(4H)-one and 6-chloro-1-(2-cyclopropylethyl)-4-methyl-1H-imidazo[4,5-c]pyridine in 8% yield.

Example 148

7-((1-(2-cyclopropylethyl)-4-methyl-1H-imidazo[4,5-c]pyridin-6-yl)amino)-4-methyl-2H-pyrido[4,3-b][1,4]oxazin-3(4H)-one Using a similar procedure to that for Example 37, the title compound was prepared from 7-amino-4-methyl-2H-pyrido[4,3-b][1,4]oxazin-3(4H)-one hydrochloride and 6-chloro-1-(2-cyclopropylethyl)-4-methyl-1H-imidazo[4,5-c]pyridine in 41% yield.

Example 149

6-Chloro-N2-(cyclopropylmethyl)-4-(trifluoromethyl)pyridine-2,3-diamine

A solution of 2,6-dichloro-4-trifluoromethyl-5-aminopyridine (21.70 mmol, 5.00 g) and cyclopropylmethylamine (86.80 mmol, 7.52 mL) in NMP (25 mL) was heated at 150° C. overnight. The mixture was concentrated under reduced pressure and the crude product used without further purification.

Example 150

5-Chloro-3-(cyclopropylmethyl)-7-(trifluoromethyl)-3H-imidazo[4,5-b]pyridine

A solution of 6-chloro-N2-(cyclopropylmethyl)-4-(trifluoromethyl)pyridine-2,3-diamine and catalytic para-toluene sulfonic acid in trimethylorthoformate (50 mL) was heated at 90° C. for 4 hours then the mixture was cooled and concentrated under reduced pressure. The residue was purified by column chromatography (silica gel, gradient of 0-10% ethyl acetate in dichloromethane) to give the title compound as yellow oil which solidified on standing (5.01 g, 84%).

Example 151

6-((3-(Cyclopropylmethyl)-7-(trifluoromethyl)-3H-imidazo[4,5-b]pyridin-5-yl)amino)-1-methyl-1H-pyrido[2,3-b][1,4]oxazin-2(3H)-one Using a similar procedure to that for Example 37, the title compound was prepared from 6-amino-1-methyl-1H-pyrido[2,3-b][1,4]oxazin-2(3H)-one and 5-chloro-3-(cyclopropylmethyl)-7-(trifluoromethyl)-3H-imidazo[4,5-b]pyridine in 53% yield.

Example 152

2,6-Dichloro-4-methyl-3-nitropyridine

Fuming nitric acid (20 mL) was added drop-wise to an ice-cooled solution of 2,6-dichloro-4-methylpyridine (18.5 mmol, 3.0 g) in concentrated sulfuric acid (20 mL). The resulting solution was heated at 90° C. for 18 hours. The solution was cooled to room temperature and poured into a mixture of ice and water. After allowing to warm to room temperature, the suspension was filtered and the filter cake was washed with water. After drying in air, the title compound was obtained as a pale yellow solid (1.32 g, 36%; 3:1 mixture with 3,5-dinitro-2,6-dichloro-4-methylpyridine).

Example 153

6-Chloro-N-(cyclopropylmethyl)-4-methyl-3-nitropyridin-2-amine

Cyclopropylmethylamine (8.4 mmol, 0.72 mL,) was added drop-wise to a solution of 3-nitro-2,6-dichloropyridine (~4.8 mmol, 1.32 g at ~75% purity) in THF (10 mL). The resulting solution was stirred at room temperature for 18 hours. Additional cyclopropylmethylamine (2.7 mmol, 0.23 mL) was added and the reaction mixture was stirred for 18 hours. The yellow suspension was diluted with ethyl acetate and the solution was washed with saturated sodium hydrogen carbonate solution, dried (MgSO$_4$) and evaporated to afford the crude title compound as yellow oil (1.35 g) which was used without further purification.

Example 154

5-Chloro-3-(cyclopropylmethyl)-7-methyl-3H-imidazo[4,5-b]pyridine

A mixture of 6-chloro-N-(cyclopropylmethyl)-4-methyl-3-nitro-pyridin-2-amine (~4.8 mmol, 1.35 g), iron powder (29.6 mmol, 1.65 g), ammonium chloride (58.9 mmol, 3.15 g) and water (7 mL) in ethanol (70 mL) was heated at 90° C. for 4 hours. The suspension was filtered hot through Celite® and the filtrate was concentrated under reduced pressure. The crude product was re-suspended in ethyl acetate and the suspension was washed with saturated sodium hydrogen carbonate solution. The organic phase was dried (MgSO$_4$) and evaporated. The crude reduction product was re-suspended in trimethylorthoformate (40 mL) and para-toluene sulfonic acid monohydrate (0.30 g) was added. The suspension was heated at 100° C. for 18 hours, then cooled to room temperature and diluted with ethyl acetate. The solution was washed with saturated sodium hydrogen carbonate solution and saturated ammonium chloride solution, then dried (MgSO$_4$) and evaporated to give dark brown oil, which was purified by column chromatography (silica gel, gradient of ethyl acetate in isohexane) to give the title compound as a yellow solid (0.46 g, ~46% from 3-nitro-2,6-dichloro-4-methylpyridine).

Example 155

6-Chloro-7-((3-(cyclopropylmethyl)-7-methyl-3H-imidazo[4,5-b]pyridin-5-yl)amino)-2H-benzo[b][1,4]oxazin-3(4H)-one Using a similar procedure to that for Example 37, the title compound was prepared from 7-amino-6-chloro-2H-benzo[b][1,4]oxazin-3(4H)-one and 5-chloro-3-(cyclopropylmethyl)-7-methyl-3H-imidazo[4,5-b]pyridine in 21% yield.

Example 156

6-Chloro-7-((3-(cyclopropylmethyl)-7-methyl-3H-imidazo[4,5-b]pyridin-5-yl)amino)-4-(2,2-difluoroethyl)-2H-benzo[b][1,4]oxazin-3(4H)-one Using a similar procedure to that for Example 37, the title compound was prepared from 7-amino-6-chloro-4-(2,2-difluoroethyl)-2H-benzo[b][1,4]oxazin-3(4H)-one and 5-chloro-3-(cyclopropylmethyl)-7-methyl-3H-imidazo[4,5-b]pyridine in 54% yield.

Example 157

N-(5-(1H-Imidazol-1-yl)pyridin-2-yl)-3-(cyclopropylmethyl)-7-methyl-3H-imidazo[4,5-b]pyridin-5-amine Using a similar procedure to that for Example 37, the title compound was prepared from 5-(1H-imidazol-1-yl)pyridin-2-amine and 5-chloro-3-(cyclopropylmethyl)-7-methyl-3H-imidazo[4,5-b]pyridine in 83% yield.

Example 158

N-(6-(1H-Imidazol-1-yl)pyridin-3-yl)-3-(cyclopropylmethyl)-7-methyl-3H-imidazo[4,5-b]pyridin-5-amine

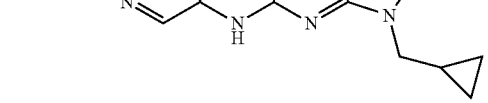

Using a similar procedure to that for Example 37, the title compound was prepared from 6-(1H-imidazol-1-yl)pyridin-3-amine and 5-chloro-3-(cyclopropylmethyl)-7-methyl-3H-imidazo[4,5-b]pyridine in 42% yield.

Example 159

6-((3-(Cyclopropylmethyl)-7-methyl-3H-imidazo[4,5-b]pyridin-5-yl)amino)-1-methyl-1H-pyrido[2,3-b][1,4]oxazin-2(3H)-one

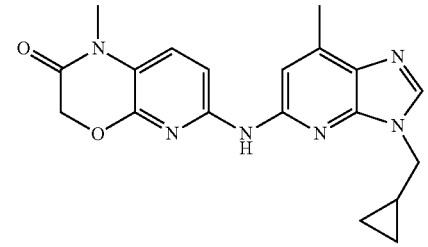 [SMILES: Cc1cc(Nc2ccc3c(n2)OCC(=O)N3C)nc2c1ncn2CC1CC1]

Using a similar procedure to that for Example 37, the title compound was prepared from 6-amino-1-methyl-1H-pyrido[2,3-b][1,4]oxazin-2(3H)-one and 5-chloro-3-(cyclopropylmethyl)-7-methyl-3H-imidazo[4,5-b]pyridine in 96% yield.

Example 160

6-Chloro-7-((3-(cyclopropylmethyl)-7-methyl-3H-imidazo[4,5-b]pyridin-5-yl)amino)-4-methyl-2H-benzo[b][1,4]oxazin-3(4H)-one

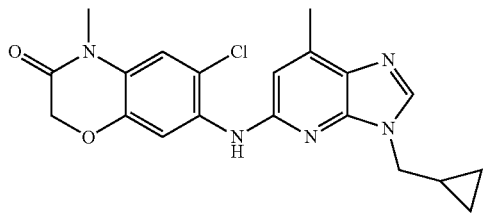 [SMILES: Cc1cc(Nc2cc3c(cc2Cl)N(C)C(=O)CO3)nc2c1ncn2CC1CC1]

Using a similar procedure to that for Example 37, the title compound was prepared from 7-amino-6-chloro-4-methyl-2H-benzo[b][1,4]oxazin-3(4H)-one and 5-chloro-3-(cyclopropylmethyl)-7-methyl-3H-imidazo[4,5-b]pyridine in 44% yield.

Example 161

6-((3-(Cyclopropylmethyl)-7-methyl-3H-imidazo[4,5-b]pyridin-5-yl)amino)-3-ethylquinazolin-4(3H)-one Using a similar procedure to that for Example 37, the title compound was prepared from of 6-amino-3-ethylquinazolin-4(3H)-one and 5-chloro-3-(cyclopropylmethyl)-7-methyl-3H-imidazo[4,5-b]pyridine in 52% yield.

Example 162

6-Chloro-1-((tetrahydrofuran-2-yl)methyl)-1H-imidazo[4,5-c]pyridine

A mixture of 6-chloro-3H-imidazo[4,5-c]pyridine (2.15 mmol, 0.33 g), tetrahydrofurfuryl bromide (2.74 mmol, 0.31 mL) and potassium carbonate (4.27 mmol, 0.59 g) in DMF (3 mL) was heated at 75° C. with stirring for 2 hours. The mixture was cooled to room temperature and diluted with ethyl acetate. The suspension was washed with water, dried ($MgSO_4$) and concentrated under reduced pressure to afford the crude product, which was purified by column chromatography (silica gel, ethyl acetate) to give the title compound as yellow oil (0.26 g, isomer mixture, 52%).

Example 163

4-Methyl-7-((1-((tetrahydrofuran-2-yl)methyl)-1H-imidazo[4,5-c]pyridin-6-yl)amino)-2H-benzo[b][1,4]oxazin-3(4H)-one Using a similar procedure to that for Example 37, the title compound was prepared from 7-amino-4-ethyl-2H-benzo[b][1,4]oxazin-3(4H)-one and 6-chloro-1-((tetrahydrofuran-2-yl)methyl)-1H-imidazo[4,5-c]pyridine in 21% yield.

Example 164

6-Chloro-1-(2-fluoro-2-methylpropyl)-1H-imidazo[4,5-c]pyridine

Using a similar procedure to that for Example 162, the title compound was prepared from 6-chloro-3H-imidazo[4,5-c]pyridine and 1-bromo-2-fluoro-2-methylpropane in 25% yield as an isomer mixture.

Example 165

7-((1-(2-Fluoro-2-methylpropyl)-1H-imidazo[4,5-c]pyridin-6-yl)amino)-4-methyl-2H-benzo[b][1,4]oxazin-3(4H)-one Using a similar procedure to that for Example 37, the title compound was prepared from 7-amino-4-methyl-2H-benzo[b][1,4]oxazin-3(4H)-one and 6-chloro-1-(2-fluoro-2-methylpropyl)-1H-imidazo[4,5-c]pyridine in 20% yield.

Example 166

5,6-Dichloro-3-(cyclopropylmethyl)-7-methyl-3H-imidazo[4,5-b]pyridine

A solution of n-butyllithium in hexanes (2.5M, 30 mmol, 12 mL) was added drop-wise to a solution of diisopropylamine (30 mmol, 4.3 mL) in dry THF (100 mL) at −78° C. After 1 hour, a solution of 2,3,6-trichloropyridine (27.4 mmol, 5 g) in dry THF (25 mL) was added over 15 minutes. After a further 1 hour, a solution of methyl iodide (30.4 mmol, 1.9 mL) in dry THF (10 mL) was added drop-wise over 5 minutes. The orange-brown solution was stirred at −78° C. for 15 minutes, then allowed to warm to room temperature and stirred at room temperature for 18 hours. The reaction was carefully quenched by the addition of saturated aqueous ammonium chloride solution and the mixture was extracted with ethyl acetate. The organic extract was washed with brine, dried ($MgSO_4$) and concentrated under reduced pressure. Partial purification of the crude product was achieved by column chromatography (silica gel, gradient of ethyl acetate in isohexane) to give the intermediate 2,3,6-trichloro-4-methylpyridine as an oily colourless solid (2.4 g).

A solution of the partially purified 2,3,6-trichloro-4-methylpyridine (2.4 g) in ice-cooled concentrated sulphuric acid (10 mL) was treated drop-wise with fuming nitric acid (10 mL). The mixture was stirred for 1 hour at room temperature then at 95° C. for 18 hours. After cooling to room temperature, the mixture was carefully poured on to ice. After allowing the ice to melt, the aqueous mixture was extracted with ethyl acetate and the organic extract washed with brine and dried ($MgSO_4$). The solution was concentrated and the crude product was partially purified by column chromatography (silica gel, gradient of ethyl acetate in isohexane) to give the intermediate 2,3,6-trichloro-4-methyl-5-nitropyridine as a yellow solid (1.6 g).

An ice-cooled solution of the partially purified 2,3,6-trichloro-4-methyl-5-nitropyridine (1.1 g) in dry THF (10 mL) was treated with diisopropylethylamine (5.7 mmol, 1 mL) and cylopropylmethylamine (5.1 mmol, 0.44 mL). The solution was stirred at room temperature for 18 hours, then diluted with ethyl acetate and washed with saturated sodium bicarbonate solution. The solution was dried ($MgSO_4$) and the solvent was removed under reduced pressure. The crude product was partially purified by column chromatography (silica gel, gradient of ethyl acetate in isohexane) to give the intermediate 5,6-dichloro-N-(cyclopropylmethyl)-4-methyl-3-nitropyridin-2-amine as yellow oil (0.69 g).

A solution of the partially purified 5,6-dichloro-N-(cyclopropylmethyl)-4-methyl-3-nitropyridin-2-amine (0.69 g) in ethanol (30 mL) and water (3 mL) was treated with iron powder (12.5 mmol, 0.70 g) and ammonium chloride (1.34 g, 25 mmol). The suspension was heated at 90° C. with vigorous stirring for 1 hour. After cooling to room temperature, the mixture was filtered through Celite®. The filtrate was concentrated under reduced pressure and the crude product re-suspended in triemethylorthoformate (40 mL). Para-toluene sulfonic acid monohydrate (0.89 mmol, 0.17 g) was added and the suspension was stirred with heating at 100° C. for 5 hours. After cooling to room temperature, the suspension was diluted with ethyl acetate and washed with saturated aqueous sodium bicarbonate solution. The solution was dried (MgSO$_4$) and the solvent removed under reduced pressure. The crude product was purified by column chromatography (silica gel, gradient of ethyl acetate in isohexane) to give the title compound as a white solid (0.17 g).

Example 167

7-((6-Chloro-3-(cyclopropylmethyl)-7-methyl-3H-imidazo[4,5-b]pyridin-5-yl)amino)-4-methyl-2H-benzo[b][1,4]oxazin-3(4H)-one Using a similar procedure to that for Example 37, the title compound was prepared from 7-amino-4-methyl-2H-benzo[b][1,4]oxazin-3(4H)-one and 5, 6-dichloro-3-(cyclopropylmethyl)-7-methyl-3H-imidazo[4,5-b]pyridine in 41% yield.

Example 168

5-Imidazo[1,2-a]pyrimidin-3-ylpyridin-2-amine

A suspension of 5-(4,4,5,5-tetramethyl-1,3,2-dioxaborolan-2-yl)pyridin-2-amine (1.51 mmol, 0.33 g), 3-bromoimidazo[1,2-a]pyrimidine (1.51 mmol, 0.30 g), sodium carbonate (3.0 mmol, 0.32 g) and tetrakis(triphenylphosphine) palladium (0.076 mmol, 88 mg) in degassed DMF (6 mL) and water (2 mL) was heated under an atmosphere of nitrogen at 95° C. for 12 hours. The mixture was concentrated under reduced pressure and the residual solid triturated with methanol. The organic extract was filtered through a pad of silica, eluting with methanol. The solvent was removed from the filtrate under reduced pressure to give the crude title compound which was used without further purification.

Example 169

3-(Cyclopropylmethyl)-N-(5-imidazo[1,2-a]pyrimidin-3-yl-2-pyridyl)-7-methyl-imidazo[4,5-b]pyridin-5-amine

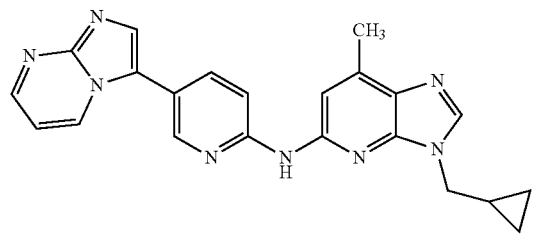 [SMILES: Cc1cc(Nc2ccc(-c3cnc4ncccn34)cn2)nc2c1ncn2CC1CC1]

Using a similar procedure to that for Example 37, the title compound was prepared from 5-imidazo[1,2-a]pyrimidin-3-ylpyridin-2-amine and 5-chloro-3-(cyclopropylmethyl)-7-methyl-3H-imidazo[4,5-b]pyridine in 24% yield.

Example 170

5-(5-Methyl-1,3,4-oxadiazol-2-yl)pyridin-2-amine

Using a similar procedure to that for Example 168, the title compound was prepared from 5-(4,4,5,5-tetramethyl-1,3,2-dioxaborolan-2-yl)pyridin-2-amine and 2-bromo-5-methyl-1,3,4-oxadiazole. The crude reaction mixture was filtered through Celite and the filter cake washed with dichloromethane containing 10% methanol. The filtrate was concentrated under reduced pressure and the crude product purified by column chromatography (silica gel, eluting with a gradient of dichloromethane to 10% (7M methanolic ammonia) in dichloromethane) to give the title compound as a yellow solid (0.08 g, 29%).

Example 171

3-(Cyclopropylmethyl)-7-methyl-N-[5-(5-methyl-1,3,4-oxadiazol-2-yl)-2-pyridyl]imidazo[4,5-b]pyridin-5-amine

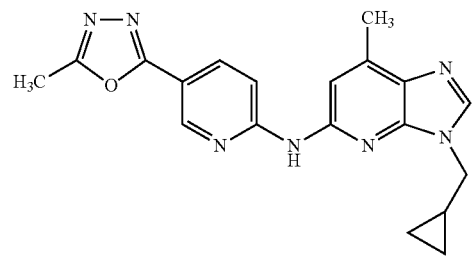 [SMILES: Cc1nnc(-c2ccc(Nc3cc(C)c4ncn(CC5CC5)c4n3)nc2)o1]

Using a similar procedure to that for Example 37, the title compound was prepared from 5-(5-methyl-1,3,4-oxadiazol-2-yl)pyridin-2-amine and 5-chloro-3-(cyclopropylmethyl)-7-methyl-3H-imidazo[4,5-b]pyridine in 62% yield.

Example 172

5-(1-Methyl-1H-imidazol-4-yl)pyridin-2-amine

Using a similar procedure to that for Example 37, the title compound (~80% purity) was prepared from 5-(4,4,5,5-tetramethyl-1,3,2-dioxaborolan-2-yl)pyridin-2-amine and 4-bromo-1-methyl-1H-imidazole in 38% yield.

Example 173

3-(Cyclopropylmethyl)-6-fluoro-7-methyl-N-[5-(1-methylimidazol-4-yl)-2-pyridyl]benzimidazol-5-amine

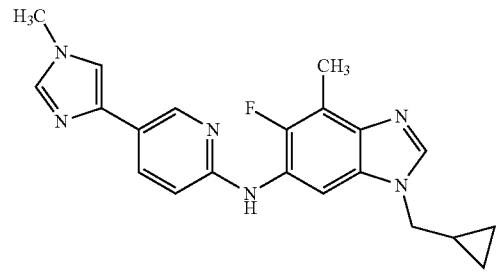 [SMILES: Cc1c(F)c(Nc2ccc(-c3cn(C)cn3)cn2)cc2c1ncn2CC1CC1]

Using a similar procedure to that for Example 37, the title compound was prepared from 5-(1-methyl-1H-imidazol-4-yl)pyridin-2-amine and 6-bromo-1-(cyclopropylmethyl)-5-fluoro-4-methyl-1H-benzo[d]imidazole in 22% yield.

Example 174

6-(4-Chloroimidazol-1-yl)pyridin-3-amine

A stirred suspension of 4-chloro-1H-imidazole (9.75 mmol, 1.0 g), 2-chloro-5-nitropyridine (9.75 mmol, 1.54 g) and potassium carbonate (11.70 mmol, 1.61 g) in DMF (10 mL) was heated at 80° C. for 3 hours. The mixture was cooled to room temperature and water was added. The resulting precipitate was filtered, washed with water and dried to give crude 6-(4-chloroimidazol-1-yl)-3-nitropyridine (1.94 g, 89%). The nitropyridine and iron powder (42.3 mmol, 2.4 g) were suspended in ethanol (28 mL) and acetic acid (6 mL) and the mixture heated at 90° C. for 12 hours. The suspension was cooled to room temperature and diluted with ethyl acetate. The mixture was filtered through Celite and the solvents removed under reduced pressure. The residual solid was washed with ether, filtered and dried to give the title compound (1.30 g, 78%).

Example 175

N-[6-(4-Chloroimidazol-1-yl)-3-pyridyl]-3-cyclopropyl-7-(trifluoromethyl)imidazo[4,5-b]pyridin-5-amine

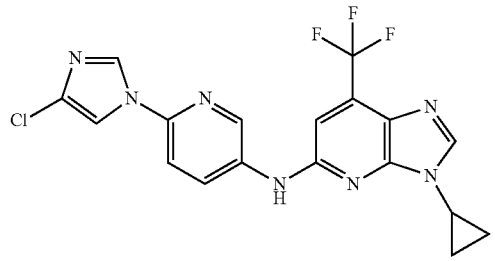 [SMILES: FC(F)(F)c1cc(Nc2ccc(-n3cnc(Cl)c3)nc2)nc2c1ncn2C1CC1]

Using a similar procedure to that for Example 37, the title compound was prepared from 6-(4-chloroimidazol-1-yl)pyridin-3-amine and 5-chloro-3-(cyclopropyl)-7-(trifluoromethyl)-3H-imidazo[4,5-b]pyridine in 82% yield.

Example 176

5-(4-Pyridyl)pyridin-2-amine

Using a similar procedure to that for Example 168, the title compound was prepared from 5-(4,4,5,5-tetramethyl-1,3,2-dioxaborolan-2-yl)pyridin-2-amine and 4-iodopyridine. After column chromatography, trituration of the product with diethyl ether gave the title compound in 56% yield.

Example 177

3-Cyclopropyl-7-methyl-N-[5-(4-pyridyl)-2 pyridyl]imidazo[4,5-b]pyridin-5-amine

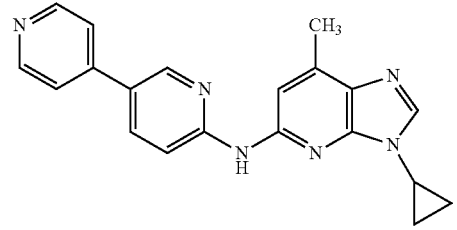 [SMILES: Cc1cc(Nc2ccc(-c3ccncc3)cn2)nc2c1ncn2C1CC1]

Using a similar procedure to that for Example 37, the title compound was prepared from 5-(4-pyridyl)pyridin-2-amine and 5-chloro-3-(cyclopropyl)-7-methyl-3H-imidazo[4,5-b]pyridine in 39% yield.

Liquid Chromatography-Mass Spectrometry
Method 1
LC-MS was performed on a Waters 2795 Alliance HT HPLC with Waters 2996 Diode Array Detector coupled to a Micromass ZQ, single quadrapole mass spectrometer using a Phenomenex Luna C18 (2) column (5 μm, 100×4.6 mm plus guard cartridge) with a linear gradient of 5-95% acetonitrile/water (with 0.1% formic acid in each mobile phase) within 3.5 minutes and held at 95% for 2.0 minutes.
Method 2
LC-MS was performed on a Waters 2795 Alliance. HT HPLC with Waters 2996 Diode Array Detector coupled to a Micromass ZQ, single quadrapole mass spectrometer using a Waters Xterra MS C18 column (5 μm, 100×4.6 mm plus guard cartridge) being initially held at 5% acetonitrile/water (with 10 mM ammonium bicarbonate in the aqueous mobile phase) for 0.5 minutes, followed by a linear gradient of 5-95% within 3.5 minutes and then held at 95% for 1.5 minutes.
High Performance Liquid Chromatography
Method 3
HPLC was performed on an Agilent 1100 HPLC system with an Agilent DAD detector using a Hichrom ACE 3 C18-AR column (100×4.6 mm) with a linear gradient of 2-100% acetonitrile/water (with 0.1% formic acid in each mobile phase) within 12 minutes and held at 100% for 3.4 minutes.
Method 4
HPLC was performed on an Agilent 1100 HPLC system with an Agilent DAD detector using a Hichrom ACE Excel 3 SuperC18 column (150×4.6 mm) with a linear gradient of 4.5-100% acetonitrile/water (with 10 mM ammonium bicarbonate in the aqueous mobile phase) within 9 minutes and held at 100% for 4.6 minutes.
Method 5
HPLC was performed on an Agilent 1100 HPLC system with an Agilent DAD detector using a Phenomenex Gemini NX C18 column (3 μm, 150×4.6 mm) with a linear gradient of 4.5-100% acetonitrile/water (with 10 mM ammonium bicarbonate in the aqueous mobile phase) within 9 minutes and held at 100% for 4.6 minutes.
Method 6
HPLC was performed on an Agilent 1100 HPLC system with an Agilent DAD detector using a Supelco Ascentis Express C18 column (2.7 μm, 150×4.6 mm) with a linear gradient of 4-100% acetonitrile/water (with 0.1% formic acid in each mobile phase) within 9 minutes and held at 100% for 4.6 minutes.
Method 7

HPLC was performed on a Waters Alliance Separations Module 2695 with a Waters 2487 Dual Wavelength Absorbance Detector using a YMC-Triart C18 column (S-5 μm, 12 nm 50×4.6 mm) with a linear gradient of 10-90% acetonitrile/water (with 0.05% TFA in each mobile phase) within 5 minutes and held at 90% for 1 minute The LCMS molecular ions identified for Example compounds and 1H NMR data are given in Table 1.

TABLE 1

| Example | Molecular Ion (MH+) | Retention Time | Method | $^1$H NMR data |
|---|---|---|---|---|
| 37 | 376 | 2.45 | Method 1 | $^1$H NMR (400 MHz, DMSO D6) 8.83 (1H, s), 8.58 (1H, s), 8.19 (1H, s), 7.43 (1H, d, J = 2.3 Hz), 7.26 (1H, d, J = 8.8 Hz), 7.20 (1H, dd, J = 2.3, 8.8 Hz), 6.94 (1H, s), 4.54 (2H, s), 4.03 (2H, d, J = 7.1 Hz), 2.76-2.69 (1H, m), 1.29-1.21 (1H, m), 1.12-1.05 (2H, m), 0.67-0.55 (4H, m), 0.45-0.40 (2H, m). |
| 38 | 386 | 2.96 | Method 2 | $^1$H NMR (400 MHz, DMSO D6) 9.17 (1H, s), 8.65 (1H, s), 8.23 (1H, s), 7.89 (1H, d, J = 2.3 Hz), 7.38 (1H, dd, J = 2.4, 9.0 Hz), 7.29 (1H, d, J = 8.8 Hz), 6.99 (1H, s), 4.05 (2H, d, J = 7.1 Hz), 3.32 (3H, s), 1.30-1.22 (1H, m), 0.61-0.55 (2H, m), 0.46-0.41 (2H, m). |
| 39 | 351 | 2.41 | Method 2 | $^1$H NMR (400 MHz, DMSO D6) 9.04 (1H, s), 8.60 (1H, s), 8.22-8.18 (2H, m), 7.92 (1H, d, J = 2.1 Hz), 6.96 (1H, s), 4.74 (2H, s), 4.05 (2H, d, J = 7.0 Hz), 1.30-1.16 (1H, m), 0.61-0.55 (2H, m), 0.46-0.40 (2H, m). |
| 40 | 349 | 7.82 | Method 3 | $^1$H NMR (400 MHz, DMSO D6) 9.16 (1H, s), 8.68 (1H, s), 8.44 (1H, s), 7.35-7.30 (1H, m), 7.29-7.26 (1H, m), 7.08 (1H, s), 7.02 (1H, s), 6.93 (1H, d, J = 8.7 Hz), 4.28 (2H, s), 4.07 (2H, d, J = 7.2 Hz), 3.17 (3H, s), 1.29-1.20 (1H, m), 0.60-0.54 (2H, m), 0.46-0.40 (2H, m). |
| 42 | 351 | 2.55 | Method 2 | $^1$H NMR (400 MHz, DMSO D6) 9.68 (1H, s), 8.40 (1H, s), 8.12 (1H, s), 7.62 (1H, d, J = 2.3 Hz), 7.47 (1H, dd, J = 2.4, 8.7 Hz), 7.17 (1H, d, J = 8.8 Hz), 4.68 (2H, s), 4.10 (2H, d, J = 7.1 Hz), 3.31 (3H, s), 1.42-1.34 (1H, m), 0.64-0.49 (4H, m). |
| 43 | 337 | 3.07 | Method 2 | $^1$H NMR (400 MHz, DMSO D6) 9.78 (1H, s), 8.40 (1H, s), 8.15 (1H, s), 8.03 (1H, d, J = 2.0 Hz), 7.32 (1H, d, J = 8.6 Hz), 7.27 (1H, dd, J = 2.0, 8.8 Hz), 4.14 (2H, d, J = 7.3 Hz), 3.39 (3H, s), 1.49-1.40 (1H, m), 0.63-0.51 (4H, m). |
| 45 | 351 | 2.60 | Method 2 | $^1$H NMR (400 MHz, CDCl$_3$) 8.81 (1H, s), 7.95 (1H, s), 7.59 (1H, d, J = 2.5 Hz), 7.26-7.20 (2H, m), 6.94 (1H, d, J = 8.6 Hz), 4.64 (2H, s), 4.03 (2H, d, J = 7.1 Hz), 3.38 (3H, s), 1.39-1.30 (1H, m), 0.75-0.69 (2H, m), 0.52-0.48 (2H, m). |

TABLE 1-continued

| Example | Molecular Ion (MH+) | Retention Time | Method | ¹H NMR data |
|---|---|---|---|---|
| 46 | 395 | 2.69 | Method 2 | ¹H NMR (400 MHz, DMSO D6) 9.59 (1H, s), 8.75 (1H, s), 8.23 (1H, s), 7.59 (1H, d, J = 2.3 Hz), 7.42 (1H, dd, J = 2.3, 8.8 Hz), 7.13 (1H, d, J = 8.8 Hz), 4.55 (2H, s), 4.04-3.94 (4H, m), 3.46 (2H, t, J = 5.7 Hz), 3.18 (3H, s), 1.32-1.23 (1H, m), 0.54-0.47 (2H, m), 0.43-0.37 (2H, m). |
| 52 | 418 | 2.80 | Method 2 | ¹H NMR (400 MHz, DMSO D6) 8.24 (1H, s), 8.04 (1H, s), 7.81 (1H, d, J = 2.3 Hz), 7.56-7.51 (2H, m), 7.00 (1H, d, J = 2.3 Hz), 4.71 (2H, s), 4.33 (2H, d, J = 5.8 Hz), 3.31 (3H, s), 2.68-2.55 (3H, m), 2.47-2.36 (2H, m). |
| 55 | 400 | 2.45 | Method 1 | ¹H NMR (400 MHz, DMSO D6) 8.81 (1H, s), 8.15 (1H, s), 8.13 (1H, s), 7.84 (1H, d, J = 1.8 Hz), 7.23 (1H, dd, J = 1.6, 8.2 Hz), 7.12 (1H, d, J = 8.3 Hz), 6.76 (1H, s), 4.26 (2H, d, J = 5.6 Hz), 3.32 (3H, s), 2.65-2.61 (6H, m), 2.48-2.35 (2H, m). |
| 58 | 367 | 2.89 | Method 2 | ¹H NMR (400 MHz, DMSO D6) 8.20 (1H, s), 7.82 (1H, s), 7.55-7.48 (2H, m), 6.95-6.90 (2H, m), 6.72 (1H, dd, J = 2.3, 8.6 Hz), 4.61 (2H, s), 4.07 (2H, d, J = 7.1 Hz), 3.25 (3H, s), 1.31-1.22 (1H, m), 0.59-0.53 (2H, m), 0.41 (2H, q, J = 5.0 Hz). |
| 59 | 411 | 8.98 | Method 3 | ¹H NMR (400 MHz, DMSO D6) 8.24 (1H, s), 7.89 (1H, s), 7.56-7.51 (2H, m), 7.15 (1H, d, J = 8.8 Hz), 6.72 (1H, dd, J = 2.3, 8.8 Hz), 6.65 (1H, d, J = 2.3 Hz), 4.60 (2H, s), 4.12-4.03 (4H, m), 3.55 (2H, dd, J = 5.7, 5.7 Hz), 3.28 (3H, s), 1.30-1.22 (1H, m), 0.62-0.55 (2H, m), 0.46-0.41 (2H, m). |
| 60 | 353 | 2.37 | Method 1 | ¹H NMR (400 MHz, CDCl₃) 7.93 (1H, s), 7.91 (1H, s), 7.52 (1H, d, J = 11.5 Hz), 7.21 (1H, d, J = 7.1 Hz), 6.82 (1H, s), 6.74 (2H, d, J = 1.8 Hz), 5.76 (1H, d, J = 2.8 Hz), 4.62 (2H, s), 3.92 (2H, d, J = 7.1 Hz), 1.30-1.21 (1H, m), 0.75-0.69 (2H, m), 0.39 (2H, dd, J = 5.1, 10.6 Hz). |
| 61 | 417 | 2.74 | Method 1 | ¹H NMR (400 MHz, DMSO D6) 8.22 (1H, s), 7.92 (1H, s), 7.54 (1H, s), 7.50 (1H, d, J = 7.8 Hz), 7.17 (1H, d, J = 8.6 Hz), 6.69 (1H, dd, J = 2.4, 8.7 Hz), 6.62 (1H, d, J = 2.3 Hz), 6.26 (1H, tt, J = 3.6, 55.6 Hz), 4.64 (2H, s), 4.41-4.30 (2H, m), 4.06 (2H, d, J = 7.1 Hz), 1.27-1.20 (1H, m), 0.58-0.51 (2H, m), 0.40 (2H, m). |
| 62 | 401 | 2.85 | Method 1 | ¹H NMR (400 MHz, DMSO D6) 8.30 (1H, s), 7.59 (1H, s), 7.56 (1H, s), 7.48-7.42 (2H, m), 6.36 (1H, d, J = 2.0 Hz), 4.61 (2H, s), 4.09 (2H, d, J = 7.1 Hz), 3.29 (3H, s), |

TABLE 1-continued

| Example | Molecular Ion (MH+) | Retention Time | Method | ¹H NMR data |
|---|---|---|---|---|
| | | | | 1.32-1.24 (1H, m), 0.60-0.54 (2H, m), 0.46-0.41 (2H, m). |
| 63 | 368 | 3.03 | Method 1 | ¹H NMR (400 MHz, DMSO D6) 8.58-8.55 (1H, m), 8.41 (1H, d, J = 7.3 Hz), 8.20 (1H, s), 7.93 (1H, s), 7.49 (1H, d, J = 11.7 Hz), 6.63 (1H, s), 4.73 (2H, s), 4.05 (2H, d, J = 7.1 Hz), 1.31-1.23 (1H, m), 0.61-0.54 (2H, m), 0.48-0.42 (2H, m). |
| 65 | 381 | 2.65 | Method 1 | ¹H NMR (400 MHz, CDCl₃) 7.85 (1H, s), 7.53 (1H, d, J = 11.7 Hz), 7.22 (1H, d, J = 7.3 Hz), 6.91 (1H, d, J = 8.6 Hz), 6.83-6.76 (2H, m), 5.77 (1H, s), 4.62 (2H, s), 4.21-4.15 (2H, m), 3.37 (3H, s), 1.75-1.68 (2H, m), 0.65-0.56 (1H, m), 0.49-0.43 (2H, m). |
| 66 | 438 | 2.60 | Method 1 | ¹H NMR (400 MHz, CDCl₃) 7.85 (1H, s), 7.52 (1H, d, J = 11.1 Hz), 7.23 (1H, d, J = 7.1 Hz), 6.87 (1H, d, J = 8.6 Hz), 6.79 (1H, d, J = 2.3 Hz), 6.76-6.72 (1H, m), 5.78 (1H, d, J = 2.0 Hz), 4.77 (2H, dd, J = 6.3, 7.6 Hz), 4.60-4.58 (4H, m), 4.28 (2H, d, J = 7.3 Hz), 4.17 (2H, dd, J = 6.7, 6.7 Hz), 3.48-3.39 (1H, m), 1.71 (2H, q, J = 6.7 Hz), 0.64-0.56 (1H, m), 0.49-0.43 (2H, m). |
| 67 | 382 | 2.60 | Method 1 | ¹H NMR (400 MHz, CDCl₃) 8.22 (0.1H, s), 7.90 (1H, d, J = 2.3 Hz), 7.87 (1H, s), 7.54 (1H, d, J = 11.0 Hz), 7.15 (1H, d, J = 7.1 Hz), 7.06 (1H, d, J = 2.5 Hz), 5.79-5.74 (1H, m), 4.69 (2H, s), 4.20-4.15 (2H, m), 3.48 (3H, s), 1.71 (2H, dd, J = 6.8, 13.6 Hz), 0.64-0.55 (1H, m), 0.49-0.43 (2H, m), 0.03--0.02 (2H, m). |
| 70 | 385 | 3.55 | Method 2 | ¹H NMR (400 MHz, DMSO D6) 8.44 (1H, s), 8.18 (1H, s), 7.60 (1H, d, J = 8.6 Hz), 7.37 (1H, d, J = 1.8 Hz), 7.29 (1H, d, J = 8.8 Hz), 7.03-6.98 (2H, m), 6.93 (1H, d, J = 2.3 Hz), 4.09 (2H, d, J = 6.8 Hz), 3.42 (3H, s), 1.32-1.24 (1H, m), 0.62-0.55 (2H, m), 0.44 (2H, q, J = 5.0 Hz). |
| 71 | 364 | 3.27 | Method 2 | ¹H NMR (400 MHz, DMSO D6) 8.44 (1H, s), 8.18 (1H, s), 7.60 (1H, d, J = 8.6 Hz), 7.37 (1H, d, J = 2.0 Hz), 7.29 (1H, d, J = 9.1 Hz), 7.04-6.98 (2H, m), 6.94 (1H, d, J = 2.5 Hz), 4.09 (2H, d, J = 7.1 Hz), 3.43 (3H, s), 1.32-1.23 (1H, m), 0.62-0.55 (2H, m), 0.47-0.41 (2H, m). |
| 75 | 389 | 2.58 | Method 1 | ¹NMR (400 MHz, DMSO D6) 8.12 (1H, s), 7.51 (1H, s), 7.35 (1H, s), 7.23 (1H, s), 6.97 (1H, d, J = 8.8 Hz), 6.58 (1H, dd, J = 2.4, 8.7 Hz), 6.51 (1H, d, J = 2.5 Hz), 4.56 (2H, s), 4.02 (2H, d, J = 7.1 Hz), 3.23 (3H, s), 2.05-1.96 (1H, m), |

TABLE 1-continued

| Example | Molecular Ion (MH+) | Retention Time | Method | ¹H NMR data |
|---|---|---|---|---|
| | | | | 1.25-1.16 (1H, m), 0.91-0.84 (2H, m), 0.65-0.60 (2H, m), 0.56-0.49 (2H, m), 0.37 (2H, q, J = 5.0 Hz). |
| 77 | 390 | 3.38 | Method 2 | ¹H NMR (400 MHz, DMSO D6) 8.07 (1H, s), 7.63-7.59 (2H, m), 7.30 (1H, s), 7.18 (1H, s), 6.79 (1H, d, J = 2.0 Hz), 4.61 (2H, s), 3.95 (2H, d, J = 6.6 Hz), 3.21 (3H, s), 1.95-1.88 (1H, m), 1.19-1.09 (1H, m), 0.85-0.78 (2H, m), 0.59-0.54 (2H, m), 0.48-0.41 (2H, m), 0.30 (2H, q, J = 4.9 Hz). |
| 81 | 379 | 8.89 | Method 3 | ¹H NMR (400 MHz, DMSO D6) 8.09 (1H, s), 7.43-7.39 (2H, m), 7.28 (1H, s), 7.04 (1H, d, J = 8.6 Hz), 6.84 (1H, dd, J = 1.9, 8.7 Hz), 6.76 (1H, d, J = 2.0 Hz), 4.61 (2H, s), 4.04 (2H, d, J = 6.8 Hz), 3.88 (3H, s), 3.28 (3H, s), 1.26-1.19 (1H, m), 0.61-0.55 (2H, m), 0.44-0.38 (2H, m). |
| 82 | 365 | 2.98 | Method 2 | ¹H NMR (400 MHz, DMSO D6) 9.29 (1H, s), 8.00 (1H, s), 7.32 (1H, s), 7.27 (1H, s), 7.07 (1H, s), 6.99 (1H, d, J = 8.8 Hz), 6.79 (1H, dd, J = 2.3, 8.6 Hz), 6.70 (1H, d, J = 2.5 Hz), 4.57 (2H, s), 3.98 (2H, d, J = 6.8 Hz), 3.24 (3H, s), 1.25-1.16 (1H, m), 0.57-0.51 (2H, m), 0.40-0.34 (2H, m). |
| 83 | 415 | 2.72 | Method 1 | ¹H NMR (400 MHz, DMSO D6) 8.11 (1H, s), 7.75 (1H, s), 7.45 (1H, s), 7.29 (1H, s), 7.22 (1H, d, J = 8.8 Hz), 6.95 (1H, dd, J = 2.4, 9.0 Hz), 6.87 (1H, d, J = 2.5 Hz), 4.04 (2H, d, J = 7.1 Hz), 3.84 (3H, s), 3.35 (3H, s), 1.27-1.19 (1H, m), 0.57-0.51 (2H, m), 0.39 (2H, q, J = 5.0 Hz). |
| 86 | 382 | 2.55 | Method 4 | ¹H NMR (400 MHz, DMSO D6) 8.19 (1H, s), 7.98 (1H, s), 7.82 (1H, d, J = 2.3 Hz), 7.33 (1H, d, J = 7.1 Hz), 7.01 (1H, d, J = 2.3 Hz), 4.73 (2H, s), 4.07 (2H, d, J = 7.1 Hz), 2.50-2.48 (3H, m), 1.28-1.20 (1H, m), 0.58-0.52 (2H, m), 0.43-0.38 (2H, m). |
| 87 | 382 | 2.34 | Method 1 | ¹H NMR (400 MHz, DMSO D6) 8.49 (1H, s), 8.20 (1H, d, J = 7.1 Hz), 8.16 (1H, s), 7.93 (1H, s), 6.61 (1H, s), 4.72 (2H, s), 4.04 (2H, d, J = 7.1 Hz), 2.51 (3H, s), 2.47 (3H, s), 1.30-1.21 (1H, m), 0.59-0.53 (2H, m), 0.43 (2H, q, J = 5.1 Hz). |
| 88 | 363 | 3.12 | Method 3 | ¹H NMR (400 MHz, CDCl₃) 8.32 (1H, d, J = 2.8 Hz), 8.24 (1H, s), 7.95 (1H, s), 7.58 (1H, s), 7.52 (1H, dd, J = 2.9, 8.7 Hz), 7.29 (1H, d, J = 8.8 Hz), 7.20 (1H, s), 7.09 (1H, d, J = 6.8 Hz), 5.91 (1H, d, J = 1.8 Hz), 3.93 (2H, d, J = 7.1 Hz), 2.62 (3H, d, J = 2.0 Hz), 1.31-1.23 (1H, m), 0.74-0.68 (2H, m), 0.42-0.37 (2H, m). |

TABLE 1-continued

| Example | Molecular Ion (MH+) | Retention Time | Method | ¹H NMR data |
|---|---|---|---|---|
| 91 | 364 | 7.70 | Method 3 | ¹H NMR (400 MHz, DMSO D6) 8.92 (1H, s), 8.08 (1H, s), 7.98 (2H, s), 7.02 (1H, s), 6.46 (1H, s), 4.75 (2H, s), 4.03 (2H, d, J = 7.1 Hz), 3.32 (3H, s), 1.32-1.23 (1H, m), 0.61-0.55 (2H, m), 0.48-0.42 (2H, m). |
| 93 | 385 | 9.72 | Method 3 | ¹H NMR (400 MHz, DMSO D6) 8.21 (1H, s), 7.98 (1H, s), 7.26 (1H, d, J = 5.8 Hz), 6.94-6.90 (2H, m), 6.74 (1H, dd, J = 2.5, 8.6 Hz), 4.59 (2H, s), 4.04 (2H, d, J = 7.1 Hz), 3.23 (3H, s), 1.26-1.18 (1H, m), 0.56-0.50 (2H, m), 0.37 (2H, q, J = 4.9 Hz). |
| 94 | 355 | 3.46 | Method 1 | ¹H NMR (400 MHz, DMSO D6) 8.28 (1H, s), 8.25 (1H, s), 7.51 (1H, d, J = 8.6 Hz), 7.40-7.37 (1H, m), 7.26 (1H, d, J = 2.0 Hz), 7.07 (1H, dd, J = 1.9, 8.5 Hz), 4.08 (2H, d, J = 7.1 Hz), 2.57 (3H, s), 1.30-1.22 (1H, m), 0.60-0.54 (2H, m), 0.41 (2H, q, J = 5.0 Hz). |
| 95 | 384 | 3.35 | Method 2 | ¹H NMR (400 MHz, DMSO D6) 8.57 (1H, s), 8.34 (1H, s), 7.88 (1H, s), 7.49 (1H, d, J = 5.8 Hz), 7.44-7.37 (2H, m), 7.08 (1H, s), 6.94-6.85 (2H, m), 4.11 (2H, d, J = 7.1 Hz), 1.31-1.23 (1H, m), 0.59-0.52 (2H, m), 0.42 (2H, q, J = 4.9 Hz). |
| 99 | 372 | 3.09 | Method 1 | ¹H NMR (400 MHz, DMSO D6) 8.35 (1H, s), 8.12 (1H, s), 8.08 (1H, s), 7.44 (1H, s), 7.01-6.96 (3H, m), 4.05 (2H, d, J = 7.0 Hz), 3.24 (3H, s), 2.84-2.77 (2H, m), 2.54 (2H, m, obscured by DMSO peak), 1.23-1.14 (1H, m), 0.57-0.50 (2H, m), 0.38 (2H, q, J = 5.0 Hz). |
| 103 | 398 | 2.82 | Method 2 | ¹H NMR (400 MHz, DMSO D6) 8.38 (1H, s), 8.26 (1H, s), 8.15 (1H, s), 7.58 (1H, d, J = 2.3 Hz), 7.53 (1H, dd, J = 2.4, 8.7 Hz), 7.10 (1H, d, J = 8.6 Hz), 4.71 (1H, q, J = 6.7 Hz), 4.01 (2H, d, J = 6.6 Hz), 3.29 (3H, s), 1.43 (3H, d, J = 6.8 Hz), 1.34 (1H, m), 0.57-0.51 (2H, m), 0.47-0.42 (2H, m). |
| 104 | 376 | 2.82 | Method 1 | ¹H NMR (400 MHz, DMSO D6) 8.26 (1H, s), 8.14 (1H, s), 8.03 (1H, s), 7.43 (1H, d, J = 2.3 Hz), 7.37 (1H, dd, J = 2.3, 8.8 Hz), 7.11-6.98 (2H, m), 5.75 (1H, d, J = 16.9 Hz), 5.27 (1H, d, J = 11.4 Hz), 4.55 (2H, s), 3.93 (2H, d, J = 7.1 Hz), 3.21 (3H, s), 1.31-1.23 (1H, m), 0.51-0.43 (2H, m), 0.40-0.33 (2H, m). |
| 106 | 366 | 2.37 | Method 2 | ¹H NMR (400 MHz, DMSO D6) 9.23 (1H, s), 8.15 (1H, s), 7.85 (1H, d, J = 8.7 Hz), 7.56 (1H, d, J = 2.3 Hz), 7.45 (1H, dd, J = 2.4, 8.8 Hz), 7.10 (1H, d, J = 8.9 Hz), 6.74 (1H, d, J = 8.7 Hz), 4.70-4.63 (4H, m), 4.51-4.46 (4H, |

TABLE 1-continued

| Example | Molecular Ion (MH+) | Retention Time | Method | ¹H NMR data |
|---|---|---|---|---|
| 108 | 350 | 8.81 | Method 3 | m), 3.63-3.54 (1H, m), 3.28 (3H, s). ¹H NMR (400 MHz, DMSO D6) 9.19 (1H, s), 8.12 (1H, d, J = 2.4 Hz), 8.06 (1H, s), 7.78 (1H, d, J = 8.7 Hz), 7.05 (1H, dd, J = 2.4, 8.7 Hz), 6.87 (1H, d, J = 8.5 Hz), 6.66 (1H, d, J = 8.8 Hz), 4.53 (2H, s), 3.99 (2H, d, J = 7.2 Hz), 3.26 (3H, s), 1.37-1.28 (1H, m), 0.49-0.42 (2H, m), 0.41-0.33 (2H, m). |
| 109 | 336 | 2.88 | Method 2 | ¹H NMR (400 MHz, DMSO D6) 9.27 (1H, s), 8.13 (1H, d, J = 2.1 Hz), 8.08 (1H, s), 7.80 (1H, d, J = 8.7 Hz), 7.17 (1H, d, J = 8.7 Hz), 7.09 (1H, dd, J = 2.1, 8.7 Hz), 6.69 (1H, d, J = 8.7 Hz), 4.02 (2H, d, J = 7.3 Hz), 1.41-1.32 (1H, m), 0.50-0.36 (4H, m). |
| 110 | 319 | 1.92 | Method 7 | ¹H NMR (300 MHz, CDCl₃) 7.96 (2H, d, J = 2.0 Hz), 7.93 (1H, s), 7.88 (1H, d, J = 8.6 Hz), 7.82 (1H, s), 7.73 (1H, d, J = 8.6 Hz), 7.15 (1H, dd, J = 8.6, 2.0 Hz), 6.74 (1H, d, J = 8.6 Hz), 6.70 (1H, s), 4.08 (2H, d, J = 7.1 Hz), 3.84 (3H, s), 1.50-1.36 (1H, m), 0.73-0.63 (2H, m), 0.53-0.43 (2H, m) |
| 111 | 351 | 2.41 | Method 2 | ¹H NMR (400 MHz, DMSO D6) 9.46 (1H, s), 8.46 (1H, d, J = 2.3 Hz), 8.19 (1H, s), 8.11 (1H, d, J = 2.3 Hz), 7.92 (1H, d, J = 8.8 Hz), 6.78 (1H, d, J = 8.8 Hz), 4.83 (2H, s), 4.10 (2H, d, J = 7.1 Hz), 3.36 (3H, s, obscured by solvent), 1.47-1.38 (1H, m), 0.61-0.52 (2H, m), 0.49-0.41 (2H, m). |
| 116 | 368 | 2.85 | Method 2 | ¹H NMR (400 MHz, DMSO D6) 8.85 (1H, d, J = 2.0 Hz), 8.16 (1H, s), 7.87 (1H, d, J = 12.0 Hz), 7.61 (1H, d, J = 2.3 Hz), 7.57 (1H, dd, J = 2.3, 8.8 Hz), 7.04 (1H, d, J = 8.8 Hz), 4.57 (2H, s), 3.97 (2H, d, J = 7.1 Hz), 3.21 (3H, s), 1.31-1.23 (1H, m), 0.51-0.45 (2H, m), 0.42-0.36 (2H, m). |
| 118 | 364 | 3.03 | Method 3 | ¹H NMR (400 MHz, DMSO D6) 8.74 (1H, s), 8.10 (1H, s), 7.46-7.42 (1H, m), 7.24-7.17 (1H, m), 7.04 (1H, d, J = 8.6 Hz), 6.78 (1H, s), 4.61 (2H, s), 3.99 (2H, d, J = 7.1 Hz), 3.26 (3H, s), 2.63 (3H, s), 1.25-1.15 (1H, m), 0.59-0.52 (2H, m), 0.43-0.38 (2H, m). |
| 119 | 366 | 3.18 | Method 2 | ¹H NMR (400 MHz, CDCl₃) 10.04 (1H, s), 8.44 (1H, s), 7.83 (1H, s), 7.01-6.97 (3H, m), 6.70 (1H, s), 4.64 (2H, s), 4.03 (2H, dd, J = 7.1, 7.1 Hz), 3.38 (3H, s), 2.86 (3H, s), 1.84-1.76 (2H, m), 1.38-1.29 (2H, m), 0.96 (3H, t, J = 7.3 Hz). |
| 120 | 365 | 2.40 | Method 1 | ¹H NMR (400 MHz, DMSO D6) 8.25 (1H, d, J = 2.3 Hz), |

TABLE 1-continued

| Example | Molecular Ion (MH+) | Retention Time | Method | ¹H NMR data |
|---|---|---|---|---|
| | | | | 8.14 (1H, s), 7.93 (1H, d, J = 2.3 Hz), 6.79 (1H, s), 4.73 (2H, s), 4.69 (1H, s), 4.01 (2H, d, J = 7.0 Hz), 3.32 (3H, s), 2.64 (3H, s), 1.28-1.19 (1H, m), 0.59-0.52 (2H, m), 0.43-0.38 (2H, m). |
| 121 | 398 | 9.22 | Method 2 | ¹H NMR (400 MHz, DMSO D6) 7.93 (1H, s), 7.71 (1H, s), 7.64 (1H, s), 7.04 (1H, s), 6.79 (1H, s), 4.44 (2H, s), 3.77 (2H, d, J = 7.1 Hz), 3.06 (3H, s), 2.40 (3H, s), 1.08-0.99 (1H, m), 0.37-0.30 (2H, m), 0.23-0.17 (2H, m). |
| 122 | 422 | 2.35 | Method 1 | ¹H NMR (400 MHz, DMSO D6) 8.72 (1H, s), 8.10 (1H, s), 7.43-7.36 (2H, m), 7.17-7.12 (1H, m), 6.78 (1H, s), 4.59 (2H, s), 4.57 (1H, s), 4.00 (2H, d, J = 7.1 Hz), 3.88 (2H, s), 2.63 (3H, s), 1.26-1.19 (1H, m), 1.12 (6H, s), 0.58-0.53 (2H, m), 0.44-0.39 (2H, m). |
| 123 | 408 | 8.50 | Method 3 | ¹H NMR (400 MHz, DMSO D6) 8.75 (1H, s), 8.17 (1H, s), 8.10 (1H, s), 7.44 (1H, d, J = 2.3 Hz), 7.21-7.17 (1H, m), 7.15-7.12 (1H, m), 6.79 (1H, s), 4.59 (2H, s), 4.08-3.98 (4H, m), 3.53 (2H, t, J = 5.8 Hz), 2.63 (3H, s), 1.28-1.19 (1H, m), 0.59-0.53 (2H, m), 0.43-0.38 (2H, m). |
| 124 | 365 | 2.34 | Method 1 | ¹H NMR (400 MHz, DMSO D6) 9.54 (1H, s), 8.20 (1H, s), 7.94 (1H, s), 7.55 (1H, d, J = 8.6 Hz), 7.28 (1H, d, J = 8.6 Hz), 4.87 (2H, s), 4.05 (2H, d, J = 7.1 Hz), 3.29 (3H, s), 2.69 (3H, s), 1.32-1.24 (1H, m), 0.67-0.61 (2H, m), 0.54-0.49 (2H, m). |
| 125 | 334 | 2.36 | Method 1 | ¹H NMR (400 MHz, CDCl₃) 7.84 (1H, s), 7.59-7.54 (2H, m), 7.14 (1H, dd, J = 2.0, 8.6 Hz), 6.73 (1H, s), 6.60 (1H, s), 3.87 (2H, d, J = 6.8 Hz), 2.80 (3H, s), 2.63 (3H, s), 1.28-1.19 (1H, m), 0.73-0.67 (2H, m), 0.38 (2H, q, J = 5.3 Hz). |
| 126 | 390 | 8.56 | Method 3 | ¹H NMR (400 MHz, CDCl₃) 7.87 (1H, s), 7.30 (1H, s), 7.17 (1H, s), 7.00 (1H, d, J = 2.3 Hz), 6.97-6.93 (1H, m), 6.72 (1H, s), 4.57 (2H, s), 3.88 (2H, d, J = 6.8 Hz), 2.80 (3H, s), 2.78-2.71 (1H, m), 1.27-1.13 (3H, m), 0.85-0.69 (4H, m), 0.43-0.36 (2H, m). |
| 127 | 379 | 8.53 | Method 3 | ¹H NMR (400 MHz, CDCl₃) 8.47 (0.3H, s), 8.04 (1H, d, J = 2.3 Hz), 7.89 (1H, s), 7.61 (1H, s), 7.37 (1H, d, J = 2.3 Hz), 6.65 (1H, s), 4.68 (2H, s), 4.19 (2H, q, J = 7.1 Hz), 3.89 (2H, d, J = 7.1 Hz), 2.81 (3H, s), 1.30 (3H, t, J = 7.1 Hz), 1.27-1.21 (1H, m), 0.76-0.70 (2H, m), 0.40 (2H, q, J = 5.2 Hz). |

TABLE 1-continued

| Example | Molecular Ion (MH+) | Retention Time | Method | $^1$H NMR data |
|---|---|---|---|---|
| 128 | 414 | 2.52 | Method 1 | $^1$H NMR (400 MHz, DMSO D6) 8.84 (1H, s), 8.15 (1H, s), 7.46 (1H, s), 7.20 (2H, s), 6.82 (1H, s), 6.27 (1H, tt, J = 3.9, 55.1 Hz), 4.67 (2H, s), 4.43-4.32 (2H, m), 4.01 (2H, d, J = 7.1 Hz), 1.28-1.20 (1H, m), 0.59-0.52 (2H, m), 0.41 (2H, m). |
| 129 | 396 | 2.45 | Method 1 | $^1$H NMR (400 MHz, DMSO D6) 8.81 (1H, s), 8.13 (1H, s), 7.48 (1H, d, J = 2.4 Hz), 7.22 (1H, dd, J = 2.4, 8.8 Hz), 7.15 (1H, d, J = 8.8 Hz), 6.81 (1H, s), 4.67 (2H, s), 4.72-4.58 (2H, m), 4.29-4.20 (2H, m), 4.03 (2H, d, J = 7.2 Hz), 2.64 (3H, s), 1.26-122 (1H, m), 0.59-0.52 (2H, m), 0.45-0.42 (2H, m). |
| 130 | 398 | 8.86 | Method 3 | $^1$H NMR (400 MHz, DMSO D6) 9.08 (1H, s), 8.18 (1H, s), 7.52-7.47 (2H, m), 6.83 (1H, s), 4.59 (2H, s), 4.05 (2H, d, J = 7.1 Hz), 3.41 (3H, s), 2.67 (3H, s), 1.29-1.21 (1H, m), 0.61-0.55 (2H, m), 0.46-0.41 (2H, m). |
| 132 | 365 | 3.18 | Method 1 | $^1$H NMR (400 MHz, DMSO D6) 9.51 (1H, s), 8.14 (1H, s), 7.59 (1H, d, J = 2.3 Hz), 7.48 (1H, dd, J = 2.3, 8.8 Hz), 7.01 (1H, d, J = 8.8 Hz), 4.55 (2H, s), 3.94 (2H, d, J = 7.1 Hz), 3.20 (3H, s), 2.54 (3H, s), 1.29-1.21 (1H, m), 0.51-0.37 (4H, m). |
| 133 | 449 | 10.21 | Method 4 | $^1$H NMR (400 MHz, DMSO D6) 8.37 (1H, s), 8.28 (1H, s), 7.96 (1H, s), 7.55 (1H, s), 6.32 (1H, tt, J = 3.7, 55.1 Hz), 4.78 (2H, s), 4.49 (2H, dt, J = 3.5, 15.2 Hz), 4.00 (2H, d, J = 7.1 Hz), 2.64 (3H, s), 1.36-1.28 (1H, m), 0.60-0.54 (2H, m), 0.50-0.44 (2H, m). |
| 134 | 399 | 3.54 | Method 2 | $^1$H NMR (400 MHz, CDCl$_3$) 8.51 (1H, s), 7.92 (1H, s), 7.56 (1H, s), 7.01 (1H, s), 4.65 (2H, s), 4.03 (2H, d, J = 7.3 Hz), 3.35 (3H, s), 2.77 (3H, s), 1.39-1.28 (1H, m), 0.74-0.68 (2H, m), 0.52-0.48 (2H, m). |
| 135 | 379 | 3.36 | Method 1 | $^1$H NMR (400 MHz, CDCl$_3$) 7.89 (1H, s), 7.61 (1H, d, J = 2.3 Hz), 7.25-7.22 (1H, m), 7.11 (1H, s), 6.96 (1H, d, J = 8.8 Hz), 4.61 (2H, s), 4.04-3.98 (4H, m), 2.74 (3H, s), 1.33-1.27 (4H, m), 0.74-0.68 (2H, m), 0.51-0.47 (2H, m). |
| 136 | 401 | 3.69 | Method 1 | $^1$H NMR (400 MHz, CDCl$_3$) 7.99 (1H, d, J = 2.3 Hz), 7.92 (1H, s), 7.31 (1H, dd, J = 2.5, 8.8 Hz), 7.19 (1H, s), 7.03 (1H, d, J = 8.8 Hz), 4.04 (2H, d, J = 7.1 Hz), 3.49 (3H, s), 2.75 (3H, s), 1.38-1.30 (1H, m), 0.75-0.69 (2H, m), 0.50 (2H, q, J = 5.2 Hz). |
| 137 | 421 | 3.03 | Method 1 | $^1$H NMR (400 MHz, DMSO D6) 9.62 (1H, s), 8.23 (1H, s), 7.68 (1H, d, J = 2.3 Hz), |

TABLE 1-continued

| Example | Molecular Ion (MH+) | Retention Time | Method | ¹H NMR data |
|---|---|---|---|---|
| | | | | 7.54 (1H, dd, J = 2.0, 8.8 Hz), 7.16 (1H, d, J = 8.8 Hz), 4.64-4.58 (4H, m), 4.39 (2H, m), 4.26 (2H, d, J = 7.1 Hz), 4.02 (2H, d, J = 7.1 Hz), 3.33-3.26 (1H, m), 2.61 (3H, s), 1.37-1.29 (1H, m), 0.59-0.53 (2H, m), 0.50-0.44 (2H, m). |
| 138 | 397 | 9.04 | Method 5 | ¹H NMR (400 MHz, DMSO D6) 9.62 (1H, s), 8.24 (1H, s), 7.70 (1H, d, J = 2.3 Hz), 7.55 (1H, dd, J = 2.3, 8.8 Hz), 7.19 (1H, d, J = 8.8 Hz), 4.66 (3H, s), 4.65 (2H, td, J = 4.9, 47.3 Hz), 4.32-4.20 (2H, m), 4.03 (2H, d, J = 7.3 Hz), 2.63 (3H, s), 1.38-1.31 (1H, m), 0.60-0.54 (2H, m), 0.51-0.45 (2H, m). |
| 141 | 434 | 9.14 | Method 3 | ¹H NMR (400 MHz, CDCl₃) 8.20 (1H, s), 8.01 (1H, s), 7.74-7.71 (1H, m), 7.21 (1H, d, J = 8.6 Hz), 6.66 (1H, s), 6.55 (1H, d, J = 8.6 Hz), 4.82 (2H, s), 4.01 (2H, d, J = 7.1 Hz), 3.34 (3H, s), 1.36-1.27 (1H, m), 0.79-0.72 (2H, m), 0.47 (2H, q, J = 5.2 Hz). |
| 142 | 469 | 3.88 | Method 2 | ¹H NMR (400 MHz, CDCl₃) 8.02 (1H, s), 7.75 (1H, d, J = 1.3 Hz), 7.30 (1H, s), 7.04-6.99 (2H, m), 6.97-6.93 (1H, m), 5.94 (1H, s), 3.95 (2H, d, J = 6.8 Hz), 3.48 (3H, s), 1.30-1.22 (1H, m), 0.77-0.71 (2H, m), 0.41 (2H, q, J = 5.2 Hz). |
| 143 | 434 | 3.48 | Method 2 | ¹H NMR (400 MHz, CDCl₃) 7.98 (1H, s), 7.93 (1H, d, J = 2.3 Hz), 7.75-7.73 (1H, m), 7.16 (1H, s), 7.11 (1H, d, J = 2.5 Hz), 5.82 (1H, s), 4.70 (2H, s), 3.92 (2H, d, J = 6.8 Hz), 3.49 (3H, s), 1.29-1.21 (1H, m), 0.76-0.70 (2H, m), 0.39 (2H, q, J = 5.2 Hz). |
| 145 | 382 | 2.94 | Method 1 | ¹H NMR (400 MHz, CDCl₃) 7.90 (1H, s), 7.79 (1H, d, J = 2.5 Hz), 7.51 (1H, d, J = 8.8 Hz), 7.14 (1H, t, J = 8.1 Hz), 6.93 (1H, d, J = 2.5 Hz), 5.61 (1H, s), 4.63 (2H, s), 4.20-4.12 (4H, m), 1.40-1.33 (1H, m), 1.30-1.25 (3H, m), 0.72-0.66 (2H, m), 0.43 (2H, q, J = 5.2 Hz). |
| 147 | 379 | 2.42 | Method 1 | ¹H NMR (400 MHz, CDCl₃) 8.02 (1H, d, J = 2.3 Hz), 7.78 (1H, s), 7.43 (1H, d, J = 2.3 Hz), 6.61 (1H, s), 6.40 (1H, s), 4.70 (2H, s), 4.16-4.11 (2H, m), 3.49 (3H, s), 2.79 (3H, s), 1.70 (2H, q, J = 6.7 Hz), 0.63-0.55 (1H, m), 0.50-0.44 (2H, m). |

TABLE 1-continued

| Example | Molecular Ion (MH+) | Retention Time | Method | $^1$H NMR data |
|---|---|---|---|---|
| 148 | 379 | 3.02 | Method 2 | $^1$H NMR (400 MHz, DMSO D6) 9.46 (1H, s), 8.12 (1H, s), 7.98 (1H, s), 7.97 (1H, s), 7.13 (1H, s), 4.74 (2H, s), 4.21 (2H, t, J = 6.7 Hz), 3.30 (3H, s), 2.63 (3H, s), 1.68 (2H, dd, J = 6.7, 13.8 Hz), 0.64-0.55 (1H, m), 0.41-0.35 (2H, m), 0.02--0.03 (2H, m). |
| 151 | 419 | 3.57 | Method 6 | $^1$H NMR (400 MHz, CDCl$_3$) 8.10 (1H, s), 7.81 (1H, d, J = 8.6 Hz), 7.40 (1H, s), 7.33 (1H, d, J = 8.3 Hz), 7.24 (1H, s), 4.85 (2H, s), 4.11 (2H, d, J = 7.1 Hz), 3.37 (3H, s), 1.43-1.34 (1H, m), 0.75-0.69 (2H, m), 0.52-0.48 (2H, m). |
| 155 | 384 | 2.60 | Method 1 | $^1$H NMR (400 MHz, DMSO D6) 10.67 (1H, s), 8.18 (1H, s), 8.10 (1H, s), 7.87 (1H, s), 6.95 (1H, s), 6.75 (1H, s), 4.59 (2H, s), 3.96 (2H, d, J = 7.1 Hz), 2.47 (3H, s), 1.34-1.26 (1H, m), 0.55-0.49 (2H, m), 0.41 (2H, q, J = 5.0 Hz). |
| 156 | 448 | 3.03 | Method 1 | $^1$H NMR (400 MHz, DMSO D6) 8.27 (1H, s), 8.13 (1H, s), 8.04 (1H, s), 7.48 (1H, s), 6.84 (1H, s), 6.29 (1H, tt, J = 3.6, 55.2 Hz), 4.72 (2H, s), 4.50-4.39 (2H, m), 3.98 (2H, d, J = 7.1 Hz), 2.48 (3H, s), 1.35-1.27 (1H, m), 0.55-0.39 (4H, m). |
| 157 | 346 | 2.57 | Method 4 | $^1$H NMR (400 MHz, CDCl$_3$) 8.35 (1H, d, J = 2.8 Hz), 8.30 (1H, d, J = 9.1 Hz), 7.98 (1H, s), 7.80 (1H, s), 7.69 (1H, dd, J = 2.8, 8.8 Hz), 7.59 (1H, s), 7.25-7.22 (2H, m), 6.85 (1H, s), 4.09 (2H, d, J = 7.3 Hz), 2.66 (3H, s), 1.43-1.34 (1H, m), 0.72-0.66 (2H, m), 0.50-0.46 (2H, m). |
| 158 | 346 | 2.06 | Method 2 | $^1$H NMR (400 MHz, CDCl$_3$) 8.71 (1H, d, J = 2.5 Hz), 8.30-8.25 (2H, m), 7.96 (1H, s), 7.61 (1H, t, J = 1.3 Hz), 7.34 (1H, d, J = 8.8 Hz), 7.21 (1H, s), 6.85 (1H, s), 6.54 (1H, s), 4.07 (2H, d, J = 7.1 Hz), 2.62 (3H, s), 1.41-1.32 (1H, m), 0.73-0.66 (2H, m), 0.47 (2H, q, J = 5.2 Hz). |
| 159 | 365 | 2.50 | Method 1 | $^1$H NMR (400 MHz, CDCl$_3$) 7.97 (1H, d, J = 8.6 Hz), 7.95 (1H, s), 7.31 (1H, d, J = 8.6 Hz), 7.11 (1H, s), 6.67 (1H, s), 4.82 (2H, s), 4.07 (2H, d, J = 7.1 Hz), 3.36 (3H, s), 2.63 (3H, s), 1.44-1.33 (1H, m), 0.72-0.66 (2H, m), 0.50-0.45 (2H, m). |
| 160 | 398 | 2.83 | Method 2 | $^1$H NMR (400 MHz, DMSO D6) 8.26 (1H, s), 8.13 (1H, s), 7.99 (1H, s), 7.28 (1H, s), 6.82 (1H, s), 4.68 (2H, s), 3.98 (2H, d, J = 7.1 Hz), 3.29 (3H, s), 2.49 (3H, s), 1.36-1.28 (1H, m), 0.56-0.51 (2H, m), 0.46-0.41 (2H, m). |

TABLE 1-continued

| Example | Molecular Ion (MH+) | Retention Time | Method | ¹H NMR data |
|---|---|---|---|---|
| 161 | 375 | 2.57 | Method 1 | ¹H NMR (400 MHz, CDCl$_3$) 8.55 (1H, d, J = 2.8 Hz), 7.96-7.92 (3H, m), 7.67 (1H, d, J = 8.8 Hz), 6.80 (1H, s), 6.60 (1H, s), 4.11 (2H, d, J = 7.3 Hz), 4.08 (2H, dd, J = 7.2, 14.5 Hz), 2.62 (3H, s), 1.46-1.38 (4H, m), 0.69-0.63 (2H, m), 0.53-0.49 (2H, m). |
| 163 | 380 | 8.34 | Method 5 | ¹H NMR (400 MHz, DMSO D6) 8.90 (1H, s), 8.60 (1H, s), 8.13 (1H, s), 7.47 (1H, d, J = 2.3 Hz), 7.22 (1H, dd, J = 2.4, 8.7 Hz), 7.07 (1H, d, J = 8.8 Hz), 6.98 (1H, s), 4.64 (2H, s), 4.34-4.27 (1H, m), 4.22-4.15 (2H, m), 3.81-3.63 (2H, m), 3.29 (3H, s), 2.06-1.96 (1H, m), 1.87-1.71 (2H, m), 1.64-1.54 (1H, m). |
| 165 | 370 | 2.50 | Method 2 | ¹H NMR (400 MHz, DMSO D6) 8.91 (1H, s), 8.62 (1H, s), 8.10 (1H, s), 7.46 (1H, d, J = 2.5 Hz), 7.22 (1H, dd, J = 2.4, 8.7 Hz), 7.07 (1H, d, J = 8.6 Hz), 6.97 (1H, s), 4.63 (2H, s), 4.42 (2H, d, J = 22.9 Hz), 3.29 (3H, s), 1.36 (6H, d, J = 21.5 Hz). |
| 167 | 398 | 3.36 | Method 1 | ¹H NMR (400 MHz, DMSO D6) 8.32 (1H, s), 8.21 (1H, s), 7.61 (1H, d, J = 2.3 Hz), 7.54 (1H, dd, J = 2.3, 8.8 Hz), 7.11 (1H, d, J = 8.8 Hz), 4.64 (2H, s), 4.01 (2H, d, J = 7.1 Hz), 3.29 (3H, s), 2.60 (3H, s), 1.37-1.29 (1H, m), 0.57-0.51 (2H, m), 0.47-0.41 (2H, m). |
| 169 | 397 | 8.62 | Method 4 | ¹H NMR (400 MHz, CDCl$_3$) 9.18 (1H, d, J = 1.5 Hz), 8.49-8.47 (1H, m), 8.35 (1H, d, J = 8.6 Hz), 8.22-8.19 (1H, m), 8.01 (1H, s), 7.94 (1H, d, J = 4.8 Hz), 7.90 (1H, s), 7.88-7.83 (1H, m), 7.63 (1H, s), 6.93 (1H, s), 4.11 (2H, d, J = 7.1 Hz), 2.68 (3H, s), 1.44-1.36 (1H, m), 0.74-0.68 (2H, m), 0.53-0.47 (2H, m). |
| 171 | 362 | 2.59 | Method 1 | ¹H NMR (400 MHz, DMSO D6) 10.24 (1H, s), 8.80 (1H, d, J = 1.8 Hz), 8.28 (1H, d, J = 8.8 Hz), 8.24-8.19 (2H, m), 7.29 (1H, s), 4.10 (2H, d, J = 7.1 Hz), 2.58 (3H, s), 2.54 (3H, s), 1.41-1.33 (1H, m), 0.58-0.46 (4H, m). |
| 173 | 377 | 2.62 | Method 2 | ¹H NMR (400 MHz, DMSO D6) 8.62 (1H, s), 8.58 (1H, d, J = 2.0 Hz), 8.27 (1H, d, J = 6.8 Hz), 8.22 (1H, s), 7.95-7.90 (1H, m), 7.66 (1H, s), 7.56 (1H, s), 7.01 (1H, d, J = 8.6 Hz), 4.11 (2H, d, J = 6.8 Hz), 3.73 (3H, s), 2.52 (3H, s), 1.35-1.27 (1H, m), 0.65-0.59 (2H, m), 0.53-0.49 (2H, m). |
| 175 | 420 | 9.94 | Method 4 | ¹H NMR (400 MHz, CDCl$_3$) 8.79 (1H, d, J = 2.5 Hz), 8.35 (1H, dd, J = 2.5, 8.8 Hz), 8.16 (1H, d, J = 1.5 Hz), 7.99 (1H, |

TABLE 1-continued

| Example | Molecular Ion (MH+) | Retention Time | Method | ¹H NMR data |
|---|---|---|---|---|
| | | | | s), 7.52 (1H, d, J = 1.5 Hz), 7.33 (1H, d, J = 8.8 Hz), 6.93 (1H, s), 6.88 (1H, s), 3.51-3.45 (2H, m), 1.29-1.20 (2H, m), 1.20-1.12 (2H, m). |
| 177 | 343 | 3.00 | Method 2 | ¹H NMR (400 MHz, CDCl$_3$) 8.68-8.65 (2H, m), 8.59 (1H, d, J = 2.0 Hz), 8.32 (1H, d, J = 8.8 Hz), 7.95 (1H, dd, J = 2.5, 8.6 Hz), 7.86 (1H, s), 7.55-7.50 (3H, m), 6.93 (1H, s), 3.50-3.43 (1H, m), 2.64 (3H, s), 1.23-1.15 (4H, m) |

Effects of the compound of the present invention of the formula (I) can be confirmed by the following experiments. Although the experimental methods are described below, the present invention is not limited thereto.

Biological Example 1

Binding Assay

The GABA$_A$α5/β3/γ2 protein used for the Scintillation Proximity Assay was derived from membranes produced from HEK293 GABA$_A$ α5/β3/γ2 expressing HEK293 cell line. HEK293 GABA$_A$ α5/β3/γ2 expressing HEK293 cell line was cultured, then harvested and centrifuged the cells. Membranes were produced by homogenization of the cell pellet with a tissue homogenizer. The resulting homogenate was centrifuged at 48,000 g for 30 minutes, re-suspended and washed twice with 10 mM potassium phosphate buffer, pH 7.4. Final resuspension of membranes took place in buffer containing 10 mM potassium phosphate and 100 mM KCl.

For assay, test compound (50×) was added 0.5 µl per well to a white-walled clear-bottomed 384-well plate.

Full signal controls were prepared by the addition of 0.5 µl of DMSO to the appropriate wells. Mixture of 10 µl of protein and 10 µl of PVT-WGA beads (0.2 mg/well) were added to the plate. Both protein and bead were diluted to the desired concentration with 10 mM potassium phosphate, pH 7.4, containing 100 mM KCl. The plate was pre-incubated for 30 minutes at room temperature with shaking before initiation of the reaction by the addition of radioligand. 5 µl of [³H]-Ro15-1788 was added at a concentration of 30 nM (5×) and the plates sealed. The reaction mix was incubated at room temperature overnight with gentle agitation on a plate shaker. The final DMSO concentration for all phases of the screening was 2% (v/v). At the end of the overnight incubation, the plates were centrifuged for two minutes at 1,000 rpm prior to reading on a Perkin Elmer Microbeta.

Concentration-response testing was performed in duplicate and the percent effect calculated for each replicate data point. The raw data was entered in Activity Base and the curves were fitted to the mean data using Excel and XL Fit, and shown as Ki.

The compounds of the present invention were tested in the above described assay, and all were found to have affinity for the GABA$_A$ α5. In certain embodiments, the preferred compounds are compounds with a Ki (nM)<100. Table 2 described below lists Ki values measured for the following examples.

TABLE 2

| Example No. | Ki (nM) |
|---|---|
| 37 | 38.8 |
| 42 | 24.0 |
| 43 | 42.0 |
| 46 | 38.0 |
| 52 | 6.7 |
| 67 | 4.1 |
| 86 | 11.8 |
| 111 | 34.6 |
| 158 | 18.4 |
| 159 | 6.4 |
| 160 | 0.9 |

Biological Example 2

Functional Assay

GABA$_A$ α5/β3/γ2 HEK293 cell line was used throughout the functional assay in PatchXpress (Molecular Devices), the automated patch-clamp system. Cells stably expressing the appropriate GABA$_A$ subtype (α5/β3/γ2, α1/β3/γ2, α2/β3/γ2 or α3/β3/γ2) were dissociated from poly-D-lysine treated tissue culture flasks using a mixture of one part TrypLE (Invitrogen, cat #12604): one part Dulbecco's Phosphate Buffered Saline (Invitrogen, cat #14190). The dissociated cells were re-suspended in growth media (D-MEM/F-12 media (Invitrogen, cat #11320) supplemented with 10% (v/v) Foetal Bovine Serum (Invitrogen, cat #10082) and 1% (v/v) non-essential amino acids (Invitrogen, cat #11140)) and allowed to recover for one hour at 37° C. in a humidified incubator with 5% CO$_2$. At the end of the recovery period cells were centrifuged at 1,000 rpm for two minutes and the resulting pellet re-suspended in external solution (in mM; 137 NaCl, 4 KCl, 10 HEPES, 1.8 CaCl$_2$, 1 MgCl$_2$, 10 glucose, pH set to 7.35 with NaOH). Cells were counted and diluted to 2.5×10⁶/ml in external solution. The patch-clamp assay protocol involved determination of current amplitude with control applications of GABA EC$_{20}$ containing concentration-matched DMSO (0.3% v/v), then pre-incubation of the test compound for one minute prior to the addition of the same compound diluted with the GABA EC$_{20}$. Compound and/or GABA was applied for five seconds, with two minute wash periods between applications. No wash period was present at the end of the compound pre-application stage. The internal solution comprised (in mM) 90 KCl, 50 KF, 11 EGTA, 10 HEPES, 1 MgCl$_2$, 2

Mg-ATP, the pH was set to 7.35 with KOH and the holding potential was −60 mV. Compounds were assayed at a concentration of 1 μM. Current amplitudes obtained from GABA applications in the presence of test compound were normalized to the control response obtained with GABA alone. % change of GABA response was showed as a function of the compound.

The compounds of the present invention were tested in the above described assay, and all were found to possess $GABA_A$ α5 NAM activity and selectivity for the α5 subtype over the α1, α2, and α3. In certain embodiments, the preferred compounds have a functional efficacy at the α5 subtype of less than −20%, more preferred compounds have a functional efficacy at the α5 subtype of less than −40%.

In certain embodiments, the preferred compounds bind selectively to the α5 subtype 2, 4 and particularly 10 times compared to the α1, α2 or α3 subtype. Preferably, this binding selectivity is shown over all these subunits.

TABLE 3

| Example No. | α5 1 uM (%) | α1 1 uM (%) |
|---|---|---|
| 37 | −46.0 | 5.0 |
| 42 | −55.9 | −0.2 |
| 43 | −55.1 | −8.0 |
| 46 | −42.4 | 0.9 |
| 52 | −41.8 | −7.5 |
| 67 | −52.5 | 0.5 |
| 86 | −49.4 | 3.3 |
| 111 | −44.4 | 0.3 |
| 158 | −50.0 | −8.3 |
| 159 | −46.7 | −4.8 |
| 160 | −42.5 | −9.8 |

Biological Example 3

The Rat Novel Object Recognition Test

Background

NOR (Novel Object Recognition test) is a two-trial spontaneous test of visual recognition memory that relies on the animal's natural tendency to explore novelty (Behav Brain Res, 1998, 31(1): pp. 47-59). Variation of the inter-trial interval (ITI) between acquisition (T1) and retention trials (T2) may be used to investigate either deficits or improvements in memory. A temporal performance deficit can be induced by increasing the ITI (approximately 24 hr), such that exploration of both objects in T2 is similar, enabling the pro-cognitive abilities of novel compounds to be evaluated.

Study Design

Male, Lister Hooded rat (228-273 g at start of study; Harlan UK) was used.

Habituation to the grey, matt perspex NOR box twice a day, on two consecutive days, prior to testing. Each habituation session, consisted of a 3 min exposure to the empty test box (46×30×45 cm), followed by 1 min in the side annex (13×30×45 cm), and then a further 3 min in the test area. Animals were sham dosed with the appropriate vehicle and via the appropriate dose route prior to the second habituation session on each day.

The NOR test comprises of two sessions, T1 and T2, each lasting 3 minutes.

On the first test day (T1), rats were again habituated for 3 min in the empty test box prior to testing. Following 3 min habituation to the empty test box, the rat was placed into the side annex and 2 identical objects were placed into the test arena, equally spaced to each other and the 2 side walls. The rat was then returned to the test area and allowed to freely explore the objects for 3 min. Following the 3 min test session, the rat was returned to its home cage.

Following a 24 hr delay, the test was repeated (T2) except that one of the familiar objects was substituted for a novel one of the same colour, material and similar size but different shape. The objects used were black pyramid and tower shapes that had been previously validated in this test and shown to be of equal saliency. The protocol was similar to T1 with a 3 min habituation, followed by approx. 1 min in the annex while the objects were positioned in the box, followed by 3 min exposure to the objects. Between trials objects were cleaned with 70% ethanol.

The study design was randomised as far as was practically possible. Treatments were balanced such that in each n=12, 6 had a tower as the familiar object and 6 had a pyramid and out of each 6 sub-group 3 had the novel object on the left and 3 had the novel object on the right. In terms of dosing, the groups were randomised as far as possible throughout the day and across the 4 test boxes used. The compounds of the present invention were administered 30 min prior to T1 and T2.

Evaluation of Study

Experimental protocol tests for improvement in attention/recognition memory via reversal of a 24 h delay-induced deficit in NOR. The performance measures at T2 are: d1 index (overall difference)=time spent exploring novel object−time spent exploring familiar object; d2 index=d1 index/total exploration time; (T2) T1 score=total time exploring both objects in T1; T2 score=total time exploring both objects in T2. All performance measures were determined for each individual animal before statistical handling.

Statistical Analysis

The T1 score, d1 and d2 index were analysed using 2-way ANOVA (treatment×object) followed by planned comparisons post-hoc LSD using single measure parametric analysis, based on least square (predicted) means in InVivoStat, UK.

Result

The result is shown in FIG. 1.

Example 160 at 20 mg/kg (p.o.) significantly improved performance, as measured by an increase in d2 index score.

Biological Example 4

Cryopreserved Hepatocyte/Hepatic Microsomal Stability

Cryopreserved Hepatocyte Stability: Half-life/Intrinsic Clearance Format

Hepatocyte stability assays were performed using pooled human cryopreserved hepatocytes. Test and control compounds (testosterone, midazolam, 4-methylumbelliferone), prepared in DMSO, were incubated at an initial concentration of 1 μM (0.25% DMSO final, n=2) with hepatocytes at cell densities of 0.5 million cells/mL for both species at 37° C. Aliquots were removed at 0, 10, 20, 45 and 90 minutes for termination of reactions and compound extraction with acetonitrile containing an analytical internal standard. Samples were centrifuged and the supernatant fractions analysed for parent compound by mass spectrometry (LC-MS/MS).

The amount of compound remaining (expressed as %) was determined from the MS response in each sample relative to that in the T=0 samples (normalised for internal standard).

Ln plots of the % remaining were used to determine the half-life for compound disappearance using the relationship:

$$t\frac{1}{2}(\min)=-0.693/\lambda$$

where λ is the slope of the Ln % remaining vs time curve.
Hepatic Microsomal Stability: Half-life/Intrinsic Clearance Format Microsomal stability assays were performed using pooled hepatic microsomes from human. Test and control compounds (propranolol or dextromethorphan, midazolam), prepared in DMSO, were incubated at an initial concentration of 1 μM (0.25% DMSO final, n=2) with microsomes (0.5 mg protein/mL) at 37° C. in the presence of the cofactor, NADPH (1 mM). Aliquots were removed at 0, 5, 10, 20 and 40 minutes for termination of reactions and compound extraction with acetonitrile containing an analytical internal standard. Samples were centrifuged and the supernatant fractions analysed for parent compound by mass spectrometry (LC-MS/MS).

The amount of compound remaining (expressed as %) was determined from the MS response in each sample relative to that in the T=0 samples (normalised for internal standard).

Ln plots of the % remaining were used to determine the half-life for compound disappearance using the relationship:

$$t\frac{1}{2}(\min)=-0.693/\lambda$$

where λ is the slope of the Ln % remaining vs time curve.

Table 4 described below lists cryopreserved hepatocyte stability and hepatic microsomal stability for the following examples.

TABLE 4

| Example No. | hepatocyte stability (%) | microsomal stability (%) |
|---|---|---|
| 87 | 103 | 76 |
| 88 | 81 | 95 |
| 95 | 96 | 89 |
| 120 | 85 | 94 |
| 124 | 75 | 72 |
| 151 | 101 | 77 |
| 157 | 87 | 78 |

Formulation Example 1

The following components were admixed in conventional method and punched out to obtain 10,000 tablets each containing 10 mg of active ingredient.

| | |
|---|---|
| 6-Chloro-7-((3-(cyclopropylmethyl)-7-methyl-3H-imidazo[4,5-b]pyridin-5-yl)amino)-4-methyl-2H-benzo[b][1,4]oxazin-3(4H)-one | 100 g |
| Carboxymethylcellulose calcium (disintegrating agent) | 20 g |
| Magnesium stearate (lubricating agent) | 10 g |
| Microcrystalline cellulose | 870 g |

Formulation Example 2

The following components were admixed in conventional method. The solution was sterilized in conventional manner, filtered through dust removal equipment, placed 5 mL portions into ampoules and sterilized by autoclave to obtain 10,000 ampoules each containing 20 mg of the active ingredient.

| | |
|---|---|
| 6-Chloro-7-((3-(cyclopropylmethyl)-7-methyl-3H-imidazo[4,5-b]pyridin-5-yl)amino)-4-methyl-2H-benzo[b][1,4]oxazin-3(4H)-one | 200 g |
| mannitol | 20 g |
| distilled water | 50 L |

INDUSTRIAL APPLICABILITY

The compound of the present invention represented by formula (I) acts as potent and selective $GABA_A$ α5 negative allosteric modulator. The compound of the present invention can therefore be used for the treatment or prevention of diseases which are related to the $GABA_A$ α5 receptor.

The invention claimed is:
1. A compound represented by formula (I):

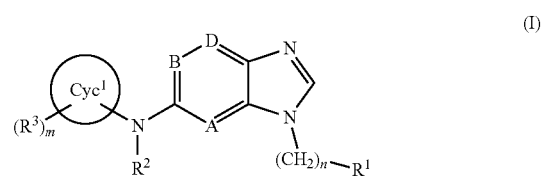

wherein A represents N;
B represents $CR^5$;
D represents $CR^6$ or N;
$Cyc^1$ represents a (1) 5- to 15- membered mono-, bi- or tri-cyclic aromatic carbocyclic ring which may be partially saturated or (2) 5- to 15- membered mono-, bi- or tri-cyclic aromatic heterocyclic ring having 1 to 5 heteroatoms independently selected from nitrogen, oxygen and sulfur, which may be partially saturated;
$R^1$ represents (1) 3- to 5-membered cycloalkyl wherein one carbon atom may be replaced by oxygen, which may be substituted with one or more groups independently selected from halogen and C1-4 alkyl which may be substituted with halogen or (2) C1-4 alkyl which may be substituted with halogen;
$R^2$ represents hydrogen or C1-4 alkyl;
$R^3$ represents (1) oxo, (2) halogen, (3) cyano, (4) hydroxy, (5) C1-6 alkyl which may be substituted with $R^7$, (6) C1-6 alkoxy which may be substituted with $R^7$, (7) 3- to 5-membered cycloalkyl wherein one carbon atom may be replaced by oxygen, which may be substituted with $R^8$, (8) 5- to 12- membered mono- or bi- cyclic aromatic carbocyclic ring which may be partially or fully saturated and may be substituted with $R^8$ or (9) 5- to 12- membered mono- or bi-cyclic aromatic heterocyclic ring having 1 to 5 heteroatoms independently selected from nitrogen, oxygen and sulfur, which may be partially or fully saturated and may be substituted with $R^8$;
$R^5$ represents (1) hydrogen, (2) halogen, (3) hydroxy, (4) cyano, (5) C1-6 alkyl which may be substituted with $R^9$, (6) C2-6 alkenyl which may be substituted with $R^9$, (7) C1-6 alkoxy which may be substituted with $R^9$, (8) C1-6 alkyl-carbonyl which may be substituted with $R^9$ or (9) 3- to 5-membered cycloalkyl wherein one carbon atom may be replaced by oxygen, which may be substituted with $R^9$;
$R^6$ represents hydrogen, halogen or C1-4 alkyl which may be substituted with halogen;

$R^7$ represents (1) halogen, (2) hydroxy, (3) C1-4 alkoxy or (4) 3- to 5-membered cycloalkyl wherein one carbon atom may be replaced by oxygen, which may be substituted with one or more groups independently selected from halogen and hydroxy;

$R^8$ represents (1) oxo, (2) halogen, (3) cyano, (4) hydroxy, (5) C1-6 alkyl which may be substituted with one or more groups independently selected from halogen and hydroxy or (6) 3- to 5-membered cycloalkyl which may be substituted with one or more groups independently selected from halogen and hydroxy;

$R^9$ represents halogen or hydroxy;

n represents an integer of 0 to 2; and m represents an integer of 0 to 7, wherein when m represents an integer of 2 to 7, each $R^3$ may be same or different;

with the proviso that (a) the compound represented by formula (I), wherein D is CH, and (1) $R^1$ is C1-4 alkyl which may be substituted with halogen or (2) n is 0 and $R^1$ is cycloalkyl, are excluded, or a pharmaceutically acceptable salt thereof, an N-oxide thereof, or a solvate thereof.

2. The compound according to claim 1, which is a compound represented by formula (I-B):

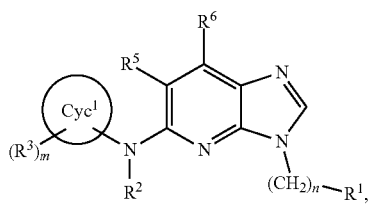

(I-B)

or
a compound represented by formula (I-D):

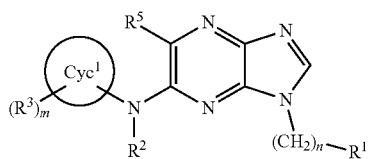

(I-D)

wherein all the symbols have the same meanings as described in claim 1.

3. The compound according to claim 2, which is a compound represented by formula (I-B) wherein $R^6$ represents halogen or C1-4 alkyl which may be substituted with halogen.

4. The compound according to claim 1, wherein $R^1$ represents cyclopropyl, cyclobutyl, oxetanyl, tetrahydrofuranyl, n-propyl or isopropyl, any of which may be substituted with 1 to 3 halogen.

5. The compound according to claim 1, wherein n represents 0 or 1.

6. The compound according to claim 1, wherein $R^2$ represents hydrogen.

7. The compound according to claim 1, wherein $(R^3)_m\text{—Cyc}^1\rightarrow$ represents —continued

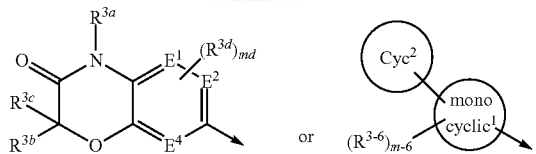

wherein $E^1$, $E^2$ and $E^4$ each independently represent a carbon atom or a nitrogen atom, with the proviso that at least two of $E^1$, $E^2$ and $E^4$ are carbon atoms;

$R^{3a}$ represents (1) hydrogen, (2) C1-4 alkyl which may be substituted with 1 to 3 groups selected from halogen, hydroxy and methoxy or (3) —(CH$_2$)$_p$-(3- to 5-membered cycloalkyl), wherein one carbon atom in cycloalkyl may be replaced by oxygen and p represents 0 or 1;

$R^{3b}$ and $R^{3c}$ each independently represent (1) hydrogen, (2) halogen or (3) C1-4 alkyl;

$R^{3d}$ represents halogen or C1-4 alkyl;

md represents an integer of 0 to 2, wherein when md represents 2, each $R^{3d}$ may be same or different;

monocyclic$^1$ represents (1) 5- to 7- membered monocyclic aromatic carbocyclic ring which may be partially saturated or (2) 5- to 7- membered mono-cyclic aromatic heterocyclic ring having 1 to 3 heteroatoms independently selected from nitrogen, oxygen and sulfur, which may be partially saturated;

Cyc$^2$ represents (1) 5- to 6- membered mono-cyclic aromatic heterocyclic ring having 1 to 3 heteroatoms independently selected from nitrogen, oxygen and sulfur, which may be partially or fully saturated and may be substituted with 1 to 3 groups selected from oxo, halogen, cyano, hydroxy and C1-4 alkyl which may be substituted with 1 to 3 groups selected from halogen and hydroxy or (2) 8- to 12-membered bicyclic aromatic heterocyclic ring having 1 to 5 heteroatoms independently selected from nitrogen, oxygen and sulfur, which may be partially or fully saturated and may be substituted with 1 to 5 groups selected from oxo, halogen, cyano, hydroxy and C1-4 alkyl which may be substituted with 1 to 3 groups selected from halogen and hydroxyl;

$R^{3-6}$ represents halogen or C1-4 alkyl which may be substituted with 1 to 3 halogen;

m-6 represents 0 to 2; wherein when m-6 represents 2, each $R^{3-6}$ may be same or different and the arrow represents a binding position to the N($R^2$).

8. The compound according to claim 1, wherein a compound represented by formula (IV):

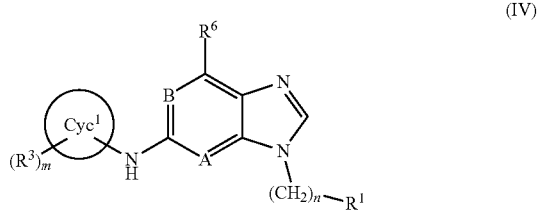

(IV)

wherein A represents N; B represents CR$^5$;

$R^1$ represents cyclopropyl, cyclobutyl, oxetanyl, tetrahydrofuranyl, n-propyl or isopropyl, any of which may be substituted with 1 to 3 halogen;

R⁵ represents (1) hydrogen, (2) halogen, (3) hydroxy, (4) cyano, (5) C1-4 alkyl which may be substituted with 1 to 3 groups selected from halogen and hydroxy, (6) C2-4 alkenyl which may be substituted with 1 to 3 groups selected from halogen and hydroxy, (7) C1-4 alkoxy which may be substituted with 1 to 3 groups selected from halogen and hydroxy, (8) C1-4 alkyl-carbonyl which may be substituted with 1 to 3 groups selected from halogen and hydroxy or (9) 3- to 5-membered cycloalkyl wherein one carbon atom may be replaced by oxygen, which may be substituted with 1 to 3 groups selected from halogen and hydroxyl;

R⁶ represents halogen or methyl which may be substituted with halogen;

n represents 0 or 1;

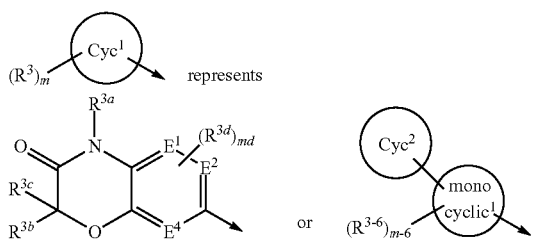

wherein $E^1$, $E^2$ and $E^4$ each independently represent a carbon atom or a nitrogen atom, with the proviso that at least two of $E^1$, $E^2$ and $E^4$ are carbon atoms;

$R^{3a}$ represents (1) hydrogen, (2) C1-4 alkyl which may be substituted with 1 to 3 groups selected from halogen, hydroxy and methoxy or (3) —(CH$_2$)$_p$-(3- to 5-membered cycloalkyl), wherein one carbon atom in cycloalkyl may be replaced by oxygen and p represents 0 or 1;

$R^{3b}$ and $R^{3c}$ each independently represent (1) hydrogen, (2) halogen or (3) C1-4 alkyl;

$R^{3d}$ represents halogen or C1-4 alkyl;

md represents an integer of 0 to 2, wherein when md represents 2, each $R^{3d}$ may be same or different;

monocyclic¹ represents (1) 5- to 7- membered mono-cyclic aromatic carbocyclic ring which may be partially saturated or (2) 5- to 7- membered mono-cyclic aromatic heterocyclic ring having 1 to 3 heteroatoms independently selected from nitrogen, oxygen and sulfur, which may be partially saturated;

Cyc² represents (1) 5- to 6- membered mono-cyclic aromatic heterocyclic ring having 1 to 3 heteroatoms independently selected from nitrogen, oxygen and sulfur, which may be partially or fully saturated and may be substituted with 1 to 3 groups selected from oxo, halogen, cyano, hydroxy and C1-4 alkyl which may be substituted with 1 to 3 groups selected from halogen and hydroxy or (2) 8- to 12-membered bicyclic aromatic heterocyclic ring having 1 to 5 heteroatoms independently selected from nitrogen, oxygen and sulfur, which may be partially or fully saturated and may be substituted with 1 to 5 groups selected from oxo, halogen, cyano, hydroxy and C1-4 alkyl which may be substituted with 1 to 3 groups selected from halogen and hydroxyl;

$R^{3-6}$ represents halogen or C1-4 alkyl which may be substituted with 1 to 3 halogen;

m-6 represents 0 to 2; wherein when m-6 represents 2, each $R^{3-6}$ may be same or different; and the arrow represents a binding position to the N(R²).

9. The compound according to claim 1, wherein

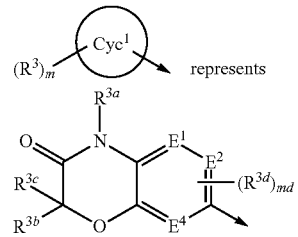

wherein $E^1$, $E^2$ and $E^4$ each independently represent a carbon atom or a nitrogen atom, with the proviso that at least two of $E^1$, $E^2$ and $E^4$ are carbon atoms;

$R^{3a}$ represents (1) hydrogen, (2) C1-4 alkyl which may be substituted with 1 to 3 groups selected from halogen, hydroxy and methoxy or (3) —(CH$_2$)$_p$-(3- to 5-membered cycloalkyl), wherein one carbon atom in cycloalkyl may be replaced by oxygen and p represents 0 or 1;

$R^{3b}$ and $R^{3c}$ each independently represent (1) hydrogen, (2) halogen or (3) C1-4 alkyl;

$R^{3d}$ represents halogen or C1-4 alkyl;

md represents an integer of 0 to 2, wherein when md represents 2, each $R^{3d}$ may be same or different;

monocyclic¹ represents (1) 5- to 7- membered mono-cyclic aromatic carbocyclic ring which may be partially saturated or (2) 5- to 7- membered mono-cyclic aromatic heterocyclic ring having 1 to 3 heteroatoms independently selected from nitrogen, oxygen and sulfur, which may be partially saturated; and the arrow represents a binding position to the N(R²).

10. The compound according to claim 1, wherein

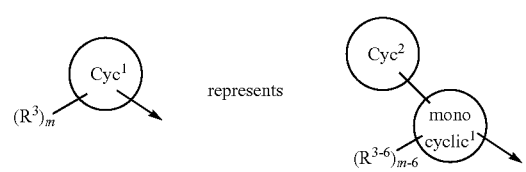

wherein monocyclic¹ represents (1) 5- to 7- membered mono-cyclic aromatic carbocyclic ring which may be partially saturated or (2) 5- to 7- membered mono-cyclic aromatic heterocyclic ring having 1 to 3 heteroatoms independently selected from nitrogen, oxygen and sulfur, which may be partially saturated;

Cyc² represents (1) 5- to 6- membered mono-cyclic aromatic heterocyclic ring having 1 to 3 heteroatoms independently selected from nitrogen, oxygen and sulfur, which may be partially or fully saturated and may be substituted with 1 to 3 groups selected from oxo, halogen, cyano, hydroxy and C1-4 alkyl which may be substituted with 1 to 3 groups selected from halogen and hydroxy or (2) 8- to 12-membered bicyclic aromatic heterocyclic ring having 1 to 5 heteroatoms independently selected from nitrogen, oxygen and sulfur, which may be partially or fully saturated and may be substituted with 1 to 5 groups selected from oxo, halogen, cyano, hydroxy and C1-4 alkyl which may be substituted with 1 to 3 groups selected from halogen and hydroxyl;

$R^{3-6}$ represents halogen or C1-4 alkyl which may be substituted with 1 to 3 halogen;

m-6 represents 0 to 2; wherein when m-6 represents 2, each $R^{3-6}$ may be same or different; and the arrow represents a binding position to the $N(R^2)$.

11. The compound according to claim 7, wherein mono-cyclic$^1$ represents 6-membered mono-cyclic aromatic ring having 0 to 2 nitrogen atom and Cyc$^2$ represents nitrogen-containing 5- to 6- membered mono-cyclic aromatic hetero-cyclic ring having 1 to 3 heteroatoms independently selected from nitrogen, oxygen and sulfur, which may be substituted with 1 to 3 groups selected from halogen, cyano, hydroxy and C1-4 alkyl which may be substituted with 1 to 3 groups selected from halogen and hydroxy.

12. The compound according to claim 7, wherein mono-cyclic$^1$ represents benzene or pyridine.

13. The compound according to claim 1, wherein the compound is selected from the group consisting of (1) 7-((1-(Cyclopropylmethyl)-1H-imidazo[4,5-b]pyrazin-6-yl)amino)-4-methyl-2H-benzo[b][1,4]oxazin-3(4H)-one, (2) 6-((1-(Cyclopropylmethyl)-1H-imidazo[4,5-b]pyrazin-6-yl)amino)-3-methylbenzo[d]oxazol-2(3H)-one, (3) 7-((3-(Cyclopropylmethyl)-3H-imidazo[4,5-b]pyridin-5-yl)amino)-1-methyl-1H-pyrido[2,3-b][1,4]oxazin-2(3H)-one, (4) 6-((3-(Cyclopropylmethyl)-7-(trifluoromethyl)-3H-imidazo[4,5-b]pyridin-5-yl)amino)-1-methyl-1H-pyrido[2,3-b][1,4]oxazin-2(3H)-one, (5) N-(5-(1H-Imidazol-1-yl)pyridin-2-yl)-3-(cyclopropylmethyl)-7-methyl-3H-imidazo[4,5-b]pyridin-5-amine, (6) N-(6-(1H-Imidazol-1-yl)pyridin-3-yl)-3-(cyclopropylmethyl)-7-methyl-3H-imidazo[4,5-b]pyridin-5-amine, (7) 6-((3-(Cyclopropylmethyl)-7-methyl-3H-imidazo[4,5-b]pyridin-5-yl)amino)-1-methyl-1H-pyrido[2,3-b][1,4]oxazin-2(3H)-one and (8) 6-Chloro-7-((3-(cyclopropylmethyl)-7-methyl-3H-imidazo[4,5-b]pyridin-5-yl)amino)-4-methyl-2H-benzo[b][1,4]oxazin-3(4H)-one.

14. A pharmaceutical composition comprising the compound according to claim 1, a pharmaceutically acceptable salt thereof, an N-oxide thereof, or a solvate thereof as an active ingredient.

15. A medicament comprising a combination of the compound according to claim 1, a pharmaceutically acceptable salt thereof, an N-oxide thereof, or a solvate thereof with a acetylcholinesterase inhibitor and/or N-methyl-D-aspartate (NMDA) receptor antagonist.

16. A method of treating a disease which is related to $GABA_A$ α5 comprising administering an effective amount of the compound according to claim 1, a pharmaceutically acceptable salt thereof, an N-oxide thereof, or a solvate thereof to a mammal, wherein the disease which is related to $GABA_A$ α5 is Alzheimer's disease; schizophrenia.

* * * * *